United States Patent [19]

Teboul

[11] Patent Number: 5,709,206

[45] Date of Patent: Jan. 20, 1998

[54] IMAGING SYSTEM FOR BREAST SONOGRAPHY

[76] Inventor: Michel Teboul, 81, Boulevard Suchet, 71016 Paris, France

[21] Appl. No.: 562,696

[22] Filed: Nov. 27, 1995

[51] Int. Cl.$^6$ ................................................ A61B 8/00
[52] U.S. Cl. .......................... 128/653.1; 128/660.01; 128/915; 128/916; 128/920; 382/294
[58] Field of Search .................. 128/653.1, 915, 128/916, 660.01, 660.04, 660.06, 660.07, 660.1; 364/413.13, 413.22, 413.25; 382/132, 294

[56] References Cited

U.S. PATENT DOCUMENTS

| | | | |
|---|---|---|---|
| 3,964,296 | 6/1976 | Matzuk | 73/67.5 R |
| 4,478,083 | 10/1984 | Hassler et al. | |
| 4,932,414 | 6/1990 | Coleman et al. | 128/660.09 |
| 5,003,979 | 4/1991 | Merickel et al. | |
| 5,050,200 | 9/1991 | Tirelli et al. | 378/149 |
| 5,181,513 | 1/1993 | Touboul et al. | |
| 5,224,036 | 6/1993 | Ito et al. | |
| 5,245,539 | 9/1993 | Romeas et al. | |
| 5,260,871 | 11/1993 | Goldberg | |
| 5,261,404 | 11/1993 | Mick et al. | 128/653.1 |
| 5,329,929 | 7/1994 | Sato et al. | 128/660.65 |
| 5,370,120 | 12/1994 | Oppelt et al. | 128/660.03 |
| 5,396,890 | 3/1995 | Weng | 128/660.07 |
| 5,413,106 | 5/1995 | Fujita et al. | 128/660.07 |
| 5,454,371 | 10/1995 | Fenster et al. | |
| 5,572,565 | 11/1996 | Abdel-Mottaleb | |

FOREIGN PATENT DOCUMENTS

| | | |
|---|---|---|
| 2706275 | 12/1994 | France |
| 4183453 | 6/1992 | Japan |

OTHER PUBLICATIONS

Carson et al. "Breast Imaging in Coronal Planes with Simultaneous Pulse Echo and Transmission Ultrasound" Dec. 1981 pp. 1141–1144.

Primary Examiner—Marvin M. Lateef
Assistant Examiner—Shawna J. Shaw
Attorney, Agent, or Firm—Robert C. Kain, Jr.

[57] ABSTRACT

The present invention relates to a method and an apparatus for processing a plurality of ultrasound images of ductolobular systems in a breast. The operator scans each particular duct system in the breast and saves these axial scan segments. Further, the operator scans the ductolobular systems transaxially. The imaging system, interactively with the operator, aligns the axial scan segments of the duct. This is accomplished by electronically noting the radial direction of the axial scan or by identifying two like image points on respective, sequential axial scan segments. A composite axial scan image in compiled by aligning multiple, sequential axial scan segments together. The associated transductal scan images are mapped to the axial scan segment. The composite axial scan image is displayed with a clockface template of the breast, a vertical, cross-section template of the breast and a three dimensional composite image of the breast. To form the three dimensional composite image, the operator must axially scan the ductal system through at least two scan planes which are radially centered about the axial centerline of the duct's axis. For example, the images are scanned at 45° with respect to the skin of the patient and at 110° with respect to the skin surface wherein both scans include the same axial segment of the duct. To form the three-dimensional image, the system aligns and forms two full axial composite images at each scan angle, then aligns the ductal centerlines of both axial composite images. Each scan plane image is displayed at an angle with respect to the other plane and a composite three dimensional image is formed with a template showing the nipple. Color coding, magnification of ductolobular systems, and image isolation are enhancements to the basic imaging system.

32 Claims, 22 Drawing Sheets

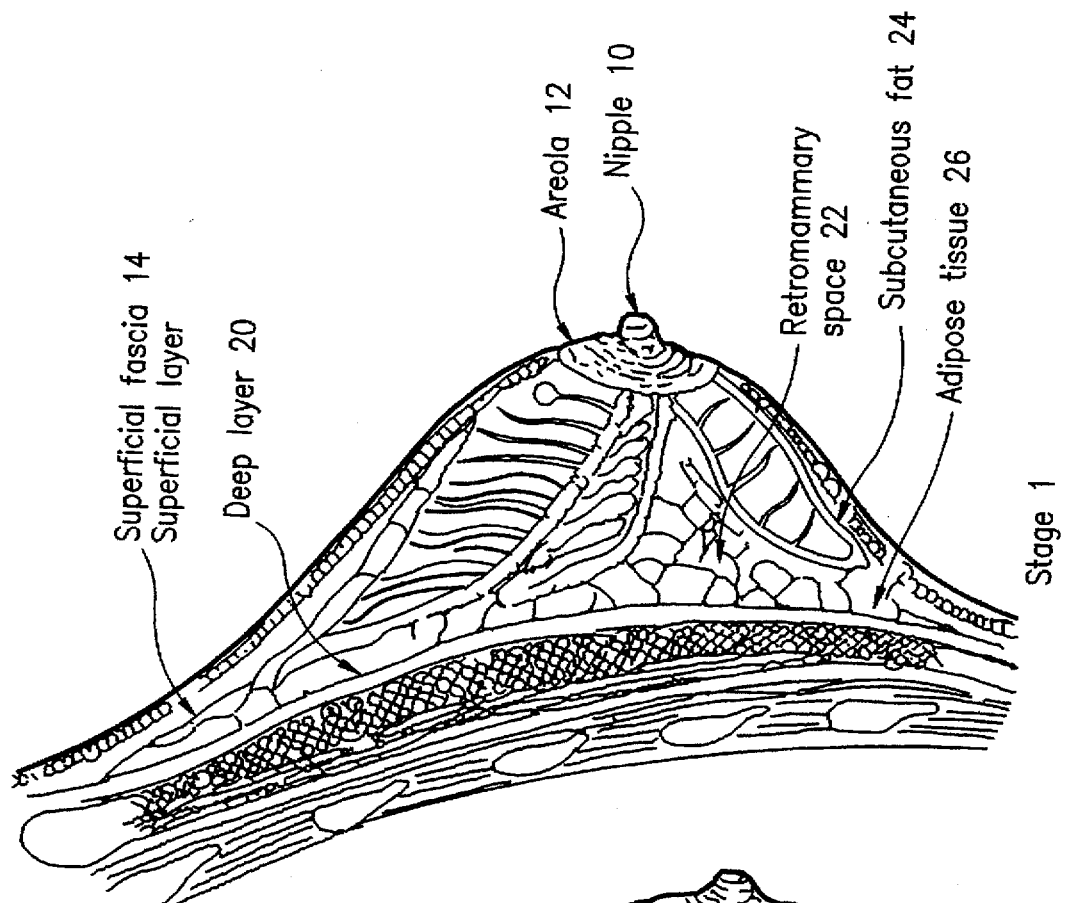
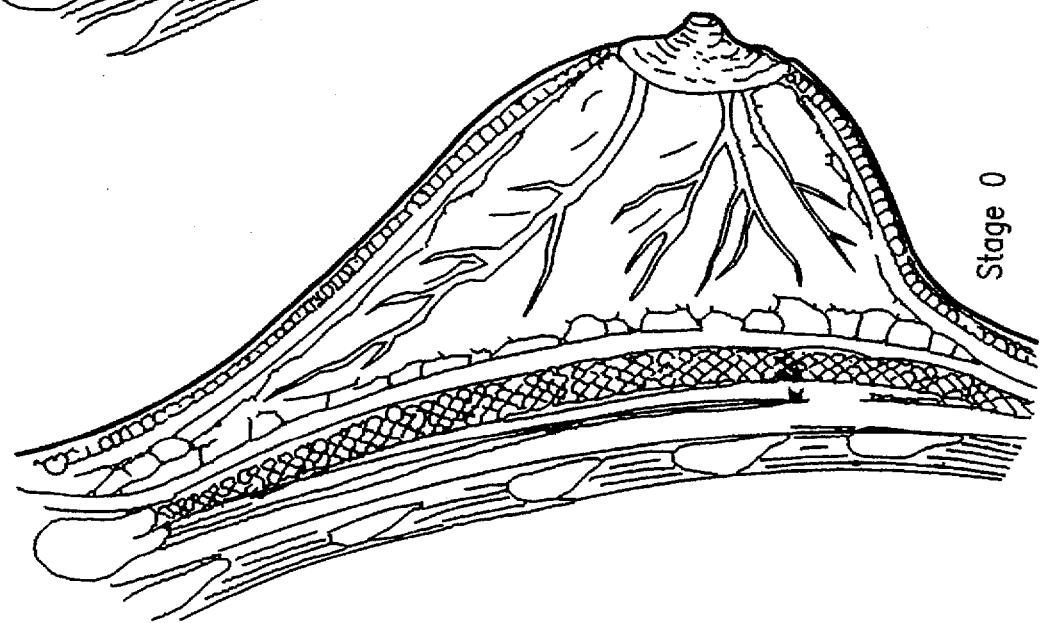

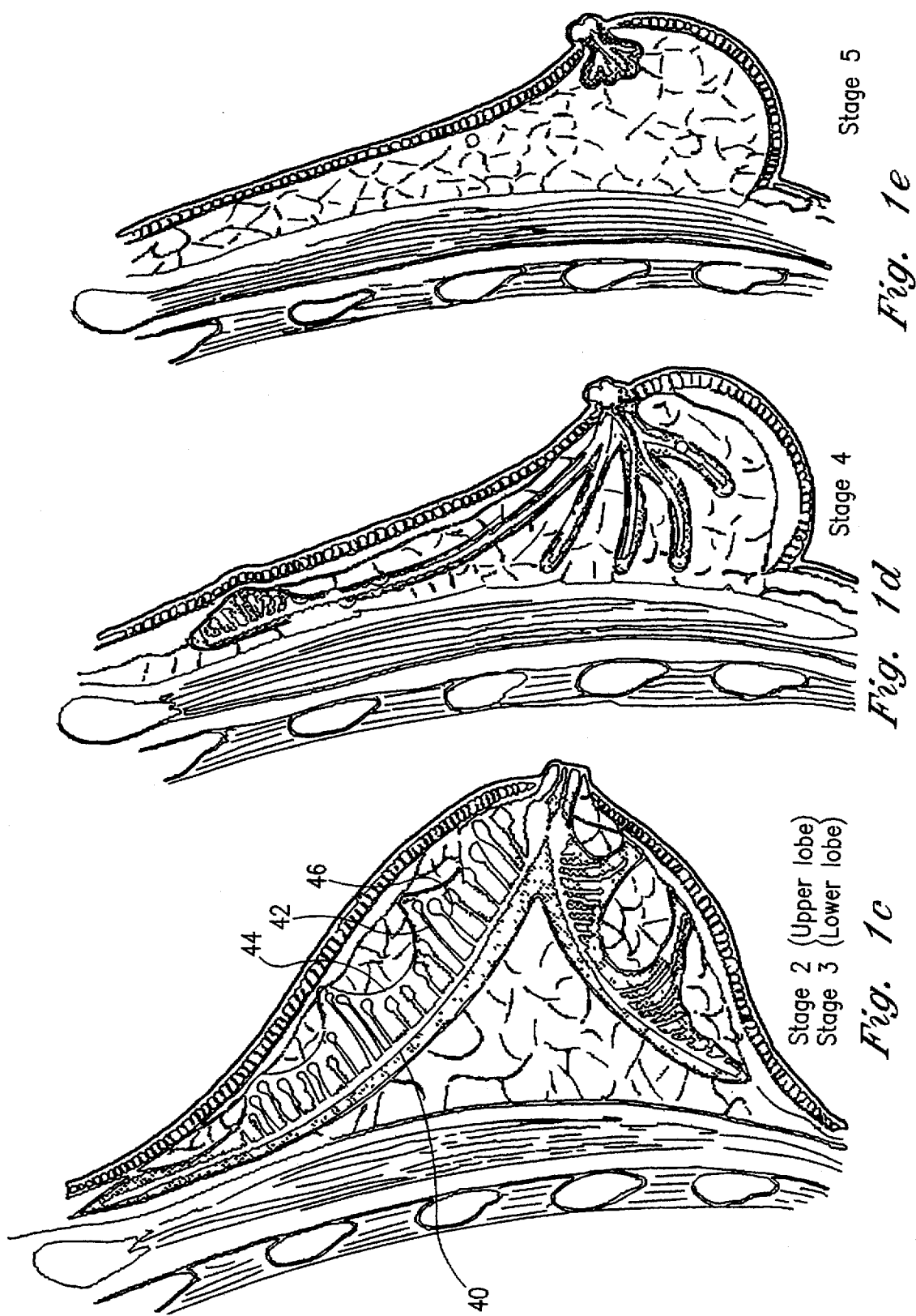

Fig. 3

IMAGING SYSTEM FOR BREAST SONOGRAPHY

BACKGROUND OF THE INVENTION

The present invention relates to the sonographic method and imaging system to detect breast cancer at early stages.

Breast cancer affects 1 of every 10 women in the modern world. Breast cancer affects women from 35 years of age and older. In order to detect breast cancer at an early stage, a common medical practice utilizes an X-ray mammogram. Unfortunately, the X-ray mammogram provides only a shadow graph of the breast. This image is insufficient for many reasons, discussed below, but primarily because the structure of the breast sought to be studied is not directly radio-visible.

With the event of ultrasound devices, greater opportunity has arisen to detect and track the early signs of breast cancer in women.

OBJECTS OF THE INVENTION

It is an object of the present invention to provide an imaging system which is utilized to detect the early stages of breast cancer.

It is a further object of the present invention to provide an imaging system which paints the ultrasound image on a template such that the physician or the technician can immediately identify the special orientation of the duct and within it the location where the coalescent dusters of malignant cells may develop.

It is a further object of the present invention to provide an imaging system whereby the operator can piece together several sonograms to provide an entire ductal image.

It is a further object of the present invention to display the ductal image together with the main line of lobules in a ductal lobular scan image.

It is another object of the present invention to provide an imaging system whereby the operator can piece together or show or demonstrate several or all the ducts within a breast to display a map of the ducts in the breast or in one or two quadrants of the breast.

It is a further object of the present invention to show several ductal or all ductal lobular images in the breast in a three-dimensional manner.

It is a further object of the present invention to provide an imaging system which enables the physician or the medical technician to see the duct under study both in an axial ductal manner and a transductal manner or view.

It is an additional object of the present invention to provide an imaging system wherein the duct under study is shown in a three dimensional manner on a computer screen.

SUMMARY OF THE INVENTION

The present invention relates to a method and an apparatus for processing a plurality of ultrasound images of ductolobular systems in a breast. The operator scans each particular duct system in the breast and saves these axial scan segments. Further, the operator scans the ductolobular systems transaxially. The imaging system, interactively with the operator, aligns the axial scan segments of the duct. This is accomplished by electronically noting the radial direction of the axial scan or by identifying two like image points on respective, sequential axial scan segments. A composite axial scan image is compiled by aligning multiple, sequential axial scan segments together. The associated transductal scan images are mapped to the axial scan segment. The composite axial scan image is displayed with a clockface template of the breast, a vertical, cross-section template of the breast and a three dimensional composite image of the breast. To form the three dimensional composite image, the operator must axially scan the ductal system through at least two scan planes which are radially centered about the axial centerline of the duct's axis. For example, the operator obtains an axial duct scan at 45° with respect to the skin of the patient and at 110° with respect to the skin surface wherein both scans include the same axial segment of the duct. The form the 3D image, the system aligns and forms two full axial composite images at each scan angle, then aligns the ductal centerlines of both axial composite images. Each scan plane image is displayed at an angle with respect to the other scan plane and a composite three dimensional image is formed with a template showing the nipple of the breast. Color coding, magnification of ductolobular systems, and image isolation are enhancements to the basic imaging system.

BRIEF DESCRIPTION OF DRAWINGS

Further objects and advantages of the present invention can be found in the detailed description of the preferred embodiment when taken in conjunction with the accompanying drawings in which:

FIGS. 1a–e and 2a and 2b show diagrammatic representation of a woman's breast in cross-section, the six (6) major post-prepubertal anatomical stages (FIG. 1c shows two of the most critical stages, the upper half being Stage 2 and the lower half being Stage 3) and a schematic anatomy of the mammary lobe and a schematic anatomy of the representation of the ductolobular system (FIGS. 2a and 2b, respectively).

FIG. 3 is a chart which shows conventional classifications of breast malignancies based upon succinct geometric concepts of shape, shade, boundaries, uniformity and shadowing detected based upon conventional use of ultrasound rather than the ductal echography described herein.

FIG. 7b diagrammatically illustrates the resulting axial duct image obtained from FIG. 7a.

FIGS. 16a–e illustrate a flow chart showing the major features of the computer system and method as part of the present invention.

DETAILED DESCRIPTION

Figure 2A:
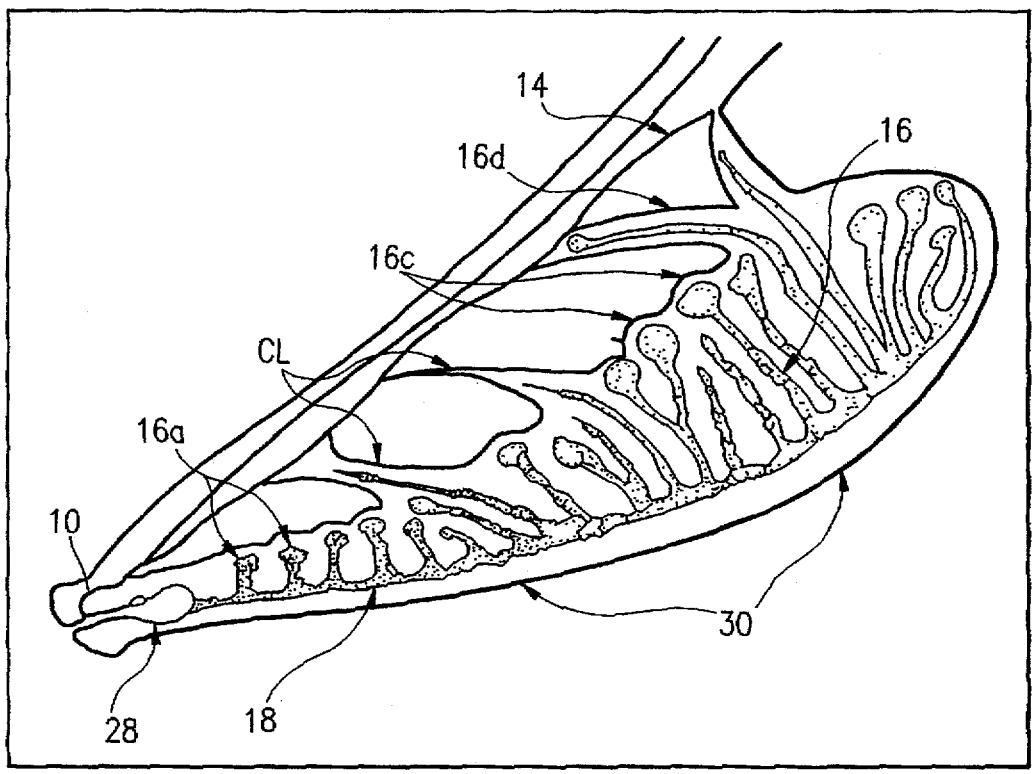

The present invention relates to a method and a computer system for displaying an ultrasound image, sometimes referred to as a sonographic image, for a woman's breast. The technique and system displays the ductal system of the breast such that the technician or physician can readily perceive, locate and evaluate the early stages of breast cancer and more generally the alterations induced in the ductal systems by the specific pathologies of the breast.

Introduction: Ductal Echography - An Anatomically Led Approach to the Breast

Breast cancer is the most frequent cancer among women in developed countries. It is a major problem for oncology and is the most important area of concern in breast investigation. Although 20-year survival rates of over 90% are possible for individuals diagnosed early, half of the women who have breast cancer still die of the disease. It follows from this evidence that the disease is usually detected at a late stage, and that the best measure of the value of a diagnostic method in breast imaging is its ability to achieve early diagnosis rather than its absolute accuracy. Sensitivity or the ability to view potential problem areas is more important than specificity, the ability to absolutely diagnose the disease.

Cancer of the breast is epithelial in origin. It develops in the epithelial or cellular layer that defines the ducts in the breast. Therefore, investigation of the mammary epithelium must be given the highest priority in any diagnostic technique. The mammary epithelium is an extremely thin layer, only one or two cells thick, which lines the ductolobular structures. It is not currently possible to observe and display this 50-μm-thick layer by any physical instrument other than a microscope. Nevertheless, ultrasound imaging, used in a rational way, has shown that even normal, undilated ducts are visible. This has let to a successful method of investigation based on the display of the internal epithelial ductolobular structures of each mammary lobe within the breast.

The basis of this technique is the need to recognize the internal anatomic structures and the relate sonographic imaging with anatomy. This has given as an intelligible anatomic significance to the whole echographic image. The decisive advantage is that the connection between pathological findings and the anatomic structures can be established, thereby defining the relationship between anatomopathology and anatomy in a systematic way. Since this relationship is the basic rational and logical principle that gives scientific value and power to any medical imaging, its application to breast investigation has led to an outstanding advance in the intelligence and efficiency of breast imaging.

Investigation of the Breast

The following preliminary remarks provide the scientific and analytical basis for the breast sonography:

1. Breast cancer is the over-riding consideration that is fundamental to the problem of the investigation of the breast.

2. Early diagnosis of breast cancer is today the only known way to improve long-term survival rates. Thus, diagnostic methods should be evaluated through their capacity for early diagnosis.

3. The breast has three main tissue components. It is a volume of fat in which bags of connective tissue surround networks of hollow pipes lined by extremely thin, one- to two-cell-thick, layer of epithelial tissue.

4. Cancer of the breast arises in the epithelium. Therefore, the investigation of mammary epithelium is a major priority.

5. Only three physical means allow relatively valuable investigations of the breast: X-rays(or mammograms), magnetic resonance imaging (MRI) and ultrasound. Each of these imaging systems have specific insufficiencies which lead to increasing difficulties at earlier and earlier diagnoses.

6. To understand the problems of breast investigations, it is essential to refer to those laws of physics which govern the interactions between the tissues of the breast and the physical means being used for its investigation. These must be clearly understood and their consequences fully appreciated.

Figure 2B:
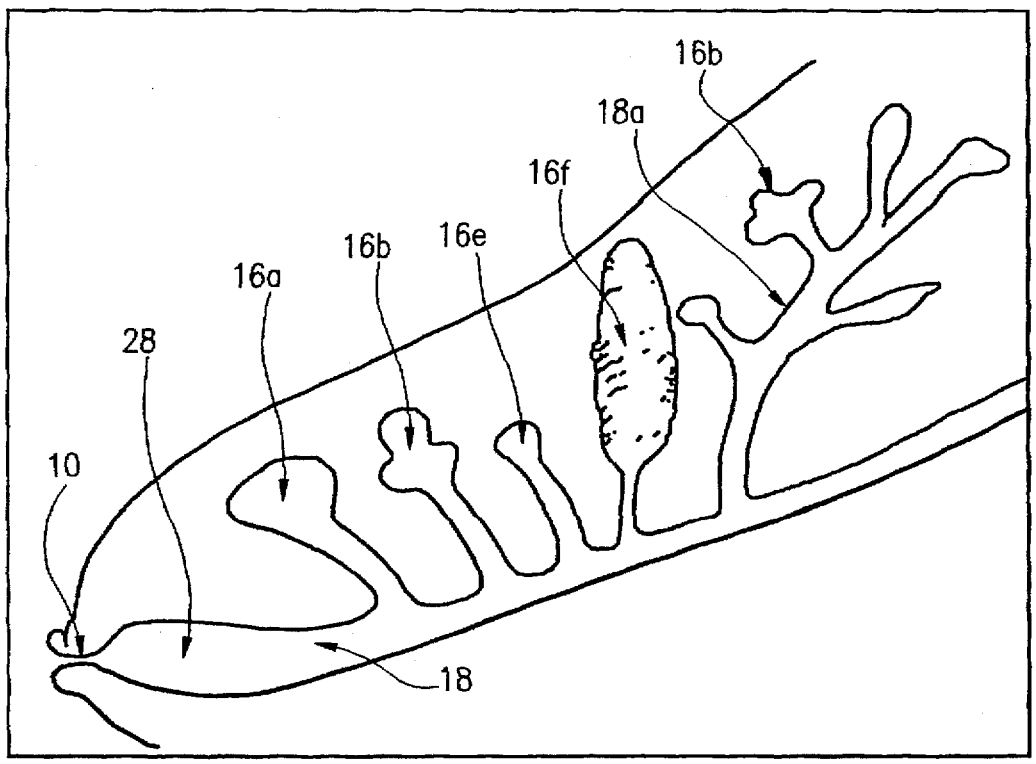

FIGS. 1a–e a show diagrammatic representation of a woman's breast in cross-section, the six (6) major post-prepubertal anatomical stages (FIG. 1c shown two of the most critical stages, the upper half being Stage 2 and the lower half being Stage 3) and a representation of the ductal system (FIGS. 2a and 2b).

General anatomy of the breast: external aspect

The breast is an oval globe or an asymmetrical cone overlying the anterolateral part of the chest with an oblique major axis orientated along the nipple-axillar line. There are three distinct areas: the nipple 10, the areola 12 (around the nipple) and the skin covering the rest of the globe (ellipsoid).

Two significant features should be noted for echographic purposes.

1. The nipple and the areola constitute a thickening of the cutaneous envelope of the breast.

2. The nipple is not situated at the center of the breast but is located in its inner lower third. See FIGS. 1b and 1c.

These features mean that: (a) the nipple and the areola must be investigated separately with different gain settings because there is greater ultrasonic attenuation; and (b) the upper, outer part of the breast requires a scanning procedure that extends out to the periphery and axilla to ensure complete coverage of the glandular tissue. The radically outward scan technique is discussed later. The anatomy of the breast can be considered from three points of view: (a) structurally on a multimeter scale; (b) as imaged by ductal echography; and (c) as imaged by Doppler.

Schematic constitution of the breast

The breast is a modified sweat gland which has developed in the fatty tissue that fills the gap between two layers of the superficial fascia 14: a superficial layer beneath the dermis and a deep layer overlying the muscular fascia and the chest wall. Although these anatomical features are only identified in FIG 1b, these features are shown in FIGS. 1a, 1c, 1d, and 1e.

The schematic structure of the breast consists of the following.

1. A thin envelope resulting from the division of superficial fascia.

2. A fatty tissue that fills the internal space of the envelope and which is made up of a large number of fat cells grouped into a lobular arrangement. At body temperature, breast fat is almost liquid with an oily consistency; thus, this tissue shows an echo-poor sonographic appearance because there are few interferences with the bulk material.

3. A gland that appears as a discoid block called the 'corpus mammae' and which has the following appearance.

(a) Face-on it appears as an ellipse with the nipple at its lower, inner third and its major axis orientated along the 7–1h line (in clockface notation, described later, a line extending from a 7:00 (7h) position through the 1:00 (1h) position wherein reference is made only to the hour hand) for the left breast, and along the 5–11 line (5:00 to 11:00 line) for the right breast.

(b) From a sagittal view it is an asymmetrical cone with the apex plugged into the back of the nipple and a greater development toward the axilla.

(c) Internally, the gland extends from behind the nipple 10, into the fat, radially and obliquely toward the chest wall. Hence, the breast appears to be shaped by three cones inserted into each other: a deep retro-mammary full fatty cone, a hollow medial glandular cone and a hollow superficial fatty cone.

4. The corpus mammae is made up of 15–20 oblong connective bags (which may be visualized on a clockface view as a "daisy" shape with the nipple at the center), the lobes, which extend from the back of the nipple and diverge around the nipple into the fatty tissue like the petals of a faded flower. The connective tissue in the lobes is relatively loose with a frame made of collagen fibers; it appears sensitive to hormone stimulation and can be the site of palpable cyclic nodules that are often the cause of patient referrals.

5. At the axis of each lobe, near the posterior edge, there is a hollow duct. Thus, there are 15–20 hollow ducts diverging from the nipple like the spokes of a wheel. Each duct has a variable number of lateral branches called the lobules 16 (see FIG. 2). Ducts 18 and lobules 16 link 15–20 branching structures called the ductal systems or ductal lobular structure. Cancer of the breast develops in these epithelial ductal systems (90% from the ductal epithelium and 10% from the lobules). As epithelial cells are only found lining the walls of ductal systems, these are areas in which to search for malignant changes.

6. The corpus mammae is anchored to the two layers of the envelope by many connective foils, the Copper's ligaments, which divide up the fat into a spongelike arrangement. It is these ligamentary connections that account for the skin puckering, observed when even deep-seated malignantics develop. The tension on the connective tissue matrix effectively shortens the Cooper's ligaments and distorts the skin line. Throughout this complex sponge-like structure runs a network of nerves and vessels that are arterial, venous and lymphathic.

The notion of a ductal system is important and should be clearly explained. The ductal system is not a concrete anatomic organ constructed by an arrangement of solid material, as are vascular systems. It is a rather more abstract concept, a network bored in the lobe, hollow and theoretical continuation of the air outside the body. This hollow 'milk-pipe' network is lined with epithelium tissue that is a continuation of the skin which folds inside the breast through the pores of the nipple. The epithelium is a thin, one to two-cell layer stuck to a thinner 'basal membrane' which is itself stuck onto myoepithelial cells, loose connective tissue and fat.

Consequently, what appears to be a ductal system is in fact the external surface of the body. As specific breast pathology is epithelial, intramammary lesions are, in reality, external lesions to the body that are trapped in a ductal system, but which are able to invade the body like their skin counterparts (skin carcinomas), with the aggravating circumstance of a long period of occult development, unlike skin carcinomas that are detected early on because they are readily visible.

The missing link in current breast imaging

The reason for the present failure of early diagnosis is the lack of an understanding of the internal anatomy of the breast. It should also be emphasized that the internal anatomic structures of the breast show considerable variation with age for each woman and from one woman to another.

The variation and complexity of the constituents of the sponge-like structure of the breast have prevented the presentation of a simple and unique description of the anatomy of the breast. This in mm prevents the adoption of a single standard for the evaluation of the echographic display. The thorough interpretation of echographic imaging of the lobes and intralobular ductolobular structures, however, requires epithelial features to be identified, among the other internal structures of the breast, at the millimetric scale. There is, therefore, a need to refer to detailed anatomic date which are not available either in books on anatomy or in those dealing with breast investigation. Some pathology books develop interesting anatomic descriptions suitable for research purposes but these are not particularly useful for the interpretation of the individual variations met in every breast.

This lack of anatomic guidance does not allow systematic displays of the internal anatomical structures of the breast by the straightforward direct echographic approach used by sonographers.

It has been found that the relative quantities of the three component tissue types vary from person to person, and change with age in any one individual.

1. Initially, connective tissue is the major component of the breast and represents over 50% of the total organ volume. See FIG. 1a, Stage 0 (Normally for women less then 30 years of age).

2. The percentage of fat increases from about 30% at 30 years to 50% at 50 years and 65% at 75 years. Se the progression of subcutaneous fat in FIGS. 1b, 1c, 1d and 1e.

3. The volume of epithelial cells peaks at the age of 30 years (FIGS. 1a and 1b, stages 0 and 1), when it can be 30% and thereafter it rapidly falls to 10% at 50 years and 55 at 75 years.

This mode of volumetric evaluation of the three main breast tissues shows that the composition of the breast changes markedly with age. However, this mode of volumetric evaluation does not provide any useful information on the precise spatial arrangement of each tissue and hence does not help with a possible accurate echographic investigation of the internal anatomic features of the breast.

Until the advent of ductal echography, all attempts to display the internal features of the breast failed to produce a worthwhile and understandable picture of the anatomy of the breast.

Studies have shown that about 75% of all women diagnosed with breast cancer develop that cancer during stage 2 and stage 3 respectively shown in the upper and lower portions of FIG 1C. FIGS. 1a–e and 2 show superficial facia 14 (sometimes identified in the drawings as "SF"), deep layer 20, areola 12, nipple 10 (sometimes referenced in the drawings as "N"), retro mammary space 22, subcutaneous fat 24, adipose tissue 26, ampulla 28, lobe 30, duct 18, acini 32 and lobule 16.

The instrumental modes of investigation: Mammographic X-rays, MRI and Ultrasound X-ray mammography: the wrong tool to display the wrong tissue in the wrong way.

1. The wrong tool

The laws of physics demonstrate that the characteristics of X-rays are not favorable for the study of large volumes of soft tissue. They have been successfully used for many decades by pathologists to examine thin slices of tissue but as the thickness increases the superposition of shadows and the scatter of X-rays reduces the contrast between tissue types. This was understood at an early stage in the medical use of X-rays. In the 1960's, radiologists were very skeptical about the potential of mammography and 'fine-fingered' surgeons were more than reluctant to concede that it had any value. Since then, physicians have been so impressed by the global view given by mammography, by its superiority over clinical examination and by the speed of the technique, that the basic limitations set by physics have been ignored.

2. Displaying the wrong tissue

The successful use of mammography relies essentially of the lower absorption of the imaging X-rays by fatty tissue. This lower level of absorption provides contrast around the framework of connective tissue that coats the glandular structures. Normal connective tissue shows enough radiodensity for it to be radiologically displayed. Alterations in connective tissue are shown as an increase in density which is easily observed. Hence, X-rays proved an excellent tool for the study of connective pathologies (fibrosis) with high sensitivity and specificity. However, the radiodensity of connective tissue is a major drawback in the dense breast because the mammogram shown a central region of diffuse high density which prevents the radiologist from analyzing breast pathology as epithelial tissue are hidden within.

3. The wrong way

Mammograms do not provide an accurate spatial display of the structures and pathologies of the breast. They are shadowgrams that show a composite image of shadows from the connective structures of the breast and 'foreign bodies' (calcium deposits) superimposed on one another. The shape of the detected alterations does not represent the malignancy itself and the spatial arrangement must be deduced from two or three different projected views. This is difficult to do as witnessed by the complications and difficulties of using stereotaxic techniques.

X-ray computerized tomography (CT) scanners do produce sectional displays but the problems of slice thickness result in poor spatial resolution and the lack of scan-plane flexibility means that imaging the epithelium by following the ducts is almost impossible.

Certain x-ray mammographic techniques do work. These are discussed below.

Fortunately, epithelial diseases induce a connective tissue reaction which changes with time and is perceptible mammographically, using X-ray techniques, through the appearance of a progressive local density. This density, together with the formation of microcalcifications, is the basis of radiodiagnosis. However, these indirect signs, which do not display the epithelial disease itself, only occur after a variable delay, appear progressively and usually only allow specific diagnosis at moderately advanced stages of development. Nevertheless, epithelial diseases can sometimes induce their appearance at an earlier stage. Thus, new, sudden, 'strange', or asymmetrical local increases in density or changes in microcalcifications, can be used to find the occult underlying epithelial lesion responsible for the change.

X-rays do not always work. This is discussed below.

X-rays are not and have never been an adequate means for a satisfactory direct display of breast tissue and their epithelial pathologies. Human intelligence has allowed the serious physical shortcomings of X-rays to be overlooked thereby exploiting an indirect path, through connective density and microcalcification, to epithelial pathology. Notwithstanding these shortcomings, mammography has become, the 'gold standard', for the investigation of the breast.

Secondary signs of the disease are unpredictable with X-ray mammography.

Unfortunately, for the users of X-ray techniques, (both patients and now, more and more frequently, physicians), there are problems associated with the formation of microcalcifications and the connective tissue reaction. The appearance of these indirect signs is unpredictable: they can be missing even in advanced lesions and there is a variable delay between the inception of the epithelial disease and their detection. They cannot immediately be used to assess malignancy as their appearance changes with time-from 'indeterminate' to 'dubious' to 'evocative' before becoming 'specific'.

These unfortunate disparities between the radiological appearances and the pathological situation set limits on the value of X-ray methods for early diagnosis of breast cancer.

The failure of X-ray techniques to solve the problem of early diagnosis of breast cancer has been demonstrated by the low detection rate of early malignance by mammographic screening.

X-ray images taken over a 1 (one) year period are normally used to assess malignance through the progression of the dubious early mammographic signs of the disease. This is an unacceptable delay in the attempt to provide an early diagnosis of breast cancer. Now, the two-tissue techniques allow direct observation of the epithelium and its distinct display from the surrounding connective tissue. 'Two-tissue' techniques available with MRI and ultrasound imaging.

Magnetic Resonance Imaging (sometimes referred to as MRI herein) and ultrasound are each able to display the spatial arrangements of both epithelial and connective tissues, directly and distinctly in sections with good contrast resolution on the acquired and displayed image. Ultrasound has the additional advantage of facilitating direct manual manipulation of the breast during the examination so that long sections of ducts can be 'straightened' and imaged on a single scan.

MRI imaging of the breast.

MRI, while being improved technologically, currently shows good cancer detection capability especially when used with contrast media. Its spatial resolution, however, remains quite insufficient to compete with ductal echography (the technique described herein) as MRI is not able to resolve normal ducts. Improvements in resolution are needed to enable early diagnosis to be made of breast cancer. The decisive advantageous of the ducal echography (DE).

More than 6000 women were examined in a multi-year patient study. Many of them were examined repeatedly for follow-up purposes. Through these examinations it was observed, constantly and convincingly, that ductal echography is decisively superior to X-ray mammography for the detection and imaging display of early and moderately advanced breast pathologies. The images in the book entitled "Atlas of Ultrasound and Ductal Echography of the Breast" by M. Teboul and M. Halliwell, published June, 1995, provide the evidence for this assertion. The reasons for the superiority of ductal echography can be found in the laws of physics. (In the following analysis numerical values are approximate.)

Certain laws govern the interaction between matter and X-rays

X-rays are influenced by the atomic make-up of tissues. They are not influenced by the physical state, i.e. whether the matter is gas, liquid, semiliquid or solid.

Attenuation of X-rays, depends on the third power of the atomic mass and the fourth power of the atomic number of the atomic constituents of tissues. Consequently, this technique is very sensitive to small differences in the average atomic composition of tissues. By comparison, attenuation depends only linearly on the specimen's thickness and 'compactness' (here the word "compactness" is used in preference to the correct term 'density' to avoid confusion with 'density' as applied to the mammographic image). Small changes in thickness or compactness only produce small changes in the image.

It can be shown that the composition of the breast can be divided, as far as X-rays are concerned, into fat and 'other organic components'. The 'other organic components' are: connective tissue, epithelial tissue (see FIGS. 1a–1e), secretions (organic fluids, cells and cellular debris) in the ductolobular structures, and blood. Under normal conditions these non-fat components are roughly 80% water and 20% organic material. Water is 10% hydrogen and 90% oxygen and its atomic mass is usually taken as a given reference level (solid/liquid volumic mass=1). The organic matter can be taken to be approximately water-equivalent because its average atomic constitution is 10% hydrogen, 12% carbon, 77% of either nitrogen or oxygen (nitrogen (7) and oxygen (8) are practically interchangeable for this analysis) and 1% other elements. Thus, those parts of the breast that are not fat can be taken to be water-equivalent.

Fat contains 12% hydrogen, 12% of either nitrogen or oxygen and 76% carbon. This high percentage of carbon (6) restfits in a smaller average volumic mass of 0.9, i.e., it has an average atomic mass which is less than that of the 'other organic components' per unit volume (they are at similar conditions of temperature and pressure).

The slight difference in volumic atomic mass enables mammography to differentiate between the fat and the water-equivalent 'other organic components' and this is responsible for the success of mammography.

However, the difference in volumetric atomic mass between the individual tissues comprising the other organic components is too small to allow differentiation. The presence within and between them of intermixed fat is so variable and unpredictable that rational analysis of the mammogram is not possible.

The laws governing the interaction between matter and ultrasound are different.

Ultrasound is very sensitive to the physical state (solid, liquid or gas) and mechanical properties of matter; the elasticity and 'compactness', for example, determine the percentage reflection at boundaries. The shape and size of the boundary surface give rise to specular or scattered reflection; relative movements of matter produce changes in reflected frequency (Doppler shift). (FIGS. 9c and 9d)

The connective tissue is described as 'loose' but is made of solid collagenous fibers and behaves as a corporal solid body, well delineated by ultrasound from the semiliquid (at body temperature) breast fat on one side and the liquid (organic secretions) containing ductolobular structures on the other.

The differentiation means that ultrasound is able to display the spatial arrangement of the fluid that fills the ductolobular structures and hence reveals the contours of the ducts. These contours contain the one- to two-cell thick lining of the epithelium which is critical to the early detection of breast cancer. Although this layer of epithelial cells is too thin to be directly visible, its spatial arrangement can be observed because it is the interface which corresponds to the silhouette of the contours of the liquid or gel content of the ductolobular structures. The existence of occult epithelial diseases is apparent as soon as a perceptible alteration in the echographic shape or shade of the ductolobular structures is produced. Moreover, when the epithelium increases in thickness it becomes easily observable and clearly distinguishable from the connective tissue because it happens to show a lower echogenicity. It is a gel. When these two tissues are affected more intensely by pathologies, their difference in echogenicity increases allowing the visually perceivable differentiation between epithelial and connective components in lesions.

These features explain why the normal ductal structures can always be seen and why ultrasound is sensitive to early alterations in these physical structures.

X-ray mammography versus ultrasound mammography is discussed below.

Occasionally, it is possible to perceive the transparency of early and moderately advanced epithelial disease (while it is still radiotransparent and the connective tissue is not significantly affected and still slightly radiodense) through its slightly more dense connective envelope. These conditions have allowed X-ray mammographic recognition of lobules and their ductolobular terminal units (DLTUs) in moderate adenoses, the perception of transparent dilatation and filling of a duct by a malignancy (seen as transparent medial band bordered by a dense parallel double band which represents the projection of the malignancy in its connective envelope) and, rarely, the recognition of the three-layer rounded in malignant foci (see the surrounding fibrosis and internal fibrosis in FIG. 11a).

Figure 5A:
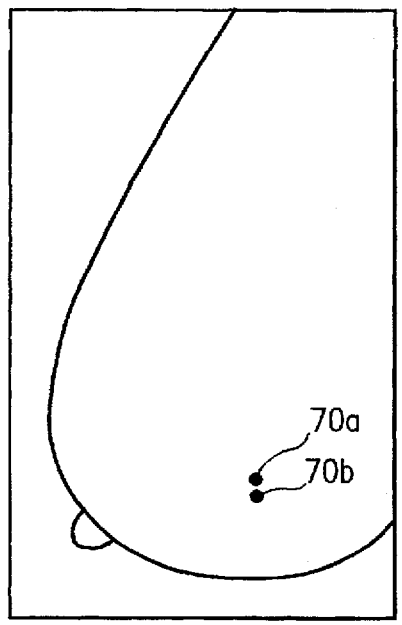
FIGS. 5a, 5b and 5c show DE diagnosis of an MBC (Minimal Breast Cancer) from two microcalcifications detected via x-ray mammography.
Figure 5B:
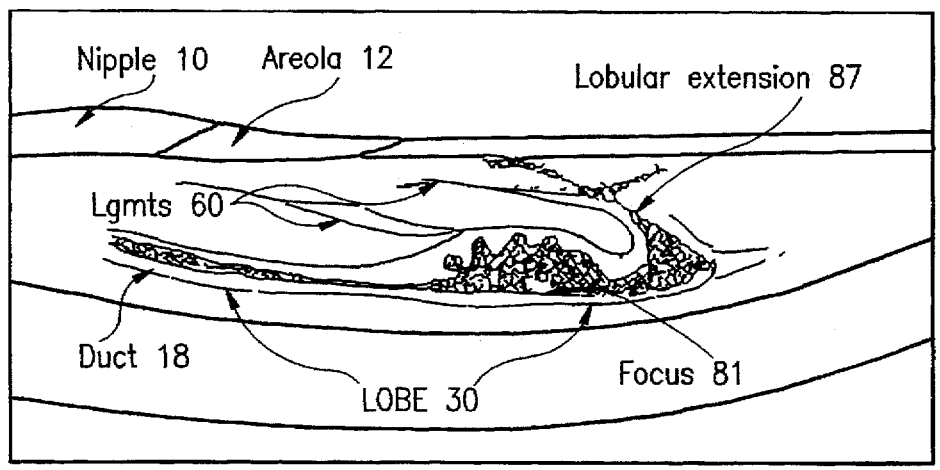
Figure 5C:
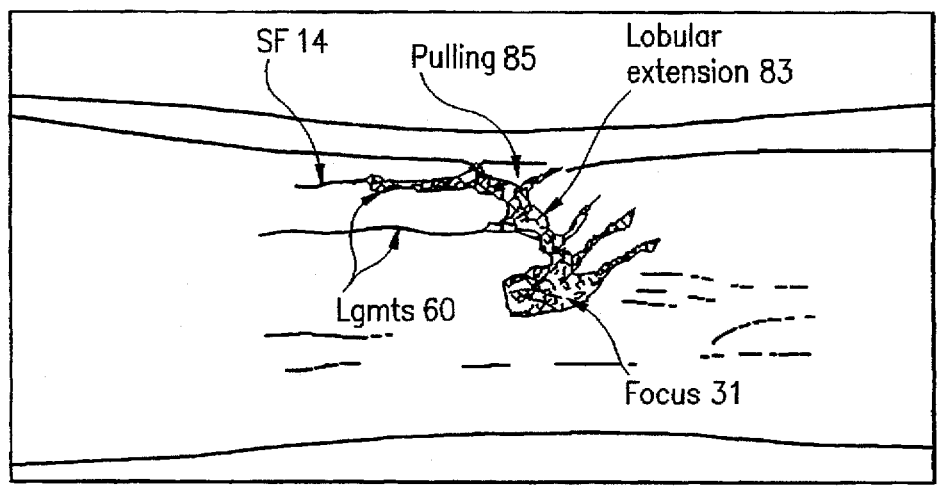

These rare X-ray mammographic findings can be directly compared with those revealed by echography and help to confirm the validity of the ultrasonic method (see FIGS. 5b and 5c). However, the main advantage of ultrasound is that these ductal displays are always visible, while, on the X-ray mammogram, X-rays usually do not show the epithelium and ductolobular content. The ductal system and the epithelium remain hidden in and hidden by the connective tissue envelope.

Malignancies are not visible in X-ray mammograms until they have produced microcalcifications or have induced a stromal reaction. (FIG. 5a diagrammatically shows a microcalcification found by an X-ray). These increase the thickness or 'compactness' of the connective tissue sufficiently and steeply enough to become distinguishable among the surrounding variable densities of the affected lobe and of the adjacent lobes.

X-ray techniques do not provide a convenient picture of the epithelium because this tissue has very similar atomic characteristics to other structures (and therefore image contrast is poor), because the complex, interlaced nature of the ductolobular structures is made more complicated by their superimposed projection onto the film and because scattering of X-rays reduces the clarity of tomographic techniques (CT scanners). X-rays are basically shadow grams. X-rays do not detect different cancers at similar developmental stages by secondary signs because microcalcification is a variable phenomenon and because an increase in connective tissue density depends both on the type of cancer (which will alter the time of development) and the absolute change in actual tissue density, which will affect its mammographic visibility. Densities will remain difficult to evaluate for some time.

In spite of these drawbacks, X-ray mammography is the first examination to be performed on an individual for screening and detection because it is rapid and will detect or suggest many malignancies. Any non-specific or incomplete sets of mammographic signs can be subsequently subjected to ductal echographic analysis for detailed elucidation.

Anatomy of the Breast

The missing link in conventional breast imaging: is the systematic correspondence with anatomy. The current method of diagnosing breast pathologies is flawed.

A competent sonographer will not describe the strong shadowing echo of a stone detected below the liver without determining its relationship to the biliary tract and without evaluating the state of the biliary system. A surgeon will not operate without first having received this information.

In cancer of the breast, surgeons and their team of oncologists will ask for a comprehensive analysis: exhaustive blood test, lung radiography, liver echography, chemical markers and even isotopic bone scans. Physicians thus try to evaluate the lesion in relation to the patient's whole-body environment. However, although they are well aware of the possible developments of the malignancy in multiple sites, in the ductolobular structure of origin or elsewhere, physicians do not demand an echographic examination of the environment upstream, around and downstream of the malignancy (and in the epithelial structures of the other lobes). This omission does not arise because such investigations are considered useless. Indeed, echography is a typical baseline examination prescribed for cancers in soft tissues and the evidence of recurrences that have developed in the remaining ductolobular structures, just a few months after surgery, is sufficiently explicit to confirm the importance of echographic examination in the treatment of breast cancer.

At first sight, the reason for the omission appears to be obvious and is simple. The information is not requested because sonography is not currently considered a valid method of examination. This deduction is based on observations of the inefficiencies of conventional echography which have resulted in such a deep contempt for the use of ultrasound that this physical means is still often not mentioned in management and protocols today.

In reality, this omission dates back to before the introduction of ultrasound. Indeed, if the deficiency of ultrasound was specifically involved, another examination would be prescribed. Surprising as it may seem, not only do surgeons not ask for this information before surgery today, but they have never asked for it in the past for breast cancer. Until now, assessments of affected ductolobular structures have always been performed after surgery, through postsurgical anatomopathological investigations. There are two reasons, one physical and the other conceptual, why such important information has been neglected.

The physical reason for the flaw is discussed below.

Prior to the ductal echography techniques discussed in conjunction with the invention herein, no other means of breast imaging was able to display the ductolobular structures, the epithelium lining their wails and the epithelial alterations that develop in them. This deficiency is linked to the inadequacies of previous imaging techniques. Therefore, the neglect does not only result from the failure of conventional ultrasound echography; it also involves the deficiencies of x-ray mammography, which has been used for 30 years.

X-ray mammography does not display the radiotransparent epithelium, hidden in and by its more radio-opaque connective envelope.

Conventional ultrasound echography does not take into consideration the anatomic arrangement of epithelial structure.

Figure 3:
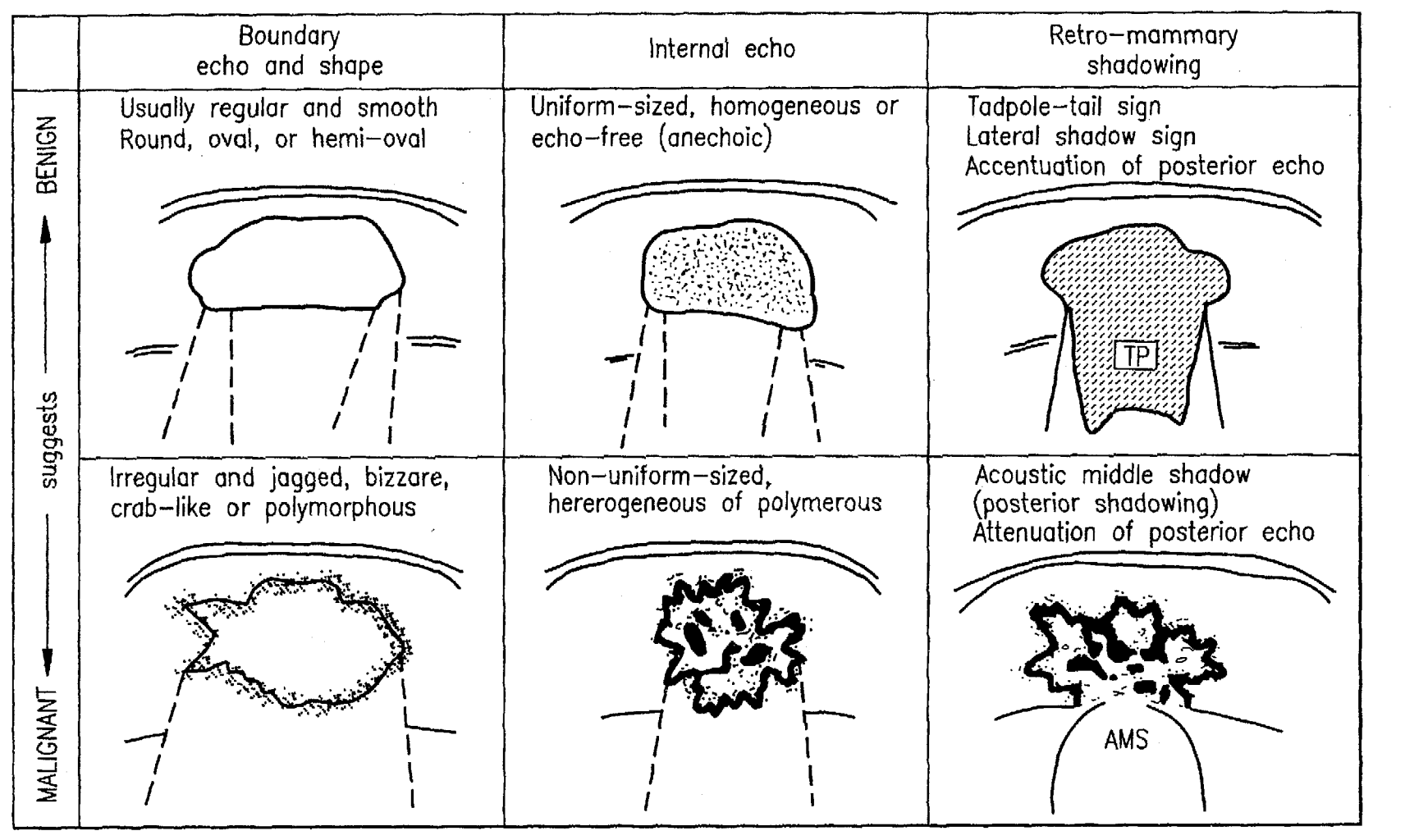

FIG. 3 is a chart which shows conventional echographic criteria of breast malignancies.

The classical criteria of malignancy used in conventional ultrasound echography are based upon succinct "geometrical" concepts (geometrical aspect of shape, shade, boundaries, uniformity and shadowing). See "Ultrasonic Diagnosis of Breast Cancer" 1 Ultrasound in Medicine and Biology, pp. 383–391, by T. Kobayashi (1975). They are limited to the geometrical analysis of an abnormality in an otherwise randomly scanned and meaningless echographic field. This results in the impossibility to fulfil the fundamental mandatory requirement of the scientific precept that ought to rule any imaging technique; the absolute necessity to relate the image to anatomy and anatomopathology.

The top three panels in FIG. 3 show, from left to right, boundary echo and shape (usually regular and smooth, round, oval or hemi-spherical oval); internal echo (uniform-sized, homogenous or echo-free (anechoic); and retromammary shadowing (tadpole-tail (herein TP) sign, lateral shadow sign, accentuation of posterior echo). The top diagrammatic echographic images, as per conventional ultrasonic echographic teachings, suggest benign conditions. The lower three panels in FIG. 3 show geometric shapes and images suggesting malignant conditions. From left to right these images per the boundary, internal echo and retromammary conditions (top bar labels) show (a) irregular and jagged, bizarre, crab-like or polymorphous scan images; (b) non-uniform sized, heterogeneous or polymerous images; and (c) acoustic middle shadow (herein AMS) (posterior shadowing) or attenuation of posterior echo.

It is therefore, impossible for both of these techniques (x-ray mammography and conventional ultrasonic or imaging echography) to identify ductolobular structures and consequently any early epithelial alterations that occur within them.

The following discursion addresses the effect on the current method of early diagnosis.

Owing to the deficiency common to both techniques, it follows that the anatomic structure in which the malignancy develops is not recognized by the present modes of diagnosis. Moreover, anatomic evaluation is not considered as an improvement nor even important, and it is not even mentioned in most protocols of breast investigation. This strange omission is observed at all levels in the approach to the breast.

One might understand that such a defect in the management of diagnosis must be tolerated because of the necessity to use data from mammography despite its inability to provide a worthwhile display of the anatomic arrangement of ductolobular structures. There is no longer a need, however, to admit to this defect because ultrasound is able to display these structures.

This situation would certainly not have been tolerated if it had not already been accepted for mammography. Such neglect in the management of diagnosis would never be allowed with the ultrasonic investigation of any other organ of the body. No professional sonographer would dare to evaluate a kidney, thyroid or uterus without an understanding of the anatomy of the organ concerned.

Yet this is how the breast is still investigated and any attempt to modify this approach and to consider anatomy is met with reluctance. This means that the deficiencies of present methods and the failures of early diagnosis are not acknowledged nor fully appreciated. Given the poor results of current early diagnosis, one can only continue to wonder why the use of anatomy should be met with such great disapproval during diagnosis when the rationale for its inclusion is indisputable. Consequently, the fundamental reason for its exclusion must be sought at a higher level in the diagnostic approach.

The conceptual reason for the flaw is discussed below.

The lack of evidence for the internal anatomic features of the breast means that the structure of origin (and hence the epithelial malignancy, which develops within it) cannot be displayed accurately by present conventional imaging (whether x-ray or conventional ultrasound) techniques. In order, therefore, to perform their diagnoses, physicians are compelled to use associated indirect signs of mammography that they cannot link to anatomy or anatomopathology as these imaging techniques do not display the structure in which the malignancy develops. Hence, physicians are not only obliged to look for indirect signs, but moreover they also have to evaluate those images based on their geometrical appearance and not on their anatomopathological significance.

This mode of diagnosis, based on the probability of imaging appearance (see FIG. 3), is empirical and deduced from previous observations. Experience shows, unfortunately, that the reliability of this method decreases with the immaturity of lesions, with a parallel decrease in the efficiency of the techniques. Thus, current imaging techniques cannot fulfill the conditions required to form a reliable means of early diagnosis.

This deficiency in the elaboration of diagnosis constitutes the fundamental problem in the breast investigation today because it reveals an underlying concept that has extremely gave repercussions on the reliability of diagnosis. It has led to the basic scientific precept, which ought to rule all diagnostic imaging, being abandoned: the necessity for a systematic correspondence between imaging, anatomy and anatomopathology. This correspondence is the only way to understand, in detail, the precise significance of the different constituents of the image and, globally, the general meaning of the whole imaging field. It is the only rational way to evaluate lesions with and within their structures of origin. It is this correspondence between anatomical structure and the imaging protocol which gives diagnosis by ductal imaging superiority over other imaging techniques.

Indeed, this significant advance in diagnostic potential is specific to ductal imaging. The addition of supplementary linear or punctiform details to the conventional image cannot, by itself, have such a beneficial effect. The intervention of a new factor is required in order to achieve an improvement in the interpretation of the image. This important advance in understanding requires two factors: (a) an improvement in the display of the image (more detail, better drawing or better presentation of elements); and, (b) an appreciation of the significance of the image which results in a major transformation in the interpretation (an increase in the possibilities of evaluating the different elements, recognition of new elements or new combinations of element, and/or identification of patterns that give new significance to the image).

The perception of the ductolobular structures (FIGS. 1a–1e and 2a and 2b) changes the intelligibility of the image. It assigns an anatomic significance to the whole echographic field (hence the link between imaging and anatomy) and allows the recognition of alterations in anatomic structures (hence the link between anatomy and anatomopathology). Thus, the superiority of ductal echography (described herein in conjunction with the present invention) as a method for evaluating malignancies is not fortuitous: it is due to the improved interpretive possibilities which result from the difference between the concepts that govern the two diagnostic modes, i.e., the use of anatomy in ductal echography and its disregard in mammography and conventional echographic techniques.

1. In the conventional mode of diagnosis, mammography and conventional echography is required to provide evidence of a 'tumor' or, failing that a 'tumoral zone'. It is the concept of 'malignant tumor' which guides the investigation.

2. In the ductal echographic mode of diagnosis, ductal echography is required to provide evidence of the existence of an alteration of the ductolobular structures. It is the concept of 'malignant disease of the epithelium of a ductolobular structure' which guides the investigation.

An earlier and more accurate diagnosis becomes possible with ductal echography because the 'malignant disease of the epithelium of the ductolobular structure' has been evolving for several years before the 'formation of the moral mass'. Ductal echography has the technical and physical ability to visualize both normal and pathological ductolobular structures, it follows that this technique is well able to provide information during the period which precedes the 'formation of the mass'.

This explains the failure of the prior art approach to early diagnosis and allows one to hope for a significant advance in early diagnosis through the echography visualization of the ductolobular structures. This advance will be consolidated as echographic imaging improves with advances in technology.

A new philosophy for the approach to early diagnosis of breast cancer

The adoption of a tumoral concept for breast cancer does not deny the systemic character of the disease. Therefore, the conventional mode of diagnosis calls for a simultaneous evaluation of the 'tumor' and a general check-up. Between the concept of 'tumor' and the concept of 'systemic disease' there is a 'missing link': the concept of 'malignant disease of the epithelium of the ductolobular structure. The insertion of this missing link into the elaboration of the diagnosis is translated as follows:

a) in terms of concept as a triple approach (ductolobular, tumoral and systemic):

b) in diagnosis as the evaluation of the ductolobular structure;

c) in imaging as the display of these structures;

d) in technical modality as the use of a method allowing this display (e.g. echography).

The imaging as the display of these ductal systems is the thrust of the present invention described herein.

The superiority of ductal imaging questions the concept of cancer of the breast, with the implication that the present failure of early diagnosis could be a consequence of the limitation of the concept of malignance to the notion of 'tumor'. Indeed, early diagnosis does not appear to be compatible with the 'tumoral' concept because this notion presupposes waiting until the 'formation of the mass'.

Without an 'organized' tumor, there is no possible direct reliable diagnosis. This is effectively what experience shows: multicentimetric diffuse malignancies remain undiagnosed for a long period of time, clinically and mammographically, because they do not exhibit 'tumoral' characteristics. Ductal echography displays diffuse malignancies distinctly and clearly shows focal malignant 'coalescent masses' as small as 0.5 cm in size.

Access to early diagnosis of breast cancer presumes the notion of malignant disease of the ductolobular system, which implies the necessary use of physical means to allow observation and evaluation, visually and cytologically, of the ductolobular structures; hence, the display of the internal anatomy of mammary lobes which is the link missing from other modes of breast imaging.

Ductal echographic access to the internal anatomy of the breast

The characteristics of breast structures are highly variable with the age of each women (see FIGS 1a–1e) and from one woman to another and the display of intralobar structures seems at first to be so complicated and in such disarray that previous echographic imaging techniques have failed to identify the internal anatomic features in every breast.

To overcome this extreme complexity and variability in the anatomy of the breast, it was decided to reverse the problem. In an attempt to distinguish systematically between the anatomic structures and the components of the image, it appeared to be more logical to perform a comparative study by proceeding from the simple shapes towards the more complex. As the internal structures show a progressive simplification with time (compare the progression from Stage 5, FIG. 1e to Stage 1, FIG. 1b), due to the involution process of the breast, it was decided to evaluate their mode of variation with time by starting with their disappearance at stage 5 and by tracing back their variations with age, i.e., by reversing the involution process of the breast. The aim was to identify and separate the elements that could be considered to be permanent from those that are less so. This information could then be used to establish a possible schematic mode of progression of involution of the breast with time. This new approach has proved to be a successful research path and has led to important and interesting discoveries.

Ductal echography of the real anatomy of the breast: Stages of involution of the breast Involution of the breast leads, with time, to the complete disappearance of lobar structures and to fully fatty transformation. This process determines with age the variations in the lobes (in shape and size), in the files of lobules (in number and spatial orientation) and in the lobules (in size and number in the files). The involution of the breast occurs during the period of a woman's lie that encompasses the means age period of breast cancer formation. It shows a direct correspondence with the formation and early development of cancer of the breast.

The involution process should therefore be taken into serious consideration during examinations and calls for a detailed understanding of breast anatomy.

The comparative observation of the involution process has led to the lobe being chosen as the main feature for evaluation of stages of involution, and has shown that two zones in the lobe differ completely with regard to involution.

1. The deep medial part of the lobe (duct and periductal sheath) and the deep zone of the breast, which do not show perceptible changes until the final stages of involution.

2. The lobules ( with the lateral and superficial parts of the lobe) and the superficial part of the breast, which show important variations that must be recognized in order to understand breast imaging. This sequence of events is outlined below.

The more permanent features
The duct, the deep medial part of lobe and the deep part of the breast Behind the body of the lobes, from the chest towards the skin, the thickening of the posterior fatty layer is fairly uniform, the posterior edge of the lobe shows an almost linear contour line, and the duct appears linear and runs above, close to and parallel with the posterior edge. Except for a slow uniform growth of the deep fatty layer, the process of involution does not induce any important changes to the pattern of the ductal zone and the deep part of the breast until the lobe has complete disappeared and there is full fatty transformation of the breast.

The more variable features
The lobules, the anterior and lateral parts of the lobe and the superficial part of the breast The lobe appears to be the most useful feature by which to evaluate involution. The comparative observation of the transformation of its echographic appearance has proved to be a most successful means of analysis.

The shape of the lobes and their reciprocal relationship is highly variable and depends:

1. for all lobes in both breasts, on the general state of involution of the breast, which is determined by the physiological age of the mammary glands;

2. for each lobe individually in a breast (fair symmetry is usually observed between the breasts), on the severity of the local involution, which is conditioned by the position of the lobe within the clockface arrangement of lobes around the nipple;

3. and for each portion in a lobe, on the position of the segment with regard to the insertions of the supperficial Cooper's Ligaments into the superficial edge of the lobe.

Six stages have been distinguished

One state of full glandular development, stage 0, and five stages of involution designated from stages 1 to 5, in increasing order of involution.

Studies have shown that about 75% of all women diagnosed with breast cancer develop that cancer during stage 2 and stage 3 respectively shown in the upper and lower portions of FIG. 1c. FIGS. 1a–e and 2 show superficial facia 14 (sometimes identified in the drawings as "SF"), deep layer 20, areola 12, nipple 10 (sometimes referenced in the drawings as "N"), retro mammary space 22, subcutaneous fat 24, adipose tissue 26, ampulla 28, lobe 30, duct 18, acini 32 and lobule 16.

An understanding of the anatomy leads the way to early diagnosos

At the early stage of macroscopic development, malignancies have not yet formed a conspicuous 'tumor' or the tumoral symptomatology is insufficient to provide reliable radiological signs. At this stage, the malignant disease of the epithelium has already been evolving for many years. The carcinogenic process has affected ductolobular and ligamentary features and is easily demonstrated. There are very extended signs (because induced alterations in the elasticity modify the acoustic properties of ligaments and because the reaction of the adjacent connective tissue produces a hyperechogenicity which is easily perceived as its contrast is exaggerated by the increased hypoechogenicity of malignant epithelium). These echographic signs are detectable before the stage of development needed for the radiological density to increase sufficiently and steeply enough to be identified on the mammogram. The grouping of these echographic signs displays a symptomatology, the ligamentary part of which has already been recognized by conventional and water-path sonography. They have been designated secondary or 'indrect' signs because these techniques have only been able directly to investigate advanced malignancies where the 'formation of the mass' produces a predominantly moral 'symptomatology'.

In early lesions, an inversion is observed in the relative importance of the two direct and indirect symptomatologies. The ductolobular and ligamentary inversion, which is well demonstrated by water-path echography, was reported in the early 1980s (Teboul, 1982, 1985 "L'echographie Mammarie en 1982" in Actualities Ultrasonographiques, p. 17, Euromed ed.; and "The detection of small breast cancers" in Proceedings of the 4th International Congress on the Ultrasonic Examination of the Breast, pp. 91–99, Witton Press, respectively). Ductal echographic symptomatology, based on anatomy, shows considerable advantages.

1. It is linked to the ductolobular and ligamentary anatomy. By using a technique of investigation based upon these structures, it becomes easily detectable.

2. It is constant because it also visualizes the epithelial malignancy.

3. It is early and precedes the appearance of tumoral signs (since it provides evidence for the existence of the malignant disease at the origin of the tumor).

4. It is permanent (it persists and adds its signs to those of the 'formation of the mass': however, its relative importance decreases as the tumoral syndrome develops and becomes predominant).

5. It is detectable early (at stages when other tissues are still supple enough to allow a free demonstration of the alterations in elasticity that specifically affect the local ligamentary structures).

6. It is easily perceived because it is very extended (alterations in elasticity modify ligamentary reflections over several centimeters at stages where the largest perceptible coalescent zones epithelial malignancy are still only 0.5 cm in size).

7. It shows an accurate anatomopathological display (it shows the epithelial component with its zone of coalescence and its extensions into the lobar and ligamentary ductolobular structures).

8. It provides specific information (it visualizes distinctly the primary epithelial disease from the associated secondary connective reaction, allowing them to be differentiated).

9. It fulfills a dual warning and guiding role for a double visual and interventional evaluation (extended indirect signs and anatomical structures allow one to locate the best zones of early coalescence of malignancy, which allows earlier and more efficient echo-guided microsampling.

10. It has become more reliable (because it is now linked to the ductolobular anatomy and because its accuracy is systematically assessed by echo-guided microsampling).

11. It can be used immediately (however, current two-dimensional ultrasound imaging is operator-dependent and requires appropriate training for the sonographer).

12. It should become less operator-dependent in the near future owing to the development of transparent three-dimensional processing of the image.

13. It must be studied and understood in its present two-dimensional mode of display (because the duct remains the most important feature and because the selected two-dimensional scans should correspond to the most interesting planes of the three-dimensional image; therefore, the data for interpretation remain the same).

14. It provides the 'missing link' which completes the logical chain of procedures for the approach to cancer of the breast (thereby showing the advantages of widening the present approach).

FIG. 2a shows a schematic anatomy of the mammary lobe that plugs into the back side of the nipple 10. The proximal lobules 16a near the nipple are bigger than the others 16b. Some lobules 16e exceed the average size of the lobe 30 and swell the anterior lobe contour, which may then show a scalloped pattern. Some lobules extend into superficial Cooper's ligaments CL which stick to the superficial layer of the superficial fascia 14 (SF).

FIG. 2b shows a schematic anatomy of the ductolobular system: nipple 10; ampulla 28; duct 18: the most frequent types of individual lobules 16; big lobule 16a near the nipple; normal lobule 16b; a clover-leaf shape formation at their extremity; the ductolobular terminal units of Wellings (complex DLTU gather acini and ductules). DLTUs are the milk-producing units. Lobules usually emerge from all over the surface of the superficial half side of the duct and should grown along the duct and towards the skin, thus in directions that are well displayed by skin-contact sonography.

Ductal echographic access to early diagnosis of breast malignancy Involution and cancer The 'suspension-bridge' and associated 'duct-ligamentary' patterns are discussed below.

During the period when breast cancer detection becomes increasingly important, i.e. after 35 years of age, (FIG. 1c), the normal involutionary processes within the breast can be observed on longitudinal scans from the nipple, radially outward along generally clockface projections (e.g., at 12:00, 1:00, 2:00 . . . 11:00 longitudinal-radial scans). It has been shown that fatty involution of the lobe tends to display the typical 'suspension bridge' pattern (upper lobe, FIG. 1c) in which the duct 40 and the posterior edge symbolize the roadway, the superficial Cooper's ligaments 42 display the pylons, the superficial edge 44 of the lobe represents the main suspension cable and the lobules 46 feature the suspending rods that join the suspension cable to the roadway.

However, the particular form that this 'suspension-bridge' pattern takes is dependent on the anatomic arrangement of the superficial ligaments and the orientation of the lobules. The anatomic arrangement alters the pattern because the pylons and suspending rods are not always perpendicular to the skin; they can be tilted or oblique to the surface of the skin. The 'suspending rods' are not always parallel to each other and to the superficial Cooper' s ligaments. Nevertheless, whatever precise shape these structures may exhibit, the 'suspension-bridge' pattern provides a clear image of the connective envelope around the remaining epithelial tissue.

In addition, the pattern of the 'residual state' of this 'suspension bridge' depends on the degree of involution of the lobe and is a valuable indicator of the stage of involution. Compare Stage 2 to Stage 3 in FIG. 1c and further to Stage 4 in FIG. 1d. During involution, the convex half-leaf-like pattern (Stage 1, FIG. 1b) of the ductal-axial longitudinal section of the young (non-involuted) lobe, (Stage 1), evolves into the concave 'suspension bridge' (Stage 2), that gradually also loses its features, always in the same order. First, the suspension rods disappear, and then the main suspension cable evolves from a parabola into a double-angulated line delineated by a duct and two Cooper's ligaments, to produce a scabbard pattern. (Stage 3). Later, the pylons fade (bare-thread pattern) (Stage 4, FIG. 1d), and finally the road vanishes (full fatty involution) (Stage 5, FIG. 1e)). Thus, during this period of increased cancer detection, the 'suspension-bridge' pattern continuously evolves, gradually progressing towards a simpler pattern. First, the residual periductal connective sheath and the remaining superficial Copper's ligaments are found together in the ductoligamentary scabbard pattern, which decays eventually to leave a 'coated-thread' displayed by the sole remaining duct; then a bare-thread pattern appears with a very thin connective coating. Finally, the 'road' disappears (Stage 5) and the full transformation of the breast into fat is completed.

By studying this involutionary process, one is able to identify the residual epithelial formations by observing their conspicuous connective tissue coating at any stage of the involution, despite the considerable changes that occur in the lobe. Ductal echography is thus a viable echographic means to localize and evaluate these epithelial layers and consequently to detect alterations to them.

1. If the 'suspension-bridge' and associated patterns do really describe the persistent two-cell epithelial layer, then a ductal echographic display of malignancies should match these patterns. This is exactly what experience has demonstrated and what can be consistently observed in the illustrations of the more than 300 malignant entities presented in the book by M. Teboul and M. Halliwell (1995) identified earlier herein.

2. Furthermore, if the 'suspension-bridge' and associated 'ductoligamentary' patterns are real then, by observing these patterns in involuted lobes and reversing the logical line of reasoning, the observer should be able to deduce the locality of the preferred sites of early growth of cancer. Cancers develop in the epithelial cells; thus, the preferential mode of development of malignant extensions, in and along the associated residual structures of the breast, can be predicted. This is exactly what ductal echography enables the physician to do.

Using a scanning mode centered by and directed towards the duct, the arrangement of ductolobular structures appears to be determined by the duct, and the shape of the lobules (see lobules 16 in FIG. 2) appears to be dictated by the superficial Cooper's ligaments. The whole echographic field acquires an anatomic significance. The image becomes understandable and allows one to make a direct evaluation of the anatomy and specific pathologies of the breast, including any malignancies that are visually discernable by ultrasound echography at early and/or moderately advanced stages provided the malignantics are more then 2–4 mm in size.

For the first time, a non-invasive method of investigation of the breast has the ability to display, in the lobe and its ligamentary structures, the essential features that allow observation of breast cancer at early and moderately advanced stages. The images produced also allow one to draw a mental reconstruction of the form of the lesion. This ability to produce a visual appreciation of the development of breast malignancy is the logical consequence of the basic theories behind the concept of ductal echography. As the basis of this method is to display the anatomophysiopathological axis of the lobe, it is reasonable to expect the technique to demonstrate the preferred zones of formation and preferential modes of development of cancer.

The failure of previous ultrasonic echographic techniques

The ultrasonic investigation of the breast raises two questions.

1. What is the object of the investigation? The answer is simple: to assess diseases of the breast through evaluation of the alterations the diseases induce in the tissues of the breast.

2. What is the best method to reach that goal? The answer is not so simple and depends on the characteristics of breast anatomy and breast pathologies.

There are four compelling characteristics of the breast which determine the conditions to be fulfilled for a successful investigation.

1. The important pathology of the breast is epithelial. Consequently, breast epithelium must be displayed.

2. Mammary epithelium lines the ductal systems in mammary lobes. The ductal system must be shown.

3. Ductal systems are made of ducts and lobules which are hollow tubes. Hollow tubes must be displayed longitudinally for the best analysis, which implies that the imaging transducer must be positioned so as to image along the axes of the ducts and lobes.

4. Ductal systems converge toward the nipple in a radial arrangement with slight individual variations. The mode of scanning must have a flexible radial approach to select the optimum individual scanning planes.

To date, conventional ultrasonography has failed to achieve or display these features of the breast. It has not been used to investigate the breast as effectively as it can and has not become a major means of investigation because these conditions have not been fully appreciated and exploited. In conventional echography, the transducer is usually placed more or less randomly on the skin in a sagittal or transverse plane and then moved so as to produce a linear sweep of scans perpendicular to the echographic field. Obviously, linear sweeps do not match the radial anatomy of the breast. Lobes and ductal systems are scanned at variable orientations and the epithelium is displayed most often in the cross-section, appearing as scattered echo-poor dots; in waterpath echography, equipment was developed to perform automated rotating radial scanning. However, breast ducts are not geometrically radial and rectilinear. Therefore, they cannot be exactly superimposed on the rigid scanning pattern of automatic scanners.

Basic principles of ductal echography

The scans obtained by water-path echographic equipment allowed the operators to recognize, roughly, zones of abundant glandular tissue as hypoehoic (dark) zones within the more echogenic area of the lobes. These zones were not analyzable in detail except when the lobes were scanned longitudinally and main ductal structures were sufficiently enlarged and filled with epithelial cells. The best displays were observed when the radial mode of scanning centered on the nipple was used. With this technique, many infracentimetric cancers were detected. However, there was a high rate of false-positive. The value of this mode of scanning is reduced because of insufficient resolution, the non-rectilinear course of the ducts and the fact they were not, in real patients, directly superimposed on the geometrical pattern of the automatic scanner.

In view of these difficulties, a long hand-held, real-time, linear-array transducer was used in the multi-year, multi-thousand patient study in an attempt to follow the course of the ducts in spite of their individual geometrical variations. It was soon discovered that, in certain conditions with the real-time skin-contact scanner, it was possible to visualize ductal systems and mammary lobes and consequently to distinguish the epithelial tissue from the surrounding connective tissue. The respective pathologies of these tissues showed patterns which exaggerated their acoustic difference.

The epithelium (hypoechogenic), the connective tissue (echogenic) and their respective pathologies are displayed echographically by two opposite shades, or contrasting tones, allowing their differentiation.

Following this observation, a new approach to the echographic study of breast disease was adopted. It relied on the following factors:

1. the breast pathology to be investigated is epithelial:

2. mammary epithelium lines the acini, ductules and ducts which are the internal framework of the acinoductal axes of the breast;

3. the development of lesions in their early stage of growth preferentially follows anatomical and physiological acinoductal axes;

4. acinoductal axes converge toward the nipple, following approximately the radii of the angular sector covering each lobe;

5. epithelial and connective tissues show a different echogenicity, enabling differentiation between them;

6. breast diseases affect both the morphology and the echogenicity of both the epithelium and the adjacent connective tissue;

7. very early cancer of the breast shows a dual carcinogenic process affecting the epithelium and the connective tissue.

Echographic investigation now has a double purpose: (a) to visualize ductolobular structures and lesions in their periductal environment; and, (b) to provide echographic guidance in ducts and lesions for microsampling devices or fibroscopic examination.

This new technique, which combines in a single entity both echographic imaging and echo-guided sampling, was initially called echo-histological acinoductal analysis and, since 1989, ductal echography. The new method relies upon a different concept from that of conventional echography. The observer is now required to investigate the epithelial structures actively by systematically following ductal systems in mammary lobes. There is a permanent relationship between the image observed and the anatomic structure investigated. As a result, the lesions are not displayed as isolated, local, geometrical abnormalities in the ultrasonic field but as ductolobular alterations which are shown within their ductolobular and periductolobular environment. This mode of display illustrates the correspondence of their patterns with the textbook anatomy and pathology and allows a permanent understanding of the imaging.

The specific advantages of ductal echography

The difficulties with conventional echography and waterpath sonography were overcome by using a real-time scanner to perform a ductal mode of scanning. The scanner had a long linear-array transducer which could be positioned along the course of the ducts. This method fulfills the requirements and brings a successful solution to the problem of the ultrasonic investigation of the breast. There are four favorable factors having to do with the anatomy and four specific physical advantages of ultrasound which are exploited by this technique.

The four favorable anatomic factors are:

1. Ducts are supple and do not show significant geometrical variations. Consequently, a long linear-array transducer positioned along them will straighten them and display their course in detail.

2. Lobules fan out along the ducts, most often emerging from the superficial half side and are always orientated toward the skin. The linear-array display shown them in single file and in the same scan plane as the duct itself.

3. The intraepithelial (non-invasive) development of pathologies follows the ductolobular structures. They are displayed on the image along their greatest axis of development and hence with the best detail.

4. The transbasal (invasive) development of pathologies at early and moderately advanced stages extends predominantly towards the skin and along the ducts. The linear-array transducer positioned to image the duct will be in the most favorable position for the display of this development.

The four decisive physical advantages are:

1. Ultrasound distinctly displays the liquid or solid constitution of regions of the breast. This ability is common to all ultrasonic techniques but is much better exploited by ductal echography, which uses this property not only to determine the liquid content of gross cavities but also to display accurately the internal shape and exact contours of liquid-filled ductolobular structures.

2. Echography displays the epithelium and the connective tissue by two contrasting tones on the image, which allows their differentiation. Epithelium is shown as the interface lining the contours of the hypoechogenic (dark) hollow lumen of the ductolobular structures, and the supportive connective tissue is shown by a more echogenic (bright) appearance. For comparison, X-ray mammography does not usually display epithelium and the epithelial content because they are radiotransparent and hidden in and by the denser surrounding connective tissue.

3. Ductal echo graphy displays the contour of the epithelium through longitudinal sections which show its anatomical arrangement along several centimeters of ducts and lobules. This ability provides the means of observation and evaluation of the ductolobular structures, hence the means to pereceive the earliest epithelial alterations. Consequently, ductal echography demonstrates a major advantage over mammography in that it displays malignancies at an earlier stage, and therefore all mammographically visible cancers and, in addition, many cancers that are not, or not yet, mammographically visible. In comparison, with conventional echography the contour of the epithelium is displayed through random transtubular sections of about 1 mm$^2$ which appear in scans as random, echo-poor dots that are impossible to evaluate. It follows that conventional echography does not exploit this fundamental advantage of ultrasound because, while it detects exactly the same difference in echogenicity between these tissues, it is unable to do anything useful with it as it ignores breast anatomy completely.

4. The respective pathologies of epithelium and connective tissue show patterns which exaggerate their acoustic differences. X-ray mammography displays both pathologies by a straightforward variation of density. It follows that ductal echography demonstrates two major advantages over mammography.

(a) The distinct and specific display of the epithelial and connective involvements in pathologies.

(b) The display of malignancies (and benign pathologies) at an earlier stage than mammography, since it has the ability to display the contour of the normal epithelial structures and to recognize their first alterations not only through geometrical deformation, but also and specifically through the exaggeration of their low echogenicity. The consequences of this are two-fold: (i) already, ductal echography displays all the mammographically visible cancers and in addition will display many cancers that are not mammographically visible; and (ii) theoretically, ductal echography should be able to display all cancers as soon as they reach a stage of macroscopic perceptibility, if/when advances in equipment, training and knowledge allow the required conditions for their perception to be fulfilled.

However, although X-ray mammography generally does not show normal epithelial structures, it may draw attention to early malignancies (which are epithelial and hence radiotransparent at that stage) through: (i) the appearance of unpredictable indirect signs; (ii) microcalcifications; (iii) induced connective tissue density; and, (iv) alteration of the connective and vascular structures in reaction to the neoplasm. In a double-blind trial or experiment between X-ray mammography and ductal echography, it was shown that, if a cancer was missed by ductal echography, it was always accurately displayed by a second echographic examination of the area; the echographic signs existed in the breast and were shown by the appropriately orientated scans. Errors were due to human operator factors. If the cancer was missed by X-ray mammography, the cancer either remained undetectable by mammography or it was seen to show in the appropriate area indeterminate signs that did not allow normal diagnosis. Errors were due to technical factors.

It follows that ductal echography shows the ability to: (i) assess whether the early but nonspecific mammographic sign suggesting malignancy are linked with epithelial alterations and consequently to evaluate dubious mammographic signs; (ii) presume the absence of coalescent malignancy more than 0.5 cm in size if there is no perceptible direct corresponding epithelial alteration in a suspicious area (this is presumably to be confirmed later by a comparative investigation); and (iii) localize malignant cell areas specifically in anatomic features and geometrically in space, therefore to enable echo-guided cyto-aspiration of the best 'sampling areas' whether suggested or not by mammography or another means.

The results of these experiments are as follows.

Ductal echography offers the following benefits:

1. Normal ductolobular structures are shown with a distinct display of ducts and lobules, and hence with a distinctive display of the epithelial tissue in lobes.

2. Lesions are displayed in their greatest dimension, and hence with more detail: within their ductolobular and periductolobular environment; with precise display of the lobular and ductal involvements; with their real shape, their orientation and their insertion in breast anatomy; in an easily intelligible image because of its similarity to the textbook diagrams of anatomy and pathology.

3. Four benign diseases of the breast become directly diagnosable: ductal ectasias, hyperplasias, adenoscleroses and papillomatoses.

4. The display of fibrocystic dysplasias and fibroadenomas is also improved by determining the ductal and lobular involvements.

5. The diagnosis of breast malignancies is improved at early and moderately advanced stages by the distinct display of: (a) the epithelial malignancy and the connective reaction; (b) the ductal or lobular origin of involvement; (c) the intraductal spreading and the lobular and transbasal early invasive extensions of the malignancy; (d) the real shape and patterns of cancers and of their orientation and relationship to anatomic structures; and, (e) the best areas of malignant epithelial cell development of EGNAC.

6. A new set of criteria for the ultrasound diagnosis of malignancy has been established.

Basic difference between conventional and ductal echography

The classical criteria of malignancy used in conventional ultrasonic echography are based upon succinct 'geometrical' concepts (geometrical aspect of shape, shade, boundaries, uniformity and shadowing). See FIG. 3. They are limited to geometrical analysis of an abnormality in an otherwise randomly scanned and meaningless echographic field. This results in the impossibility to fulfill the fundamental mandatory requirement of the scientific precept that ought to rule any imaging technique: the absolute necessity to relate the image to anatomy and anatomopathology.

The new criteria used in ductal echography (DE) are based upon 'anatomopathological' concepts (the recognition of ductolobular structures and the evaluation of their alterations, made possible through the striking similarity which exists between the images produced by DE and the drawings made by the anatomopathologist).

Figure 4A:
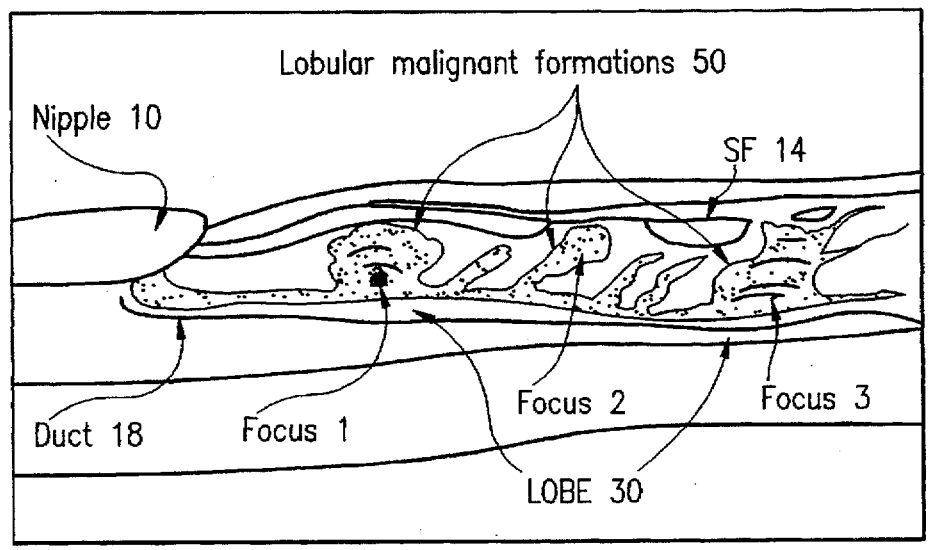
FIGS. 4a–c diagrammatically illustrate three (3) main types of malignancies which may be identified using ductal echography.
Figure 4B:
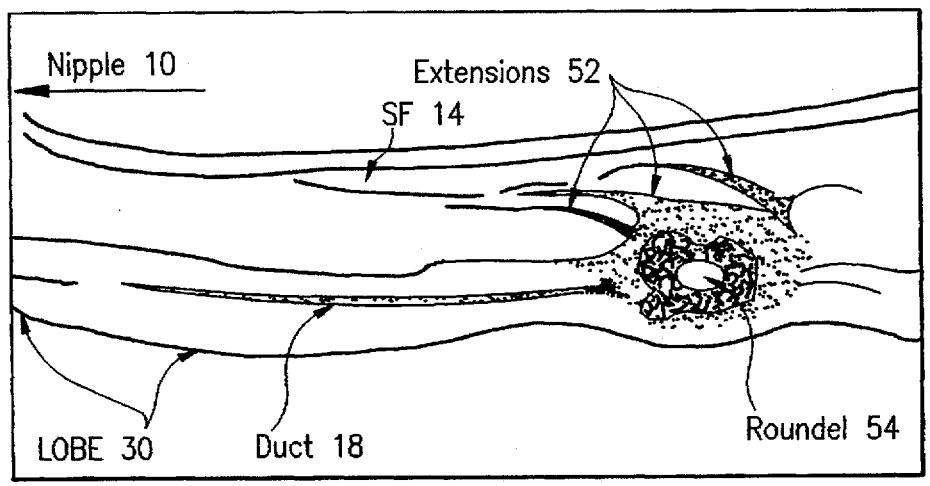
Figure 4C:
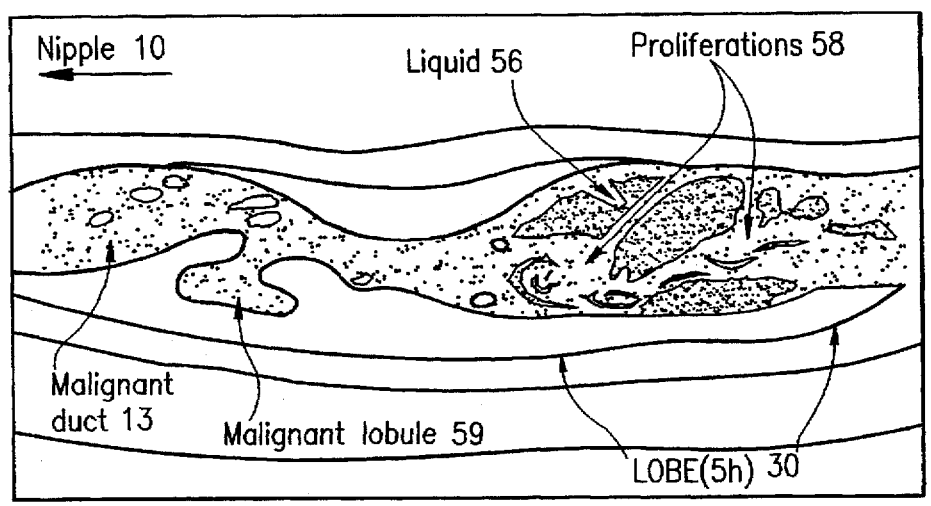

FIGS. 4a–c diagrammatically illustrate three (3) main types of malignantics which may be identified using ductal echography. FIGS. 4a, 4b and 4c illustrate axial ductal views of duct 18. These illustrations conform to standard medical protocol for representing these malignancies. Actual photographs of the ductal echographic images are not used in this patent application because of the poor print and reproduction quality of these images in printed patent documents. Accordingly, the line drawings in the present patent application of the ducts and malignancies and other ductal structures represent identifiable images found in the ultrasound scans.

Figure 4D:
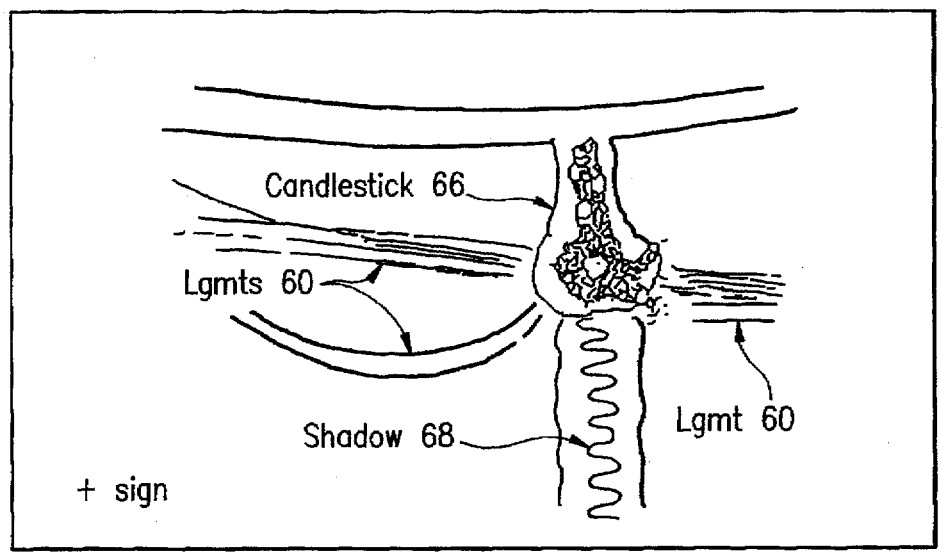
FIGS. 4d and 4e illustrate extensions from malignancies at an early stage of the invasive process.
Figure 4E:
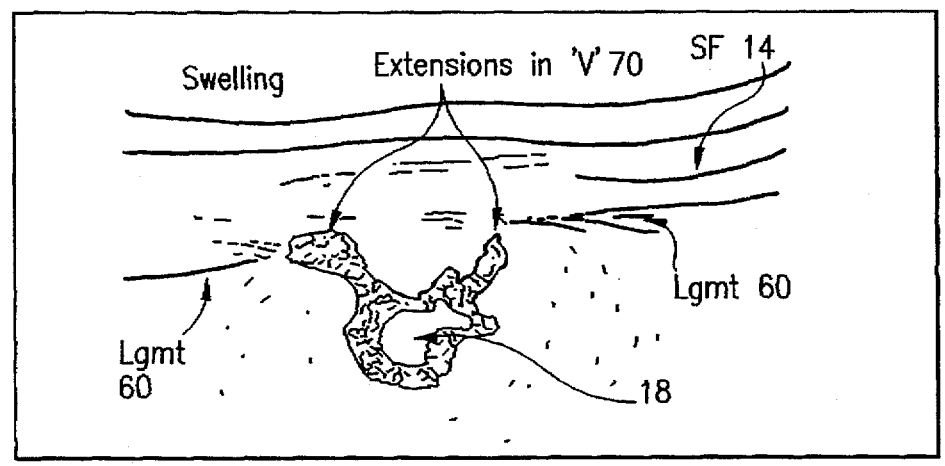
Figure 4F:
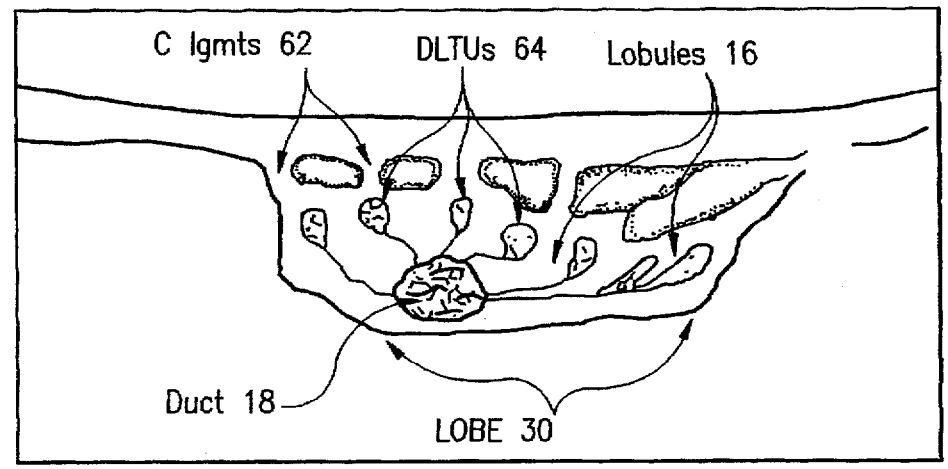
FIG. 4f illustrates a non-malignant condition.

FIGS. 4d–e display extensions from malignancies at an early stage of the invasive process, expanding through a lobule, along a superficial Cooper's Ligament towards the superficial fascia and the skin. These early malignant extensions induce important associated alterations in the local architecture of the breast. Consequently they are easily perceived because these architectural distortions are comparatively very extended (several centimeters at stages where the largest perceptible coalescent zones of epithelial malignancy are still only 0.5 cm in size). They can, therefore, be used as warning and guiding signs for detecting and accurately localizing small malignant foci, which subsequently will be micro-sampled through EGNAC technique to assess the diagnosis of malignancy at an earlier stage than the centimetric masses which are the most frequent diagnoses found with conventional techniques. FIG. 4f shows a non-malignant condition.

FIGS. 4a–e show lobular malignant formations 50, superficial fascia (SF) 14, focus 1, 2 and 3 (FIG. 4a) and extensions 52 from roundel 54 (FIG. 4b). In FIG. 4c, lobe 30 is located at approximately to 5:00 (5h) radial line. Liquid 56, proliferations 58 and malignant lobule 59 are also shown in FIG. 4c.

In FIGS. 4d, 4e, 4f, the scan is conducted transaxially across the duct 18. See, for example, FIG. 4f. Ligaments (Lgmts) 60 are shown in FIGS. 4d and 4e and Cooper's Ligaments (C Lgmts) 62 are shown in FIG. 4f next to ductal ligament terminal units (DLTU) 64. Candlestick 66 and shadow 68 are malignant signs shown in FIG. 4d. This is an "I" sign. FIG. 4e shows a "V" sign (extensions 70) which points towards minimal breast cancer (MBC). FIG. 4f shows a healthy or non-malignant candelabra sign. There are many other shapes that are discernable with the new imaging technique.

There is a remarkable richness of the information given by the new imaging technique, the ductal echographic technique. It allows the real shape and the orientation of cancers to be determined, as well as their relationship with the anatomical structures of the breast. It also shows differentiation between the epithelial malignancy and the connective reaction; a distinct display of lobular and ductal involvement; and a clear representation of intraductal spreading and invasive transbasal extensions, which are detectable from a very early stage.

DE, ductal echography, is not a simple radial mode of scanning. There is a basic difference between the conventional and ductal techniques in the concept of investigation, concerning both the mode of acquisition and the mode of interpretation of dam. In DE, the echographic field always has a specific anatomic meaning determined by the intelligibility of the display of the ductolobular structures. Formation and training are mandatory to acquire an understanding of the screen display sufficient to manage adequately the investigation and find the optimum display of data of interest. This optimum view can only be the consequence of the understanding of the pathology. Indeed, the dynamic research for a 'better scan' is not aimed at 'artistic' improvement of the image. It is conceptually the elaboration of the diagnosis.

Analysis of Malignancy using Ductal Echography (DE)

Three main types of breast primary malignancy are shown in FIGS. 4a–4c.

The ability to evaluate an optimum view requires one to have previously recognized the alteration and identified the development of the pathology, hence to have noticed its involvement with, or its effects upon, the lobe, the ligamentary structures, the superficial fascia and the skin that are the four elements constituting permanently the identifiable meaningful framework of the DE image.

In the field of imaging performance, DE outclasses all other current techniques through the intelligibility of the anatomic and anatomopathological significance of displayed data.

DE of the Early Invasive Process

FIGS. 4d–4e show some malignant extensions and cruciform arrangements of secondary features. In FIG. 4d a worm or candlestick pattern is shown. In FIG. 4e the two extensions 70 diverge from the laterosuperficial parts of the duct 18, giving a V-shaped pattern on a transductal scan. After a depth of 5–15 mm, lateral extensions 70 bend towards the skin to reach the superficial fascia (SF) 14.

It is essential to differentiate malignant extensions from normal lobules. The transductal scan diagram in FIG. 4f shows normal lobules 16 emerging from the duct 18 in a sunrise pattern. Compare this figure with the malignant extensions displayed in FIGS. 4d, 4e and notice their association with sets of secondary signs suggestive of malignancy. However, the differentiation is not always easy and may require EGNAC (echo guided needle aspiration cytology) in some cases of benign hyperplasias.

FIGS. 5a, 5b and 5c show DE diagnosis of an MBC (Minimal Breast Cancer) from two microcalcifications detected via X-ray mammography.

FIG. 5a diagrammatically illustrates an X-ray mammography of two microcalcifications 70a, 70b. FIG. 5a replicates the size and location of microcalcifications 70a, 70b in the actual X-ray image. FIGS. 5b and 5c, respectively, illustrate the axial ductal view and the transductal view. FIGS. 5b and 5c show focus 81, lobular extension 83 and pulling 85.

FIG. 5a shows the earliest possible detection of malignancy that might be performed with X-ray mammography. The actual X-ray image shows a relatively translucent breast and two small round-shaped microcalcifications without any other sign. The perceptibility of the microcalcifications may be greatly improved by the computerized treatment of the X-ray film. Some transparent ductolobular structures have become perceptible with this image enhancement. However, no other sign evocative of malignance was exhibited. In FIGS. 5b and 5c, ductal echography of the corresponding duct displays distinctly a well developed cellular proliferation in the duct 18 and in a lobule 83, with obvious associated signs suggesting manifestly a malignancy (distortion and hyperechogenicity of local ligamentary structures contrasting with the increased hypoechogenicity of the swollen epithelial features).

EGNAC (Echo Guided Needle Aspiration Cytology) of this MBC was performed in a few minutes at the end of the ultrasonic investigation using ductal echography, and the malignance was cytologically assessed the same day. Comparing this procedure to the complicated, inefficient, time-consuming, more expensive and more traumatic radiostereotaxic procedures, it is difficult to understand why X-ray mammography is still used for this purpose. Comparing the richness of the information provided by DE images with the extremely rudimental mammographic symptomatology, the situation is further clarified. Mammography did, however, provide an advantage by drawing attention to the area for further investigation.

Ductal Echography—the Impact on Daily Practice

For the past 20 years the breast has been the only organ to have been examined echographically with no regard to its detailed internal anatomy. The investigations have been carded out and are still carried out today by operators unable to appreciate the structures they are examining and unable to identify them on the images. This is an incredible and unacceptable state of affairs. The reasons behind it are briefly described herein, but now it is time to realize the potential of echography, remove the flaws inherent in the current procedures of combined mammography and conventional echography and rationalize the investigation process by the intelligent application of visible anatomical clues.

The length of time during which it has been accepted that the breast does not have a discernable ultrasound anatomy accounts for the current reluctance to accept a rational imaging protocol based on the systematic display of epithelial structures. However, it is often the case in other fields of endeavor that once an insurmountable challenge has been conquered, other 8 significant advances suddenly appear. Indeed, they are often able to improve on the pioneer's performance. It is the initial success which prepares others to believe in its possibility. Operators and technicians simply need to adopt the expectation that they will be able to sonographically image and recognize ducts on ultrasound scans.

Conventional echography has very little credibility for diagnosis, other than the coarse differentiation of solid from liquid, and the only way to change this attitude is to abandon conventional mass-orientated echography in favor of echography of the ducts. This will reduce the harm currently being inflicted on patients as they are denied the benefits of the most informative investigation currently available. It is indeed self-evident that the breast cannot be considered as having been validly investigated without its epithelial ductolobular structures being observed and understood. Since this possibility is now presented by DE or ductal echography, the persistence of the prevailing situation is not tolerable and it is not ethically acceptable to obstruct the evolution of breast investigation to one of rational logical imaging.

Figures 6A, 6B:
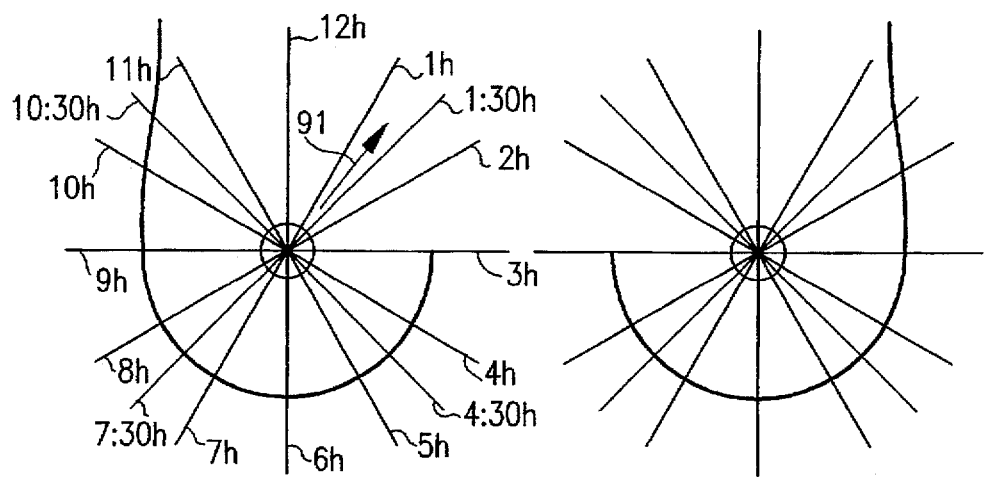
FIGS. 6a and 6b diagrammatically illustrate the radially outward scanning pattern as recommended by the ductal echographic procedure herein.

FIGS. 6a and 6b diagrammatically illustrate the radially outward scanning pattern as recommended by the ductal echographic procedure herein. FIGS. 6a and 6b illustrate the left and right breast, respectively. For example with respect to FIG. 6A, longitudinal and radially outward scanned at 12:00 is identified as 12h. The other scans are similarly identified as 1:00 (1h, 2h, 3h . . . 11h). In addition, partial clockface scans at 1:30, 4:30, 7:30 and 10:30 indicate that these are simply estimates. In fact, the sonographer should locate the 12–24 ducts and axially follow each of those ducts. Since these ducts may be located at various positions radially displaced around the breast, radially spaced along spokes of a wheel, the sonographer should be careful to locate and follow each duct independently. The scan is longitudinally and radially outward shown by arrow 91 in order to acquire the axial ductal image.

Figure 7A:
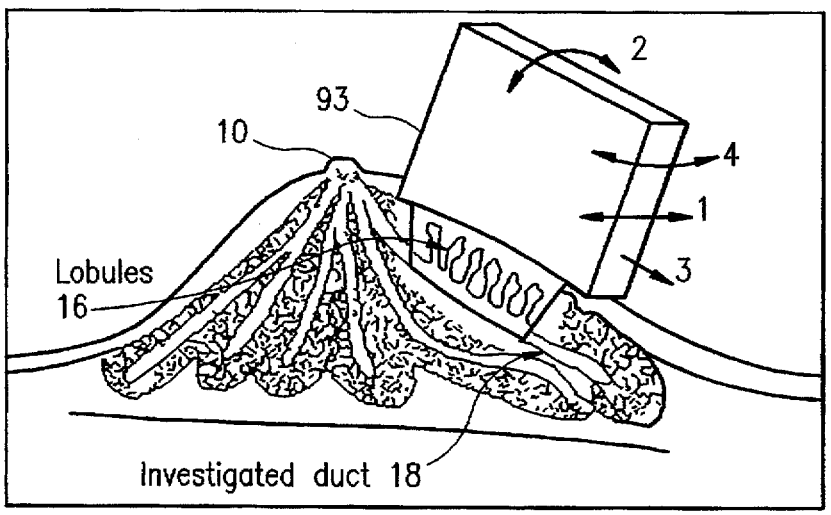
FIG. 7a diagrammatically illustrates an ultrasound axial ductal scan with scan head 93 atop a breast.

FIG. 7a diagrammatically illustrates an ultrasound axial ductal scan with scan head 93 atop a breast. FIG. 7a diagrammatically illustrates the resulting scan image. With this new technique, scan head 93 initially scans nipple 10 and the diameter of the areola. As described later herein, the sonographer should measure, prior to or subsequent to the scan, the actual dimension of the areola. This actual dimension will be matched or keyed to the scale and the recticle on the scanned image which includes the entire scan of nipple 10 and areola 12 (see FIG. 1b). After having set the transducer perpendicular to the areola surface and having positioned the nipple at the middle of the echographic field, the operator will rotate the transducer over 180°, around its central axis. This will allow him or her to observe and display the interesting features in the retro areolar zone.

Descriptions of the manipulations of the transducer in regard with the axia of the duct.

1. Side-sliding laterally to the duct.

2. Axial-ductal revolving (arrow 4) around the ductal hub to display files of lobules oblique to the skin.

Axial longitudinal sliding along the duct. (arrow 3)

Spinning rotation of the transducer around its medial axis to produce transductal scans.

5. Transductal tilting of the transducer to display lobules oblique to the skin. (arrow 2)

The long ductal portion displayed in axial ductal scans (FIG. 7b) gives a valuable synoptic representation of ductal systems. Through their imaging, similar to the textbook anatomy, these scans are easy to understand and they give the greatest amount of information that a non-invasive physical method is able to provide nowadays. It is obvious that all the lobules fanning out of the superficial side of the duct cannot by displayed in the same scan. However, the evaluation of pathologies does not seem to be greatly affected, as experience shows that the growth of pathologies, mainly at early and moderately advanced stages of development, always evolves towards the skin, in a sector of cylinder narrowing with age, and having for axis the duct and for surface of revolution the skin.

This sector of cylinder is not rectilinear but slightly undulated, and is either perpendicular or oblique to the skin. The most interesting file of lobules is always found in this sector of cylinder and can be selected by echoscopy by revolving the transducer around the axial ductal hub. One or two other interesting files might be also selected and gathered together in the same image as displayed in FIG. 13.

The axial ductal scan begins at nipple 10 and extends radially outward along the axis of the duct 18. This is in direction 3 shown in FIG. 7a. In order to locate and follow the duct, the sonographer may shift scan head 93 to the left or to the right of investigated duct 18. This is shown by the double head arrow 1 in FIG. 7a.

Figure 7B:
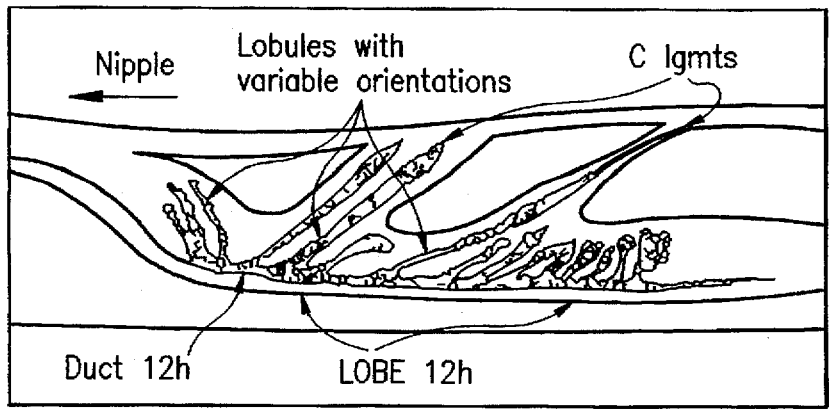

The resulting axial duct image is diagrammatically illustrated in FIG. 7b. In FIG. 8b, ducts have been identified as duct 11h, duct 12h, and duct 1h, at 11:00; 12:00 and 1:00. Of course, these are approximate locations as shown in FIGS. 6a or 6b. Since further investigation of a problematic duct may be conducted later, it is only necessary for the sonographer to generally identify the clockface position of the duct on the imaging record such that the physician can quickly identify that duct later on. Further, a specific aspiration of the fluid or cells in the duct may be conducted as discussed above with the echo guided needle aspiration cytology. (EGNAC)

FIG. 8b diagrammatically illustrates that Cooper's ligament 62 is orientated at an oblique scan angle 95 with respect to the surface of the skin 96.

The sonographer can locate these oblique angles by revolving or rotating scan head 93 (FIG. 7a) around the ductal axis as shown in direction 2 in that figure. The resulting axial ductal scan is diagrammatically illustrated in FIG. 7b. As discussed later, it is important that the sonographer note the approximate oblique angle 95 (during an axial scan per FIG. 7a) and also capture the electronic image at oblique angle 95 (during transaxial scan per FIG. 7b) and a second oblique angle (by rotating in direction 2 during an axial scan per FIG. 7a) in order to provide a three-dimensional view of the duct under investigation.

When ultrasonic scan head 93 cannot extend the entire length of the duct, a composite axial ductal image is obtained by sequentially scanning two ductal segments along a singular duct and electronically compiling the images as a composite axial image of the duct. This is accomplished by having the sonographer continuously or periodically save the scan as he or she moves scan head 93 from nipple 10 outward along the axial dimension of a duct or by having the sonographer periodically capture axial segments of the duct by an appropriate instruction entered into the ultrasound machine.

Figure 8A:
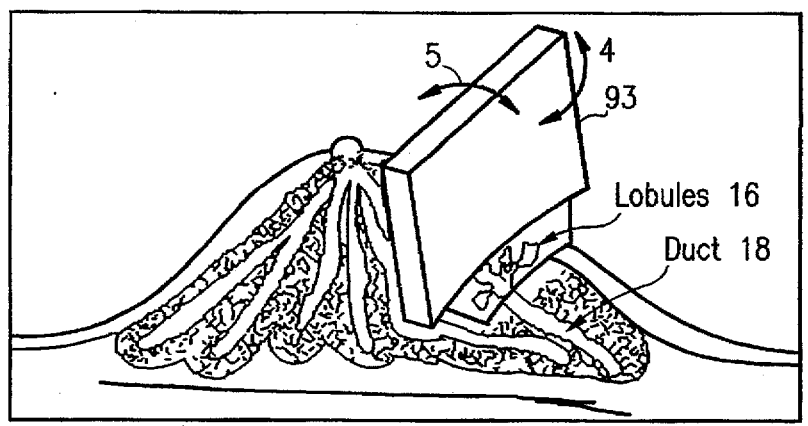
FIG. 8a diagrammatically illustrates scan head 93 capturing a transductal view of lobes 16.
Figure 8B:
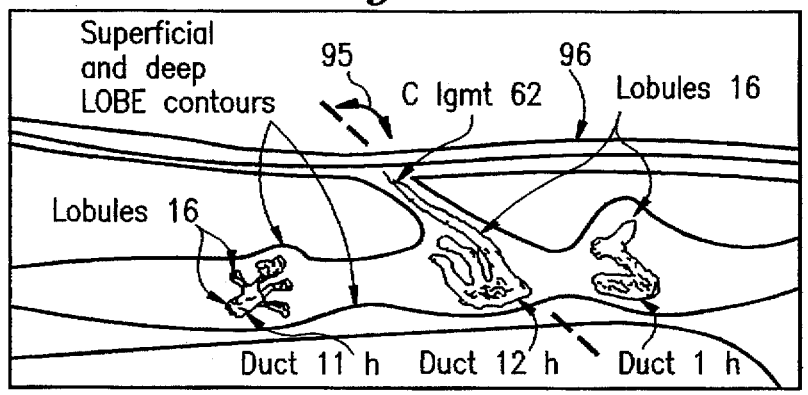
FIG. 8b diagrammatically illustrates the resulting transductal scan.

FIG. 8a diagrammatically illustrates scan head 93 capturing a transductal view of lobes 16. In FIG. 8a, duct 18 is under study. The sonographer should capture both an axial ductal segment (FIGS. 7a, 7b) as well as a transaxial ductal segment (FIGS. 8a, 8b) simply by rotating the scan head 93 90° about a particular lobules 16 under study. Fuaher, lobules 16 and Cooper's ligaments 62 may not be perpendicular to the surface 96 of the skin. The sonographer should rotate scan head 93 in the direction shown by double headed arrow 5 in order to electronically capture the transaxial ductal view of lobules 16.

FIG. 8a diagrammatically illustrates scan head 93 capturing a transductal view of lobule 16. FIG. 8b illustrates a scan perpendicular to the duct orientated at 12h showing the two adjacent ducts, the 11h duct on the left and the 1h duct on the right. However, the transductal display of ductal epithelium is very poor and limited only to the section of the contour of the duct and of a few lobules. This transductal display of the lobular epithelium is impossible to obtain from random scanning of conventional echography, as lobules are not obligatorily parallel and do not show predictable axes of orientation towards the skin.

To display lobules, it is mandatory to perform an axial ductal scan as shown in FIG. 7a. The resulting image in FIG. 7a allows one to determine their angle of orientation towards the skin, then to rotate the transducer to 90°; to tilt it conveniently; and to slide it along the duct until 18 the investigated lobules appear in the echographic field.

The dashed line in FIG. 8b shows the angle of revolution at which the transducer had to be revolved around the axial ductal hub (at duct 12h) to be able to obtain the display of the most interesting file of lobules.

Figure 9A:
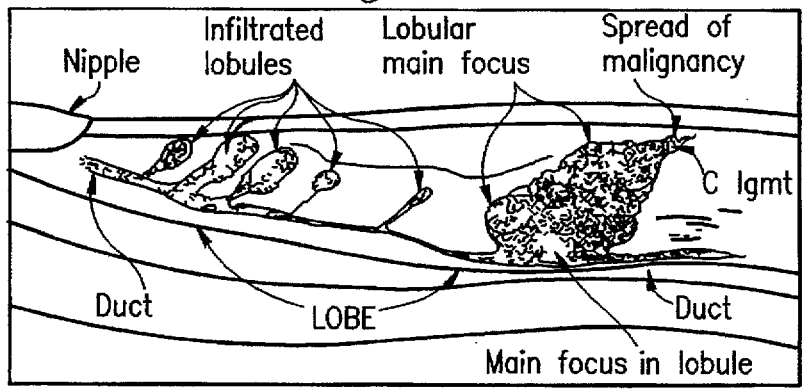
FIGS. 9a and 9b diagrammatically illustrate an axial ductal scan of a ductal system affected by lobular carcinoma.
Figure 9B:
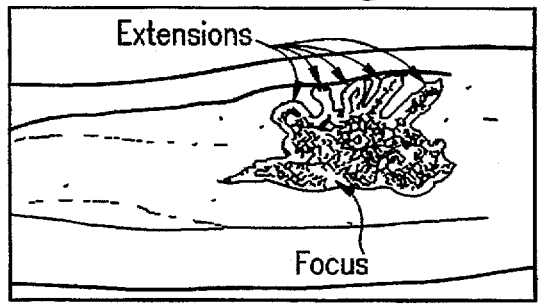
Figure 9C:
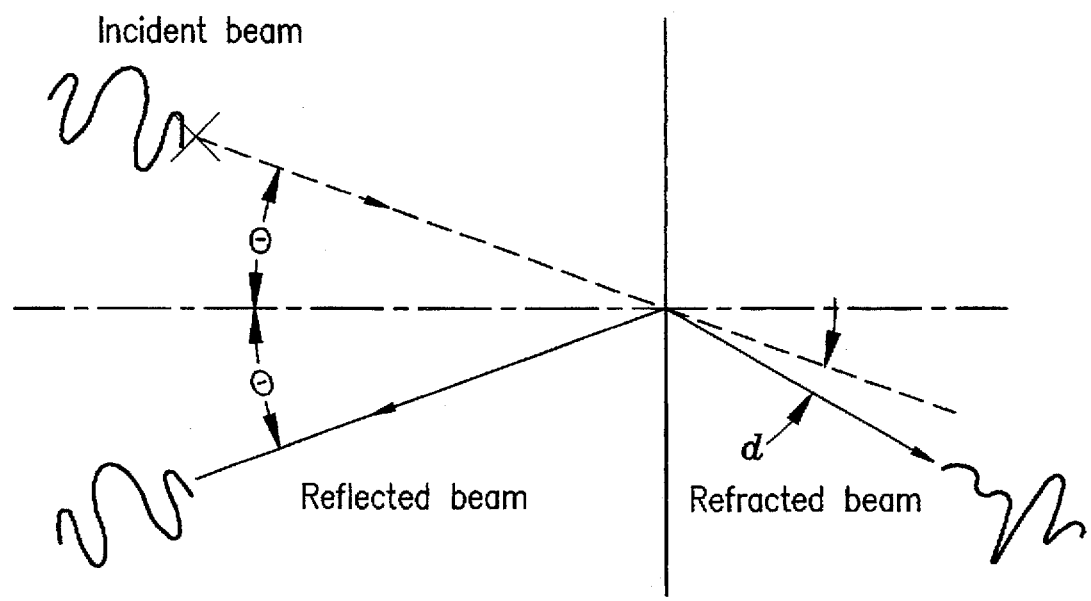
FIGS. 9c and 9d show specular reflection and scattering reflection, respectively.
Figure 9D:
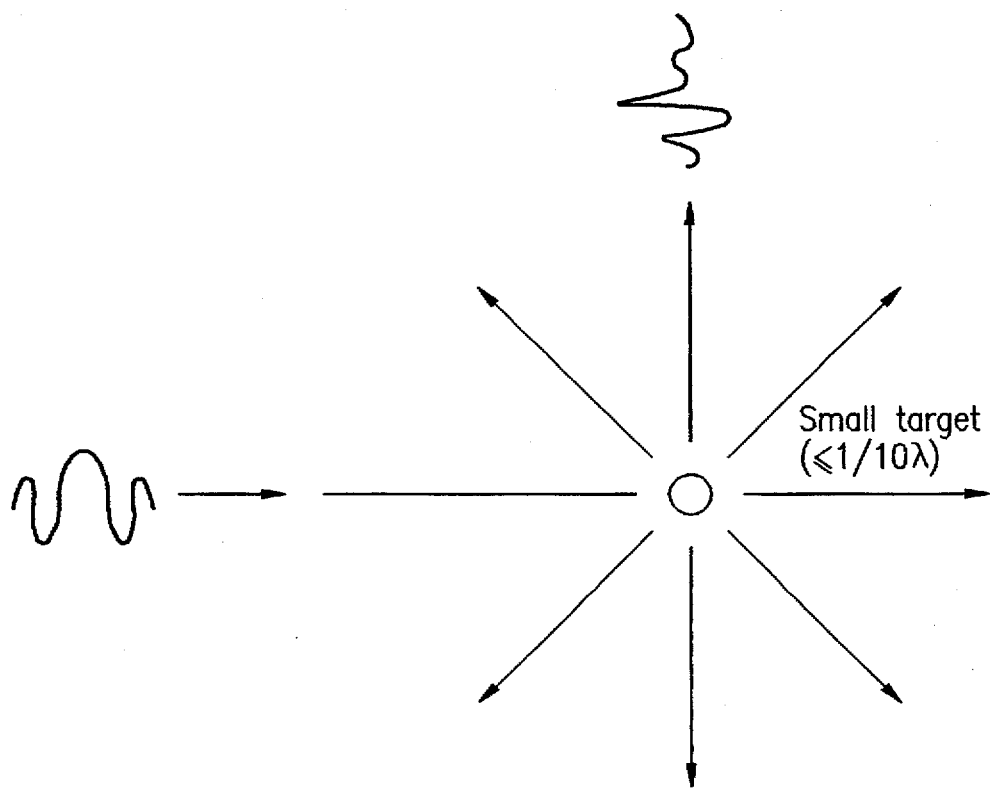

FIGS. 9a and 9b illustrate an axial ductal scan of a ductal system affected by a lobular carcinoma.

FIG. 9b shows the most informative view that a transductal scan is able to provide, which corresponds to the best possible random scan obtained with conventional echography. With respect to FIG. 9a, notice the decisive superiority of the information provided by the axial ductal scan, both qualitatively and quantitatively. This comprehensive axial ductal scan allows the understanding of the pathology through the information provided on the development of lesions in space along the duct and the development of the pathology with time, by showing the different stages in development of the malignant pathology. The remarkable similarity of DE imaging to anatomopathological illustrations allows an easy recognition of the distinct display of the successive affected lobules along the skin side of the duct, each being at a different stage of malignant transformation. The intelligibility would be considerably reduced with small part scanners producing echographic fields of 3 or 4 cm. In the field of imaging performance, this image outclasses any other image produced by any other current technique through the richness, accuracy and clarity of the information provided, and also through the intelligibility of the anatomic and anatomopathological significance of displayed data. The mode of display by DE techniques has provided DE imaging with the quality of anatomopathological plates. Incidentally, these lobular carcinomas like diffused malignancies, reoccurrences and focal cancers at early stages are usually not radio-diagnosable.

FIG. 9c shows specular reflection. Large flat boundaries (greater than 20 wavelengths [1/f]) between tissues reflect ultrasound waves like a mirror. This allows the display at boundaries of features that would normally be too thin to be physically discernible with the resolution of wavelengths usable in daily practice (e.g., pleura, ductolobular structures).

FIG. 9d shows scattering reflection. Very small targets reflect ultrasound individually in all directions. This allows the display of their individual position in space (2D or two-dimensional imaging) and the evaluation of their movement off and to the transducer, both individually (frequency shift spectrum) and globally (quantified blood flow).

Figure 10:
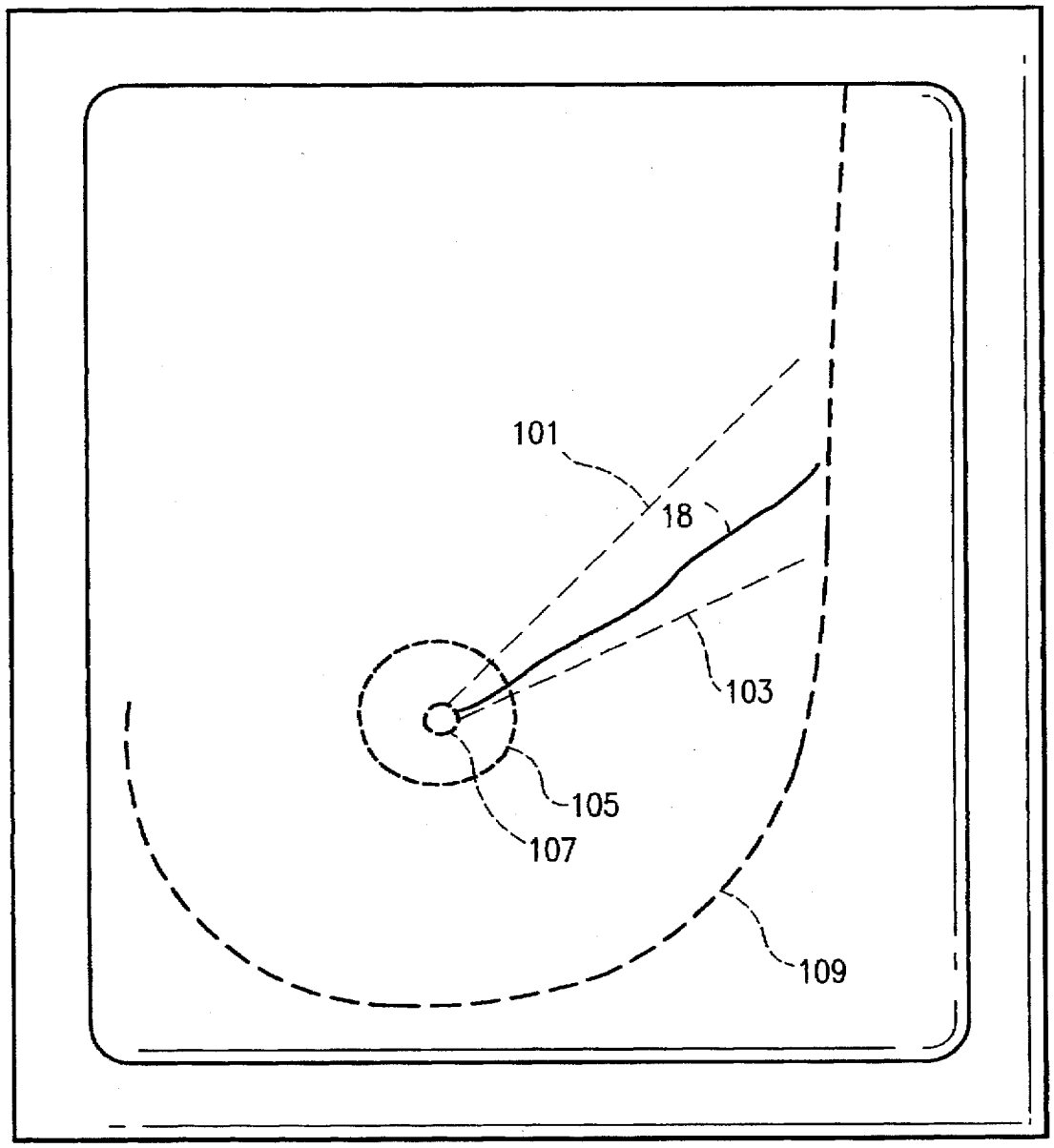
FIG. 10 diagrammatically illustrates a template that is displayed on the monitor for the ultrasound machine.

FIG. 10 diagrammatically illustrates a template that is displayed on the monitor for the ultrasound machine. Duct 18 is shown meandering within a clockface zone identified by dashed lines 101 and 103. The sonographer should note the general clockface position (approximately 2:30 in FIG. 10) and annotate the electronic image or annotate the electronic records accordingly to note the clockface orientation of the scan. The template also includes areola template 105 and nipple template 107. Part of the present invention includes acquiring a sonographic image of the entire diameter of areola 12 (FIG 1b). Also, the sonographer should measure and input into the computer system the actual dimension of areola 12. Since most ultrasound machines enable the sonographer to note the scale on the electronically acquired image, the computer system described herein matches and conforms template size 105 to the acquired electronic image of areola 12 and further to the actual measurement of areola 12. Accordingly, once this measurement and matching occurs, all axial segments of duct 18 and all acquired electronic images of duct 18 can be matched to that scale. By utilizing the template, which further includes J-shaped lines 109, the sonographer and also the physician can quickly locate duct 18 with respect to the patient's breast. In a further refinement of the invention, the operator may magnify the image by overriding the actual scale match described herein. A predetermined scale may also be selected for the global display of the ductal systems.

Of course, the patient may have between 12–24 ducts in her breast. Only a single duct is illustrated in FIG. 10. However, the computer system described herein can show all the ducts whose images are acquired with the ultrasound machine. For simplicity, only a single duct is shown in FIG. 10. Returning to FIG. 1b, that figure diagrammatically illustrates three ducts which could be electronically captured and stored as an electronic image.

FIGS. 11a–11g show an axial ductal view and six transductal views of breast cancer. In actuality, this cancer was masked by the reactive mass of connective or stroma reaction. In other words, the X-ray mammograph did not show the real epithelial malignant part of this breast cancer. In contrast, the ductal echographic technique described herein quickly identified the real epithelial cancer and its extensions within and through the hyperechogenic fibrotic surrounding connective stromal reaction.

This ability of ductal echography to display distinctly the alterations specific to the epithelial and connective tissues has induced an immediate major improvement in early diagnosis by allowing a very accurate echo-guidance of micro-sampling devices in the real epithelial zone of malignant cells. This potential has resulted in a very high rate of true positives over 90% for shapes greater than 0.5 cm. This, in turn, has led to:

1. the abandonment of the surgical biopsy for explorative purposes in most cases;
2. the split of the role of mammography;
   a. mammography keeps the first role for screening and rapid but defective detection;
   b. mammography has lost its role in the assessment of the diagnosis which will be performed earlier, more easily, more rapidly, hence more efficiently by ductal echographic techniques.

Figure 11A:
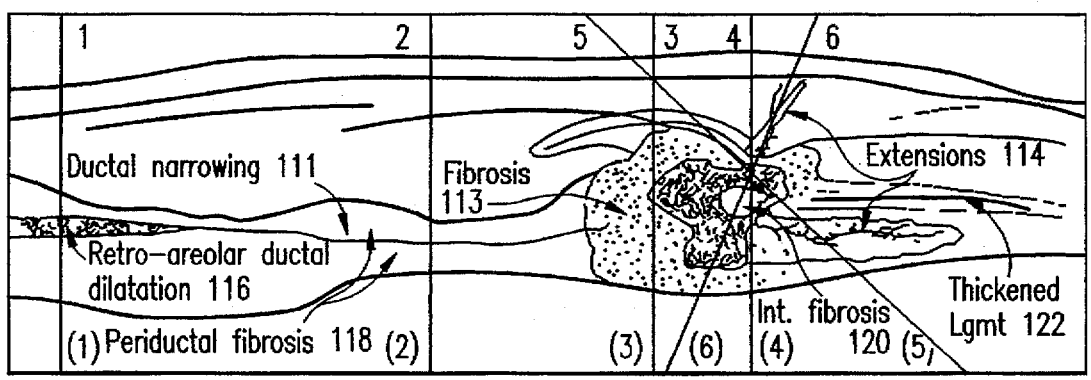
FIGS. 11a–11g show an axial ductal view and six transductal views of breast cancer.
Figure 11B:
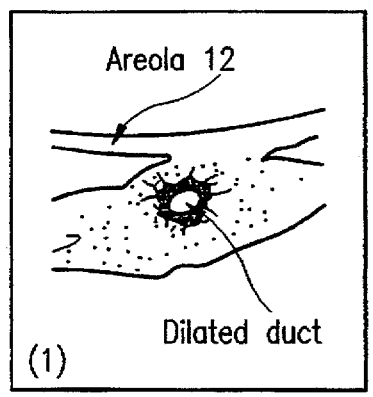
Figure 11C:
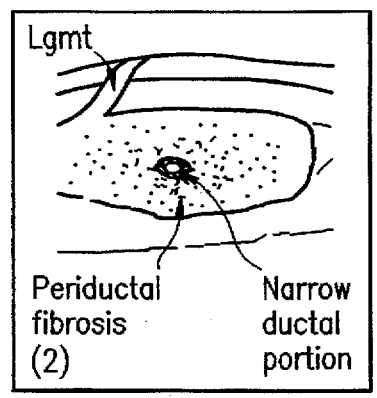

FIG. 11b is a transductal view along section line 1—(1) in axial ductal image FIG. 11a. FIGS. 11c, d, e, f and g are transductal views along section lines 2—(2); 3—(3); 4—(4); 5—(5); 6—(6), respectively.

In FIG. 11a, the duct under study has a ductal narrowing region 111, fibrosis 113, extensions 114, retroareolar ductal dilation region 116, periductal fibrosis 118, internal fibrosis 120 and a thickening ligament 122.

Further, FIG. 11a diagrammatically illustrates that the sonographer may periodically save scanned axial segments of the duct. Those scanned axial segments are saved periodically (based on a pre-determined timer or time) or maybe saved by the sonographer manually when he or she determines that a reasonable amount of axial duct image segment has been captured by the scan head. As used herein, the term ("saved") refers to the ultrasound machine electronically saving the acquired image in its memory. As described later, this memory could be random access memory in the sonogram machine or computer, may be hard drive memory, CD ROM (assuming the machine could record on the CD ROM) or may be the memory on the video board electronically coupled to the scan head.

Further, the sonographer may record the entire ultrasound session on a videotape (with a VCR hookup) and some of the processing discussed herein could be conducted post date acquisition. This is discussed later herein.

Figure 11D:
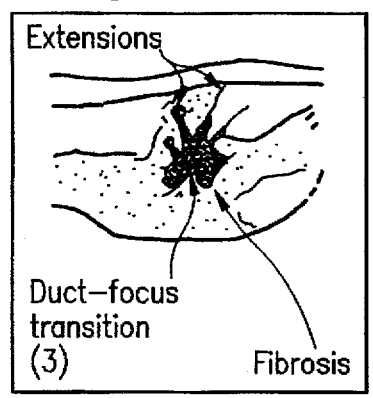

FIG. 11b shows areola 12 and a dilated duct. FIG. 11c shows a ligament extending above the duct, a narrowed ductal portion and a periductal fibrosis. FIG. 11d shows a plurality of extensions leading towards the skin surface of the duct-focus transition. Further, the ductal echographic image shows a fibrosis around the focus.

Figure 11E:
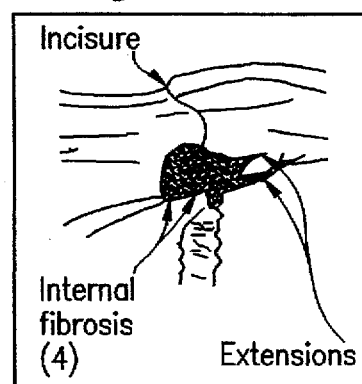
Figure 11F:
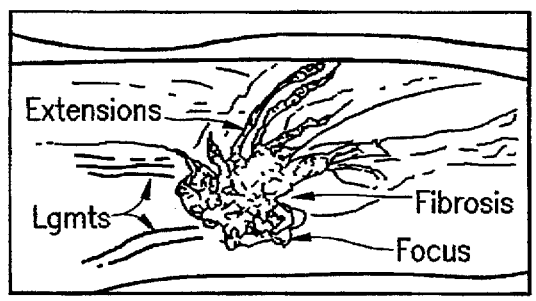
Figure 11G:
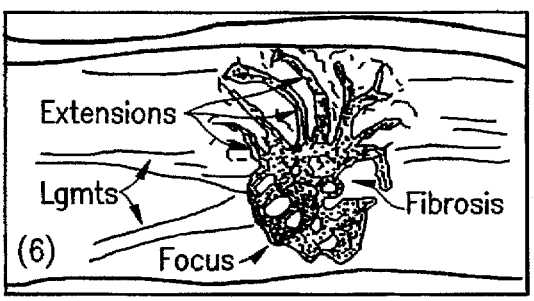

FIG. 11e corresponds to transductal scan 4—(4) in FIG. 11a, and shows an incisure, and internal fibrosis and various extensions. FIG. 11f is taken at an oblique angle approximately 45° to the surface of the skin. In other words, the sonographer rotated scan head 93 (FIG. 8a) in the direction shown by double headed arrow 5 such that the scan head was at an oblique angle 5—(5) with respect to the skin of the patient. At this oblique angle, a plurality of extensions are shown in FIG 11f extending towards the skin of the patient. Further, FIG. 11f shows ligaments, a focus and surrounding fibrosis. FIG. 11g shows extensions, ligaments, focus and fibrosis. The transaxial ductal scan in FIG. 11g was taken at a different oblique angle, approximately 80° with respect to the skin of the surface. These oblique angles are the nearest acute angle between the scan head and the surface of the skin. An electronic sensor can be fixed on the transducer to display automatically the different angles given to the transducer from a position of origin taken as reference, e.g., along the ductal axis and perpendicularly to the skin. As described later, the sonographer should electronically note the oblique angle while he or she acquires and saves the sonogram of this axial duct segment. These oblique angles are utilized to form the three-dimensional image of the ductal system discussed later.

Figure 12:
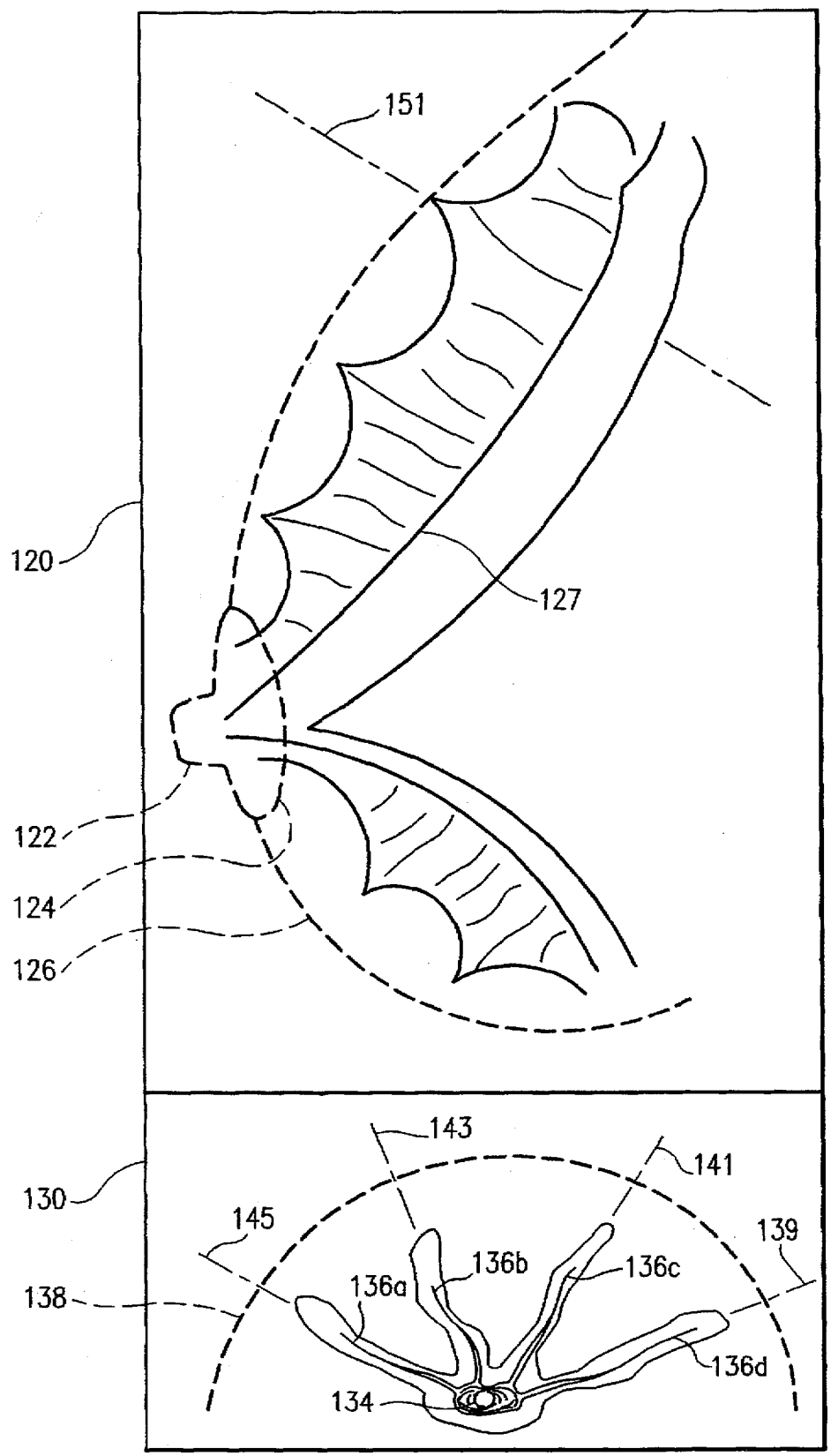
FIG. 12 shows a display area 120 and a cross-sectional breast template formed by dashed lines.

FIG. 12 shows a display area 120 and a cross-sectional breast template formed by dashed lines. The template shows nipple 122, areola 124 and a cross sectional view of the surface of the breast 126. This axial view of the duct is saved by the machine or by the operator (if under manual control). The complete axial view is created in the first scan if the lobe is shorter than the echographic field or by the piece-wise addition and location of two or multiple axial ductal views, depending on the size of the echographic field. Hence, the advantage of long transducers (8 cm.) which will display in one scan all ductal systems in small breasts and the ductal systems of the lower inner half in large breasts. Eight (8) cm. long transducers will display all upper outer ductal systems in large breasts in two scans. The axial ductal view shown in FIG. 12 could be the same as the clockface presentation of duct 18 shown in FIG. 10. However, in FIG. 12, the computer system has rotated the image and further shows some enhancement of that axial view by adding ductal segments obtained in the scan plane at a certain oblique angle. As shown in FIG. 12, duct 127 and associated connective tissues form a suspension bridge system as generally shown in FIG. 1c, Stage 2 (upper lobe). The suspension bridge sonographic image is diagrammatically illustrated in FIG. 1c as a Stage 2 situation in the upper lobe of that FIG.

Another addition to the display shown in FIG. 12 is the concurrent display in region 130. This display shows a horizontal cross-section of duct 134 showing a plurality of Cooper's Ligaments 136a, 136b, 136c and 136d. The surface of the breast is shown as a template 138 in dashed lines. The sonographer captures these Cooper's Ligaments by rotating the scan head 93 while in the transaxial ductal mode illustrated in FIG. 8a. The electronic image is further enhanced if the operator moves in an axial ductal mode (FIG. 7a) and captures the axial segments of these Cooper's Ligaments at oblique angles identified as 139, 141, 143 and 145 in FIG. 12, display region 130). As a further enhancement, the display in FIG. 12 could be enhanced by showing as a template where the transaxial ductal picture in region 130 is located. This transaxial ductal scan plane in display region 120 is indicated by section line 151.

Figure 13:
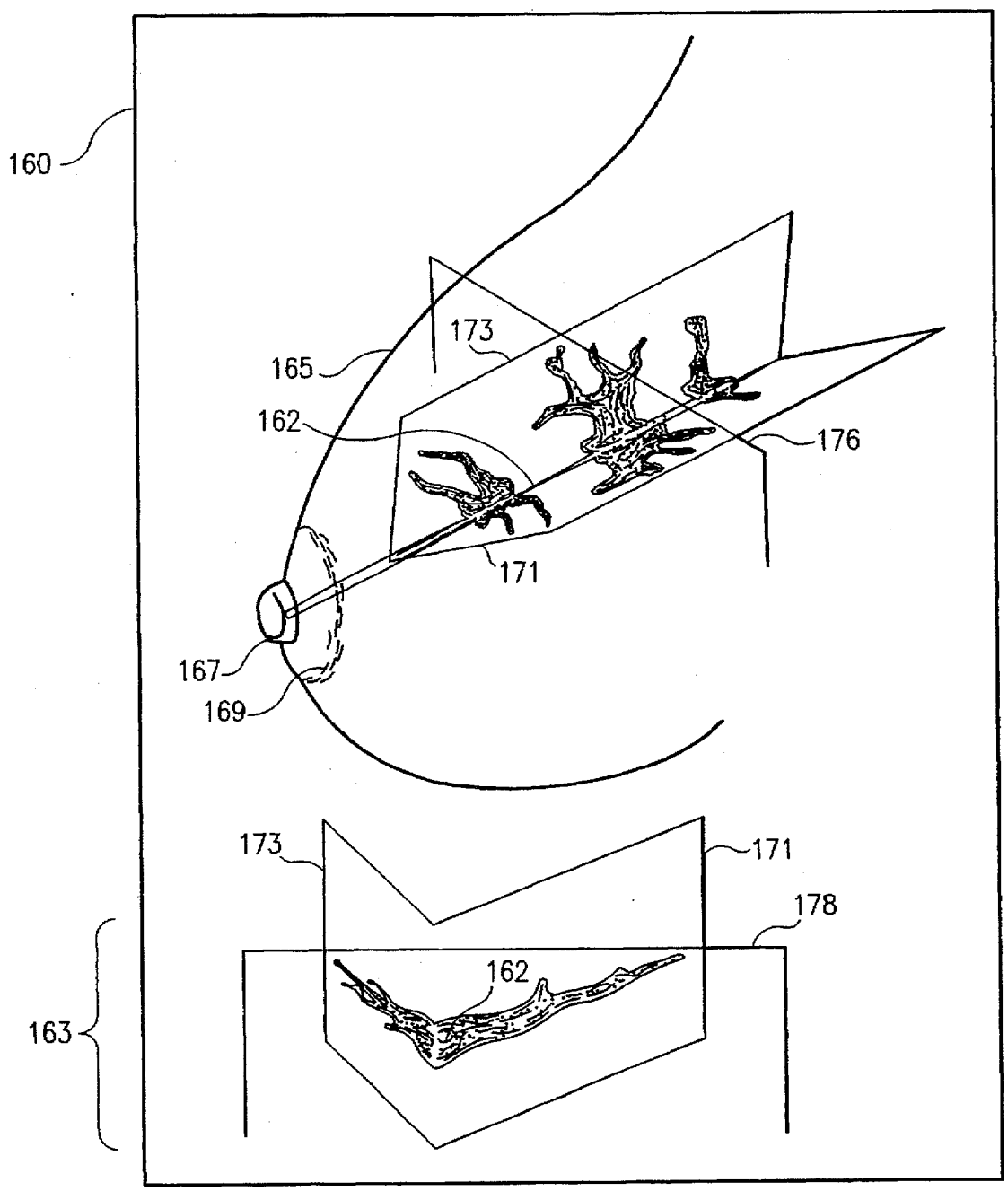
FIG. 13 shows display region 160 and a three-dimensional representation of the duct 162.

FIG. 13 shows display region 160 and a three-dimensional representation of the duct 162. Further, display region 160 shows a transaxial view of duct 162 in lower region 163.

A three-dimensional perspective view of breast 165 is shown as having nipple 167 and areola 169. An axial ductal scan of duct 162 has been compiled by piece-wise composite method described later in conjunction with the flow chart of the computer program. In addition, the sonographer captured the electronic image of duct 162 at an oblique angle identified by scan plane 171. In addition to the image at scan plane 171, the sonographer has obtained another scan in plane 173. The computer system has juxtaposed and created a three-dimensional image with the axial ductal scans in both planes 171 and 173 such that the fibrosis and Cooper's Ligaments are shown as three-dimensional images. The transductal view shown in lower display region 163 is the image captured at scan plane 176. This tranaxial view is supplemented with small scan image segments from scan planes 171 and 173. In addition, the axial ductal view and scan plane therefor is shown as scan plane 178 in the transaxial image shown in region 163. The scan planes 171 and 173 are also shown. Accordingly, the duct and the fibrosis and Cooper's Ligaments are shown concurrently such that the physician can readily ascertain the condition of the lobule at that particular location.

Figure 14A:
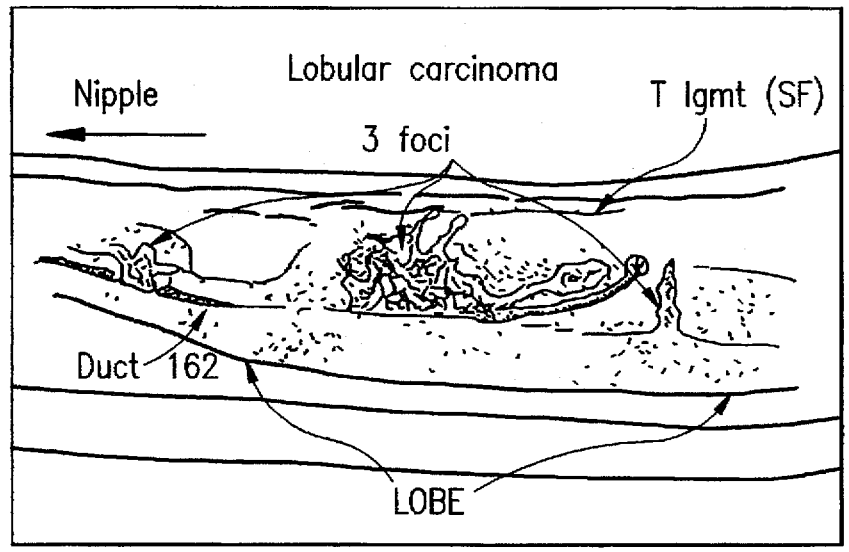
FIGS. 14a and 14b diagrammatically illustrate the axial ductal views in scan plane 171 and scan plane 173, respectively.
Figure 14B:
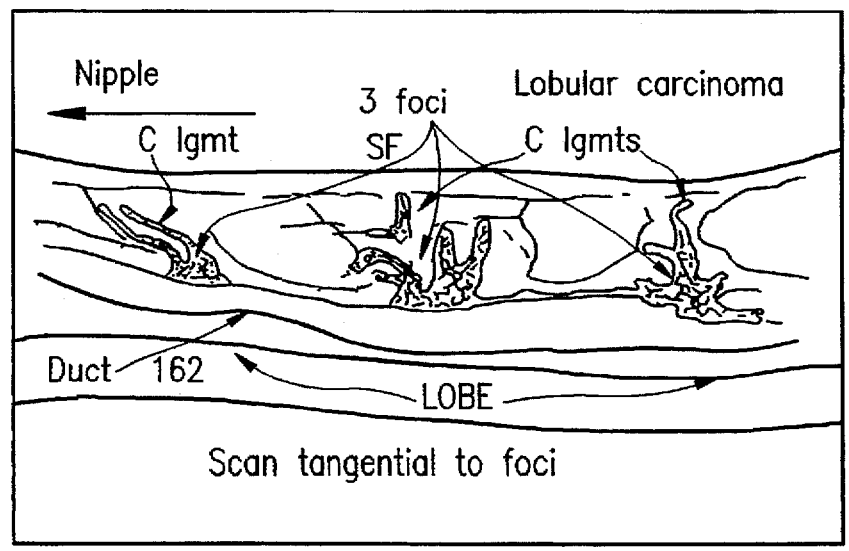

FIGS. 14a and 14b diagrammatically illustrate the axial ductal views in scan plane 171 and scan plane 173, respectively. In FIGS. 14a and 14b, lobular carcinoma is shown as having three foci in duct 162. In scan plane 171 (FIG. 13), as diagrammatically illustrated in FIG. 14a, that sonographic image displays a certain degree of foci and transverse ligaments along the SF or superficial fascia. In FIG. 14b, the Cooper's Ligament (C Lgmt), the three foci and the superficial fascia layer are differently identified and categorized. This corresponds to an ultrasonic scan along scan line 173. The three-dimensional image of duct 162 shown in FIG. 13 is a composite of the ultrasonic images in FIGS. 14a and 14b. To accomplish this, the axial aspects of duct 162 are aligned and displayed concurrently. Although the precise placement of the foci and Cooper's Ligaments is not exact, the visualization and presentation of this ultrasonic image in a composite or three-dimensional manner greatly assists the physician and technician in identifying the early stages of breast cancer. Further, the cross-sectional representation of the breast either in the vertical cross-section shown in display area 130 in FIG. 12 or the horizontal cross-sectional view in display area 130 in FIG. 12 also greatly assist the physician. By enabling the physician to switch back and forth between the composite, three-dimensional image and the axial composite, two-dimensional image shown in FIG. 12 and a further detailed image shown in display region 130 of FIG. 12, the physician can quickly focus from a broad study of the ductolobular system to a specific study of the lobe. Further, the general location of duct 18 can be shown in a clockface, as illustrated in connection with FIG. 10 above. The three-dimensional image may be formed by a plurality of oblique scan planes rather than just two scan planes.

Figure 15:
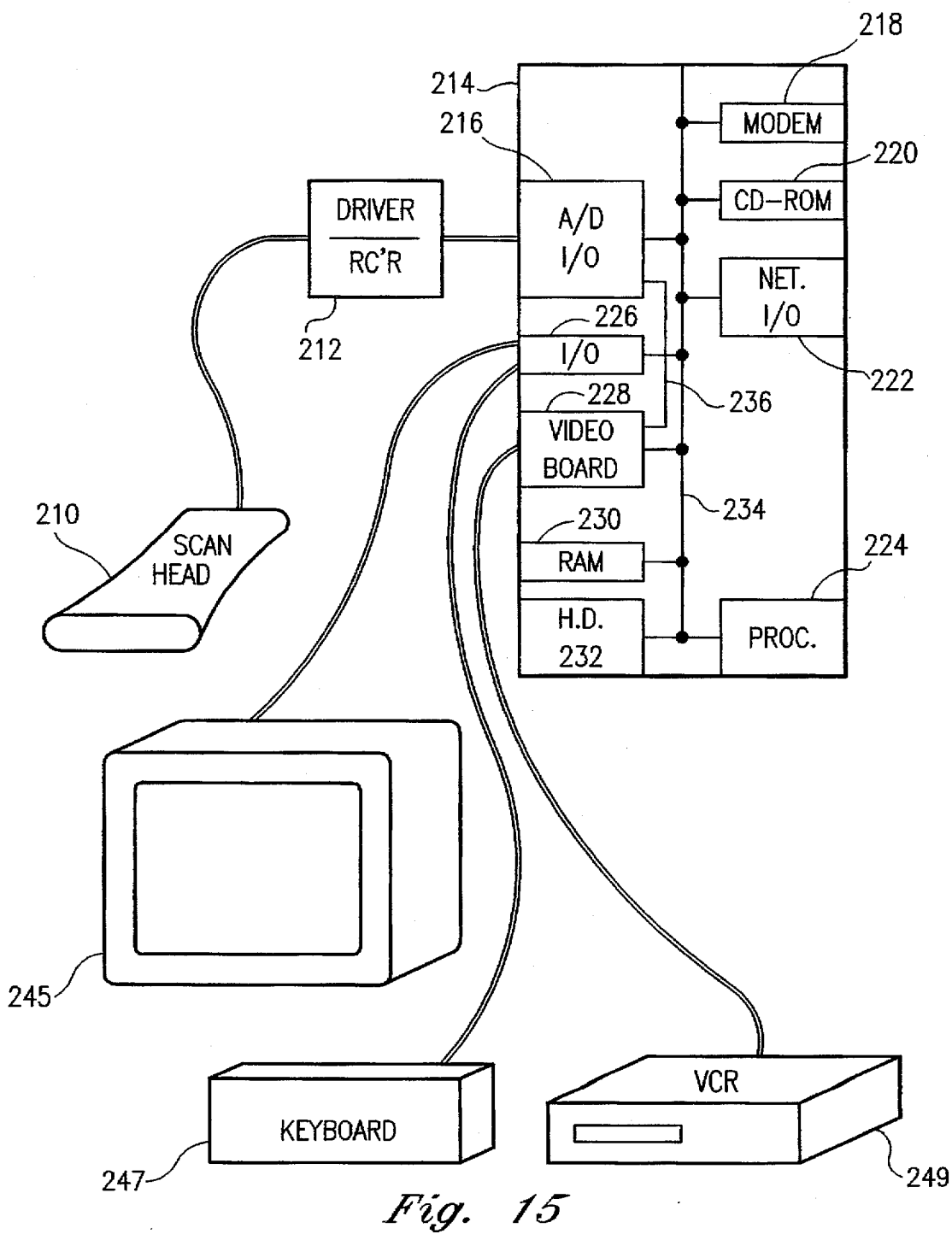
FIG. 15 diagrammatically illustrates one type of ultrasound machine.

FIG. 15 diagrammatically illustrates one type of ultrasound machine. It is believed that the present invention can be carried out in many different types of ultrasound machines, only one of which is diagrammatically illustrated in FIG. 15. The ultrasound machine includes scan head 210, a driver and a receiver 212 and a central control unit 214. The central control unit includes A to D input/output device 216, a modem 218, a CD ROM 220, an network input/output board 222, a control processor 224, an input/output board or device 226, a video processing board 228, an electronic memory configured as an RAM 230, and a hard drive 232. All of these internal components of central control unit 214 are connected together via a central bus 234. In addition, the video board 228 can include a small computer bus linking that video board with the A to D input/output 216 which is ultimately connected to scan head 210. This intermediate computer bus is shown as bus 236 in FIG. 15.

The system also includes a display monitor 245, a keyboard 247 and a video cassette recorder and player 249. Commonly, the VCR 249 is electrically connected to video board 228. Display monitor 225 and keyboard 247 are electronically connected to input/output board 226. The processor may be a PENTIUM CPU.

The sonographer will capture the electronic images of the breast as previously discussed. This information could be continuously electronically stored in hard drive 232 or on the tape in VCR 249. If the CD ROM 220 had a record mode, the electronic video images could be continuously recorded thereon. Thereafter, the computer could process these video images in a post-acquisition or post-processing phase rather than conducting the compilation and development of the composite axial ductal images and transaxial ductal images during the scan cycle as discussed later. The invention set forth herein covers both real time compilation of these three-dimensional and two dimensional images as well as the post-acquisition processing of these images.

Figure 16A:
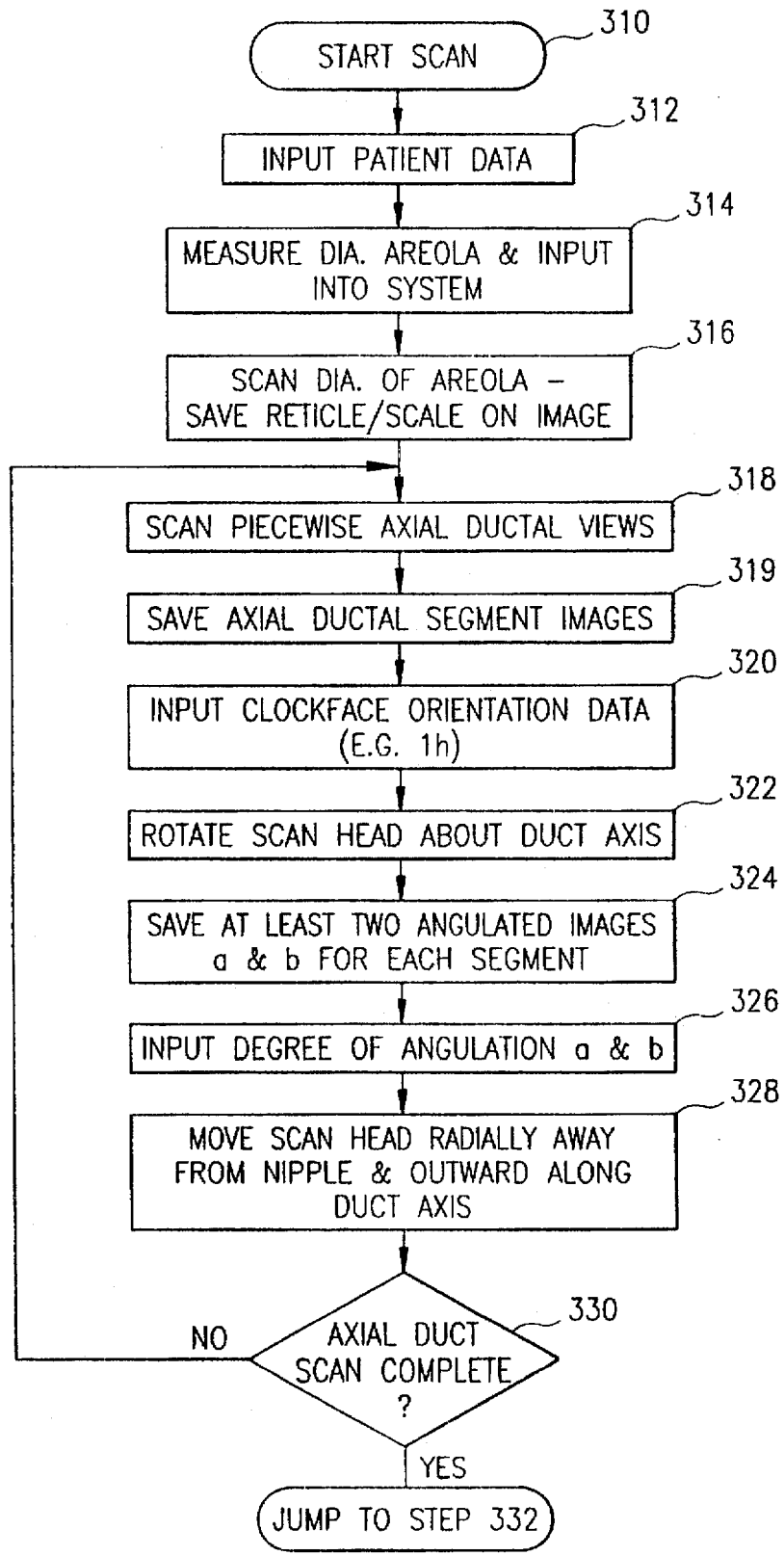
Figure 16B:
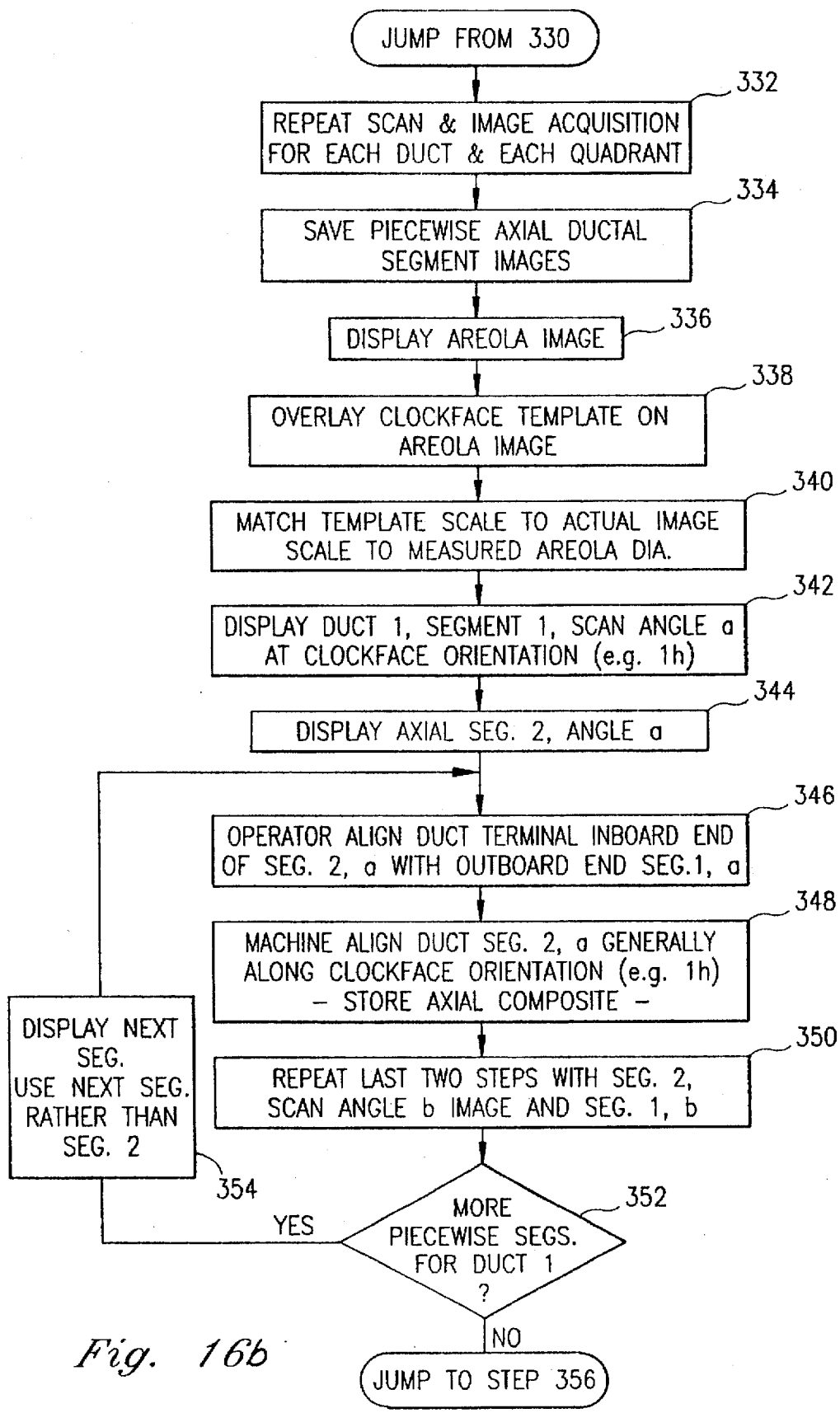
Figure 16C:
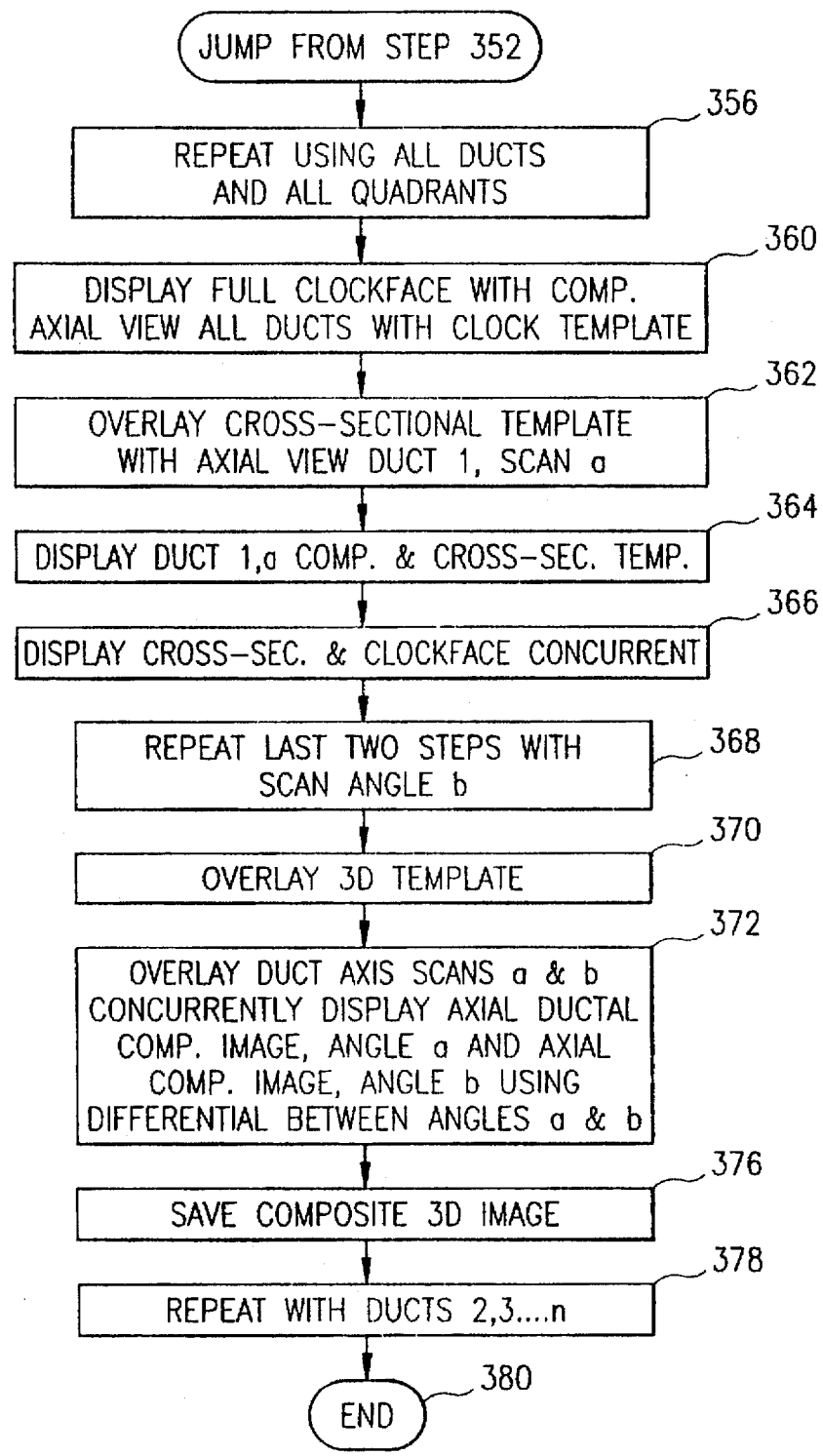

FIG. 16 illustrates a flow chart showing the major features of the computer system and method as part of the present invention. In FIG. 16, the operator starts the scan in step 310. In step 312, the sonographer enters the customary patient data. As is common, this patient data includes name of the patient, name of the sonographer, the date and other pertinent information, such as age and other physical conditions which the sonographer obtains from the patient. In step 314, the sonographer measures the diameter of the patient's areola and inputs this information into the computer system. Returning to system diagram 15, this input could be accomplished by keyboard 247 or may be accomplished by a touch screen and/or mouse control by selecting the correct dimensional size from the screen. In step 316, an ultrasonic scan of the diameter of the areola is conducted by the sonographer. The sonographer further saves the reticle with the scanned image and notes the scale on the electronically acquired image and saves this image in the appropriate memory. This memory may be on video board 228, RAM 230, hard drive 234 or continuously recorded by VCR 249.

The program continues and the operator conducts an ultrasound scan (a U.S. scan) in a piece-wise manner of the axial ductal segments in step 318. This axial ductal segment scan may encompass a ductal segment shown in FIG. 11a between section lines 1 and 2. When the operator moves the scan head radially outward in the direction shown as direction 3 in FIG. 7, the operator can then acquire an axial ductal image shown between section lines 2–3 in FIG. 11a. By saving, in a piece-wise manner, these axial ductal segments, the operator, either concurrently with the acquisition of the information or subsequently after the patient has completed the ultrasound, can piece these different axial segments together in order to arrive at the composite axial ductal view shown in FIG. 11a, FIG. 10 and also in the three-dimensional representation of FIG. 13.

Step 319 saves these axial ductal segment images in the appropriate memory. In step 320, the operator inputs the general clockface orientation for that duct. For example, most cancers appear in the upper and outer quadrants of the breasts. For the right breast this would refer to an upper quadrant of between 12–3:00. For the left breast, this corresponds to a quadrant between 9:00 and 12:00. When the operator inputs an electronic notation representing the general clockface orientation, the surgeon or physician, during his or her review of the acquired sonographic image, can easily locate that duct on the patient. The location of the duct under study may be significant because the patient can now focus on manipulating that particular duct. Further, the patient herself could then identify a particular problematic duct for further study and self manipulation. The location of the problematic duct is critical for follow-up ultrasound scans.

In step 322, the operator rotates the scan head around the axis of the duct. This routine conforms to the rotation to scan planes 171 and 173 in FIG. 13. Also, this corresponds to rotating scan head 93 in FIG. 7a in a direction shown by double headed arrow 2. By rotating the scan head using the axial aspect of the duct as the center of rotation, the sonographer acquires a significant amount of high quality information regarding ductal structure. When the sonographer views an important ductal position, the sonographer should save that acquired electronic image in the memory of the ultrasound machine, a computer as described in this environment. Further, the sonographer should save at least two angulated images or scan planes, corresponding to images a and b and generally corresponding to the images acquired in scan plane 171 and scan plane 173, illustrated in FIG. 13. This is noted in step 324 in FIG. 16. The sonographer should also electronically annotate or notate the degree of angulation a and b or the degree of angulation for the scan planes 171, 173 in FIG. 13. This is identified in step 326. The degree of angulation is stored in the system. After the sonographer has scanned that axial segment of the duct at both angles a and b, the sonographer should move radially away and outward in direction 3 shown in FIG. 7a. By moving the scan head in direction 3 axially along the duct, the sonographer then acquires new information about the radially outboard axial regions of the duct. This piece-wise image acquisition of sequential axial scans is noted in step 328.

In decision step 330, the system determines if the duct branch has been fully axially scanned. As discussed earlier, in a significant number of cases, there is a reoccurrence of breast cancer after the initial diagnosis and removal of cancerous cells from a particular duct. Further cancer oftentimes re-appears downstream or further radially away from the nipple. towards the periphery of the breast in lymphatic channels and nodes. Accordingly, it is important for the sonographer to scan the entire axial length of the duct as far as he or she can acquire electronic images of that duct up to and including the lymphatic system of the woman. Step 330 contemplates that the sonographer has scanned the radially outward regions of the duct and has acquired significance piece-wise axial images of the duct under study. If not, the NO branch is taken and the flow chart reverts to a position immediately prior to step 318. At that point, the sonographer moves the scan head radially away from the nipple and acquires further electronic imaging information from that duct.

If the YES branch is taken from decision step 330, the operator, in step 332, repeats the scan, electronic image acquisition for each duct in each quadrant. In this subroutine, the sonographer would look for each duct, would note the clockface orientation of the duct and continue to scan that duct for problematical areas. In step 334, the system requires the sonographer to save piece-wise axial ductal segment images.

In step 336, the system displays the ultrasonic image of the areola. In step 338, the system overlays the clockface template on the areola. This is shown above in connection with FIG. 10. In step 340, the operator matches the template scale to the actual electronic image scale and to the measured areola data or diameter. Accordingly, if the areola in 1" in diameter and the acquired electronic image is only ½" in diameter for that areola, the user would reduce the template 105 such that template line 105 would fall on top of the actual electronically acquired image. Template lines 105 would have an actual dimension of ½" because that complies with the acquired image. The scale shown on the display would also reveal that the actual dimension of the areola defined and illustrated within template lines 105 is 1", that is, the displayed image to actual size ratio is 1:2.

Since the electronic image of the areola will include an axial ductal segment of duct 18, all other axial segments for duct 18 could be similarly sized. As discussed later, the operator may magnify the image and abandon the size relationship.

In step 342, the current duct under study, identified as duct 1 in the flow chart, would be positioned roughly where the sonographer has noted that duct on the clockface orientation. Referring back to step 320, the ultrasound imaging system requests that the sonographer input general clockface orientation data for that particular duct under study. Accordingly, in order to use the clockface template illustrated in FIG. 10, the computer system would know generally where duct 18 falls in relationship to the overall clockface presentation. Accordingly, the first axial duct segment and the electronically acquired areola image are shown beneath the template illustrated as template 105, 103 and 101 in FIG. 10. In step 344, the sonographic system displays the next axial segment image, segment 2. This segment image is shown as the image acquired at angulation a. This may correspond to the scan plane 171 in FIG. 13. In step 346, the operator aligns the duct terminal inboard end of the second segment with an outboard terminal end of duct segment 1. One way of doing this is to have the second segment electronic image generally oriented along the same clockface orientation (1:00 hour), have the sonographer electronically grab the inboard terminal end of the duct that he or she sees on the second segment image and then have the sonographer drag that inboard terminal end and image segment to a point on the first acquired image. In this manner, the sonographer can match in a piece-wise manner the first axial segment image with the second axial segment image by matching and aligning like scan plane images in sequential axial segments.

To supplement this matching, the operator, after overlapping and aligning the outboard terminal end of the duct of the first segment image with the inboard terminal end of the duct of the second image (the terminal ends of the ducts), may release that target point in the second image, grab a second target point from the second image and move the second image. In this mode of operation, the second image would rotate about the fixed terminal ends of the ducts, fixed by the operator immediately prior thereto. This routine matches and aligns two like image points on two sequential axial image segments.

In step 348, the ultrasound machine aligns duct segment 2, angulation a generally along the 1:00 hour clockface orientation. In step 350, the system repeats the last two steps with axial duct segment 2, angulation b or scan plane b image. As discussed above, angulation b image may be the image acquired at scan plane 173. In decision step 352, the computer system requests whether there are more axial piece-wise segments for duct 1. If the YES branch is taken, the system, in step 354, displays the next axial segment of duct 1 and uses that next axial segment rather than segment 2. In other words, the system would gather axial segment 3, generally oriented in the clockface orientation, permit the sonographer to grab the radially inboard terminal end of the duct, drag that image to the radially outboard terminal end of the duct in image segment 2 and thereby anchor image segment 3 to image segment 2. The system loops around and executes steps 346, 348, 350 until, in decision step 352, the operator competes the piece-wise axial composition of duct 1. If the decision from decision step 352 is NO, reflecting the fact that the operator has completed the axial piece-wise segment of all the axial segments for duct 1, the system goes to step 356 which requests that the sonographer repeat the process for all the ducts in all the quadrants scanned by the sonographer.

The system then executes step 360 which displays the fully clockface image with all the ducts. In FIG. 10 only duct 18 is shown with the clockface image. However, it can be easily accomplished to show the physician or the technician all the ducts on the clockface presentation with the templates 109, 107, 105, 103 and 101. If the physician desires to have specific information on a certain duct, he or she can identify that duct simply by a point and click operation with a mouse or other type of computer input command sequence. In step 362, the computer system overlays the cross-sectional template generally shown above in connection with FIG. 12. The cross-sectional template includes template 126, a cross-sectional vertical illustration of the breast, template 124, the areola representation, and template 122, the template of the nipple.

It should be noted that at this point in time, the clockface display of all the ducts would include only one angulation information. In the cross-sectional display shown in step 364, a single angulation a is shown. Of course, the operator may choose to show a different angulation b or multiple angulations or scan planes (discussed below). In step 366, the system displays duct 1 in a cross-sectional view concurrently with the clockface view. The cross-sectional view is shown in display area 120 in FIG. 12 and the clockface view is shown in FIG. 10. In step 368, the computer system repeats the last two steps (steps 364 and 366) with angulation b. The operator may choose to show angulation a and shift back and forth between angulation a and angulation b. Alternatively, or in addition thereto, the operator could shift alternatively between clockface presentation shown in FIG. 10, vertical cross-sectional illustration shown in FIG. 12, display area 120 and further to the transaxial ductal view shown in display area 130 in FIG. 12. In step 370, the computer system generates the three-dimensional display shown in FIG. 13. This is accomplished because the operator has axially pieced together axial segments for the duct for angulation a as well as axial segments for the duct in angulation b. The duct is easily identified in the acquired electronic image by an edge detection routine. Further, it is relatively easy to locate other features in order to align axial segments together. For example, the axial view of the duct shown in FIG. 11a were actually 2–3 sonographic images pieced together by hand. The electronic placement and piece-wise addition to achieve a composite axial view of the duct is accomplished by the present invention. Accordingly, in step 372, the system concurrently displays the three-dimensional axial ductal composite image angulation a and the composite image angulation b using the difference between angulation a and angulation b. For example, referring specifically to FIG. 7a, the operator may choose angulation a as 30° and angulation b as 120°. On both of these angulations, the operator must select the same reference point on the skin, i.e., the same skin position and scan head side to measure the angulation. Since the operator is required to input angulation data in step 326, the computer system can readily determine the angle of separation between scan plane 171 and scan plane 173 in FIG. 13. It is important to note that the piece-wise assembly of the axial segments will not be perfect. Further, it should be noted that three-dimensional illustration of the ductal system will not be perfect. However, the three-dimensional presentation of the ductal image using at least two scan planes is so far superior to the X-ray mammographic techniques that the additional information conveyed has significant value to the physician. The relative position of the duct on the clockface and the sense of depth portrayed by the three-dimensional image system described herein cannot be underestimated. If the physician sees a problematic duct area, the physician may immediately begin an echo guided needle aspiration cytology. This medical routine is described above.

In step 376, the ultrasound machine saves the composite three-dimensional image. In step 378, the system repeats the assembly of the composite image for ducts 2, 3 . . . n. The program ends in step 380.

Figure 17A:
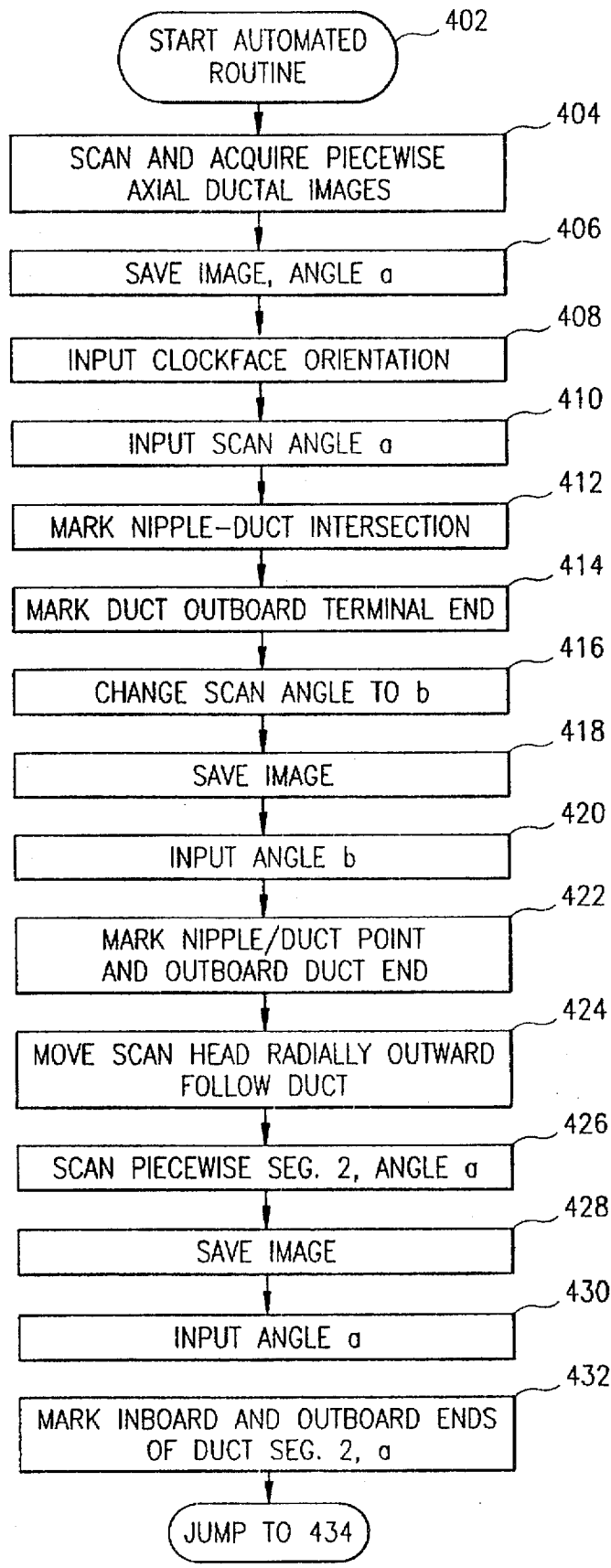
FIGS. 17a–b illustrate, in block diagram form, an automated flow chart for the system.
Figure 17B:
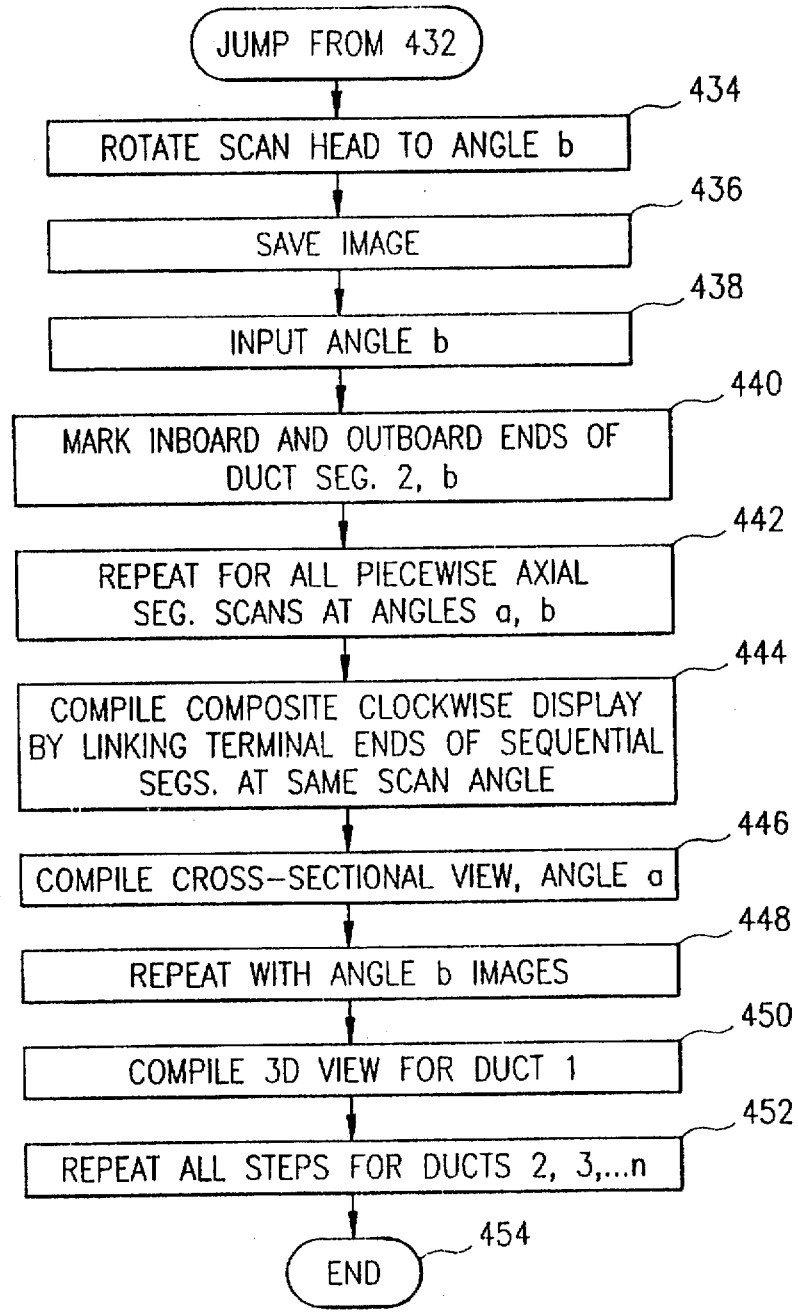

In addition to the foregoing, the system may be automated as shown in the flow chart block diagram 402. FIG. 17 illustrates, in block diagram form, an automated flow chart for the system. In step 404, the sonographer scans, in a piece-wise manner, the axial portions of the duct. In step 406, the system saves the image and the scan plane angle a. In step 408, the operator inputs the clockface orientation of that duct with respect to the nipple. In step 410, the operator inputs the scan angle a. In step 412, the operator electronically identifies the intersection of the nipple and the duct. This should be readily ascertainable in the first acquired image of the duct which includes the diameter of the areola. In step 414, the operator marks the terminal outboard end of the duct. In step 416, the operator changes the angulation of the scan to angle b. This corresponds to changing the angle in a direction shown by arrow 2 in FIG. 7a. In step 418, the operator saves the image.

In step 420, the operator is required to input the scan angle b. In step 422, the operator marks, on an electronic basis, the intersection of the nipple and the duct. Further, the operator identifies and makes an electronic notation on the image of the outboard terminal end of the duct. In step 424, the operator moves the scan head radially outboard following the duct. In step 426, the operator acquires axial scan images of segment 2, angle a. In step 428, the operator saves those electronic images. In step 430, the operator inputs angulation scan angle a. In step 432, the operator marks the inboard and outboard terminal ends of duct segment 2.

In step 434, the operator rotates the scan head to a new scan angle b. In step 436, the operator saves the image. In step 438, the operator inputs or electronically notes scan angle b. In 440, the operator electronically marks the inboard and radially outboard terminal ends of the duct segment 2 angulation b.

In step 442, the operator proceeds to obtain piece-wise axial scans of the duct at all angles a and b. In step 444, the computer system automatically locates the inboard and outboard ends of each duct and compiles the composite axial ductal image. This is a real time assembly of the axial composite image. The computer does this by placing the previously identified and annotated terminal ends of the ducts one on top of the other and further orients these piece-wise images generally along the clockface orientation as earlier input by the operator in step 408. In step 446, the system compiles the cross-sectional view of the duct at angle a. This corresponds to the view of duct 127 in display area 120 in FIG. 12. In step 448, the system repeats the compilation of a composite cross-sectional view for angle b. In step 450, the system compiles the three-dimensional view for duct 1 utilizing angulation information a and b and the compiled axial image of that duct. This corresponds to the three-dimensional image of the duct shown in FIG. 13. In step 452, the system process repeats the process for ducts 2, 3, ... n. The system ends in step 454.

Figure 18:
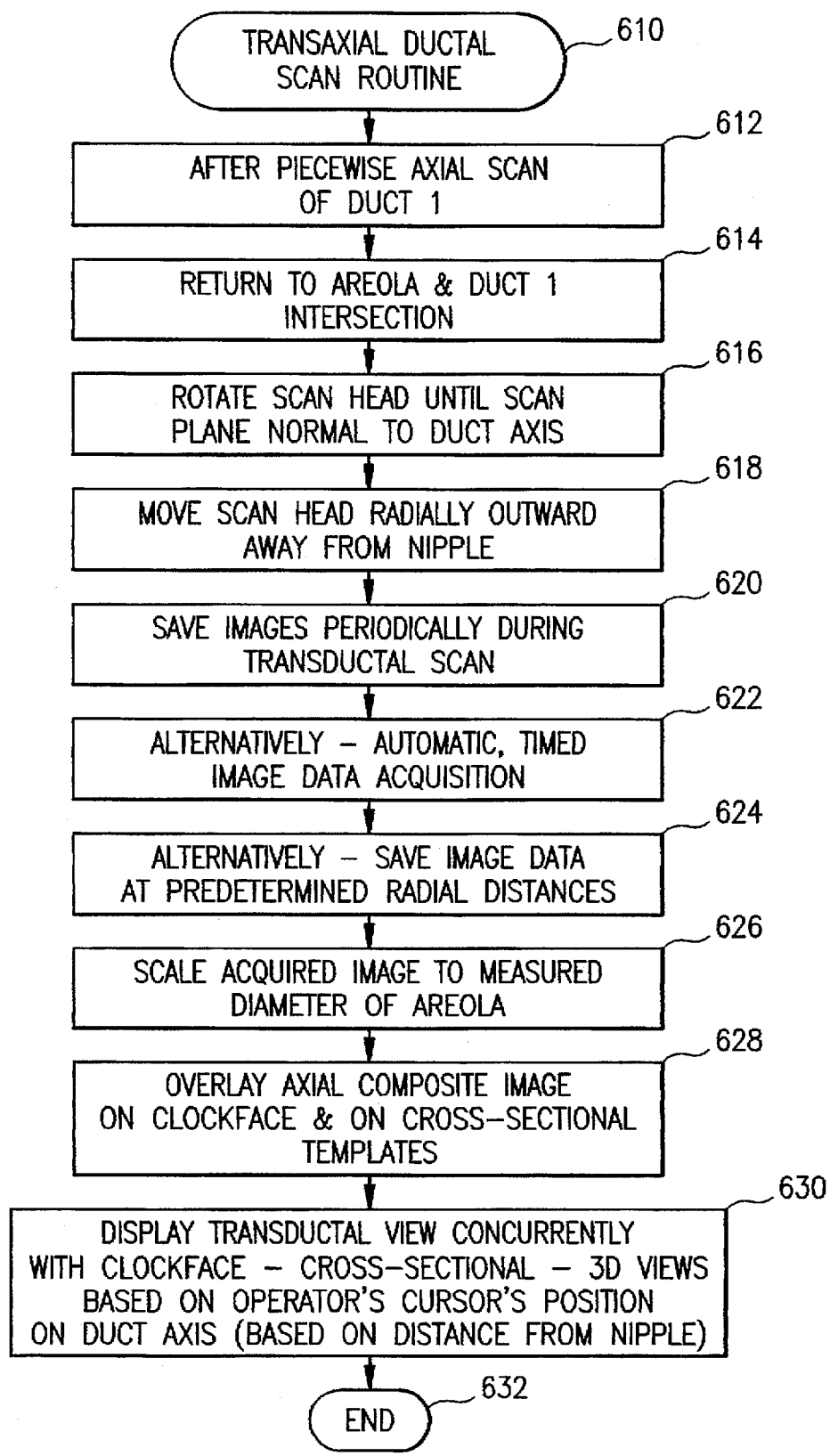
FIG. 18 illustrates, in block diagram form, a transductal scan routine which begins at step 610.

FIG. 18 illustrates, in block diagram form, a transductal scan routine which begins at step 610. In step 612, the system initiates the routine after the piece-wise axial scan of duct 1. In step 614, the system prompts the sonographer or the sonographer simply returns to the area of the areola and the intersection of duct 1. In step 616, the operator rotates the scan head as shown in FIG. 8a until the scan plane is normal to the duct axis, this is a transaxial scan. In step 618, the operator moves the scan head radially outward away from nipple 10. In step 620, the operator periodically saves the images during the transaxial ductal scan. This periodic saving of images could be timed by the computer or the images may be saved by a manual control command from the operator. As an alternative, step 622 provides for a timed data acquisition of the transductal scan, that is, the acquisition and saving of sonographic images during the manual scan and data acquisition. Step 624 recognizes that the system may be pre-programmed to save sonographic images at pre-determined radial distances away from nipple 10. It is known that some scan heads have position sensors and these position sensors can be used to generate timing signals to save the images.

Step 626 is the scaling step. Since the acquired image has a scale and since the operator has input the measured diameter of the areola, the operator can match the image scale to the actual measurement of the areola. On step 628, the system overlays the acquired, composite axial image on the clockface. This is shown above in connection with FIG. 10. In step 630, the system displays a position specific transductal view concurrently with the axial composite view. If the axial view is shown three-dimensionally, as shown in FIG. 13, the display of the transductal view shown in scan planes 176 and 178 could be accomplished automatically by the system. For example, the physician or sonographer could move scan plane image template 176 in the displayed composite axial image and the transductal image in display region 163 could change based upon the positional orientation of the cursor along the axis of the duct. In other words, at a 2 cm. position, the transductal view shown in region 163 would be different than if the cursor was placed at a 3 cm. axial position, that is, 3 cm. away from nipple 163. In this manner, the physician could change the transductal view based upon the location of his or her cursor on the screen on the axial composite view. In this manner, the physician could quickly visualize in a three-dimensional manner the axial view of the duct and then have a specific detailed transductal view from one or more saved transaxial ductal views. This image display system provides important, detailed information immediately at his or her fingertips. The routine ends in step 632.

The imaging system of the present invention may be enhanced in many ways. One enhancement utilizes color coding of the ductal systems in each quadrant. For example referring to FIGS. 6a and b, the radial outward scan lines may be disposed at every one-half hour. For example, radial scan lines at 12:00, 12:30, 1:00, 1:30, 2:00, 2:30 and 3:00 form the upper, outer quadrant in FIG. 6b. additionally, this upper, outer quadrant is, in a preferred embodiment, subdivided into a radially inner region and a radially outer region. Accordingly, eight (8) quadrants are utilized. The eight quadrants consist of four radially inner quadrants and four radially outer quadrants generally form a "bull's eye" over the clockface presentation of the breast. This radial clockface template or scan lines may be color coded red since certain regions of the breast has been statistically shown to carry high occurrences of breast cancer. In FIG. 6a, the upper, outer quadrant bounded by 9:00 and 12:00 may also be outlined or color coded in red. The remaining quadrants may be pink (a lesser statistical cancerous area), blue and green.

This color coding may be carried forward into the clockface template in FIG. 10, the cross-section templates (vertical and horizontal) in FIG. 12 and the three dimensional templates shown in FIG. 13.

In FIG. 10, the technician may initially elect to show all ductal systems in the clockface template. The imaging system of the present invention may include a selector command to enable the technician to select and highlight a singular ductal system. In other words, the full clockface presentation may show all the ducts, but the display would be "crowded" with imaging information. The operator could select a single duct or select a single quadrant of the breast to be shown in detail. Since the imaging information on the display screen would be reduced by this selection, the display of a single duct or multiple ducts in a single quadrant would show the ducts larger than the full clockface presentation of the entire breast. The template of the breast may be truncated to maintain a one-to-one scale of the ductal system and the size of the areola. The operator may further select the image scale as one-to-one based upon the image acquisition scale and the measured areola, or may select a magnified image scale wherein the ductal system image is shown as a multiple, e.g., twice as large, as the actual areola scale. The imaging system would include a simple command to switch back and forth between these two or three images (the first image being the full breast and clockface template, the second being the quadrant and the third being a single ductal system in the quadrant magnified or enlarged by a predetermined amount).

The color coding routine may be further expanded by enabling the operator to select different colors for each independent ductal system. In other words, the single duct shown in FIG. 10 may be shown in red. All other ducts in the quadrant could be shown in different colors. Of course, the operator may choose red to highlight a particularly problematic ductal system in order to focus the physician's attention on that duct.

Another enhancement of the present invention may include a display of the duct as in FIG. 10 after the creation of the three dimensional composite image in FIG. 13. In other words, the processing order set forth in the flow charts herein may be changed. In this enhanced routine, one of the scan plane images, e.g., plane 171, used to form the three dimensional image of the duct would be filtered such that only the axial region or display of the duct is shown in FIG. 10. The filtering of the image may be through common imaging techniques, e.g., edge detection and enhancement, or may be a selection of a range of imaging pixels around the duct. For example, the computer program, under the control of the operator, may select the equivalent of 1 centimeter of image around the central axial portion of the duct. This could be done for each axial scan segment. The identification of the ductal region may be piece-wise in that the duct sometimes "wanders" through the breast rather than extend radially outward from the nipple. A piece-wise or moving image range about the central axial portion of the duct would permit the imaging of a "wandering" or "meandering" ductal system. Duct 18 in FIG. 10 shows a meandering duct within radial region 101–103. The imaging system includes an operator selection to choose the filter, i.e., a wide image filter (2 cm.) or a small image filter (1 cm.). The geometric image filter's arcuate span may automatically increase based upon the radial distance between the scan segment and the nipple. FIG. 10 shows an increasing arcuate span. Image portions arcuately outboard of lines 101, 103 would be discarded.

With respect to FIGS. 12 and 13, the imaging system described herein may compile these images in real time, while the operator is scanning the patient, or may compile these images after the scan is complete. In any event, the operator must interactively select the duct during the data acquisition phase (the scanning phase) and follow the ductal system while the imaging system captures and records axial ductal segments and transaxial ductal views of the ductal system. The flow charts explained above provide only one method for acquiring and compiling these images (FIGS. 10, 12 and 13). The system may compile these images after the acquisition of the image data from the sonogram. The post image processing would use images saved in the computer memory or on the VCR. The operator would follow the processes discussed above on these saved, sequential images.

For example, the cross-sectional image in FIG. 12 may be compiled from scan plane 171 in FIG. 13 after the system compiles the three-dimensional image. The system may include an operator selection to switch between scan plane 171 and scan plane 173 while the operator is viewing the cross-sectional template image in FIG. 12. By permitting the operator to switch back and forth between these two images, the operator has a true picture of the scanned ductal system. In contrast, the three dimensional image presented in FIG. 13 inherently has some draw backs in that to align scans 171 and 173, there is an overlap of the ductal images on each scan plane axes and a consequential loss in imaging information due to this overlap. The ability of the system to easily switch back and forth between scan planes 171 and 173 while in the cross-sectional template mode (FIG. 12) enables to operator to clearly identify and classify potential malignancies in the ductal system.

Another enhancement to the present imaging system is the ability of the system to isolate an individual ductolobular cluster and discard the remaining radially inboard (towards the nipple) and radially outboard (away from the nipple) images associated with that ductal system. With respect to FIG. 13, the discarded axial portions would be portions more than about 2 cm. from transductal scan plane 176 and more than about 4 cm. radially away from plane 176. This imaging procedure would be under the control of the operator such that the operator would delete image portions at a certain axial distance away from the lobular system in both directions. The lobular system may be the malignant portion of the entire ductolobular system. The resulting image would show the lobular system standing in free space on the three dimensional template image of the breast. A farther enhancement of the system would be the display of several lobular systems on the breast in free standing form. The operator could then switch between the three-dimensional template and the clockface template where the same number of lobular systems would be shown at geometric locations on the clockface breast template. Another enhancement would include an operator's selection of color coding for each isolated lobular system on the clockface presentation.

The imaging system may also include a feature to enable the operator to rotate the three-dimensional image from the three dimensional presentation in FIG. 13 to the cross-sectional presentation of FIG. 12 and further to the clockface presentation in FIG. 10.

The imaging system can also be expanded to include the feature of electronically monitoring the position of the scan head on the breast of the patient. It is known that certain scan heads include position sensors. For example, the operator may scan the nipple of the patient and then mm ON the position sensor on the scan head. Thereafter when the operator moves the scan head away from the nipple, the position sensor tracks the distance the head moves relative to the nipple and the operator's ON command. The system could track and monitor the distance the scan head moves by monitoring the distance sensed by the position sensor and the associated electronic tracking program. This distance information may then be used to (a) confirm the relative radial position of the duct segment being scanned or (b) to trigger the SAVE and RECORD command to periodically save an image of the axial ductal scan.

The imaging system described herein is particularly adapted to breast investigation because the system produces three-dimensional images gathered by a small number of selected ultrasound scans. The arrangement of the scans on the ultrasound display monitor is easily understood because the number of scans is small, and because these scans are related to each other through their convergence towards the same ductal axis. See FIGS. 7a and 8a. Also, this relatively simple montage of a reduced number of scans is very informative because it shows the ability to display distinctly and specifically both the coalescent malignancy in the duct or lobules and the malignant extensions expanding in the main or in the few remaining superficial Cooper's ligaments diverging from involuted lobes. See FIGS. 10, 11a and 13.

The imaging system produces a new mode of display (FIGS. 6a, 6b, 10, 12 and 13) fundamentally different from that obtained with current scanning equipment. The system produces a new and an original mode of display which enhances an understanding of ultrasonic breast scans because the present mode of display corresponds to the mode of image acquisition by the operator. Development of the present system produces a new mode of ultrasonic imagery that will provide a more practical mode of display of ductal scans. This allows an immediate perception of the spatial arrangement of scanned structures.

One of the aims of the present patent is to provide an imaging system where the clockface orientation of the scan is shown on the screen (FIGS. 6a, 6b and 10) and corresponds to the sectioning plane in the examination procedure, and where the location of the scan in the organ or the body is immediately perceived through its adequate superimposition on a template or logo showing conspicuous anatomic reference marks (for example, the nipple and areola for the breast). In the three-dimensional imaging display shown in FIG. 13, the whole image can be displayed in perspective. This allows the operator to immediately perceive the spatial arrangement of different internal structures and observe the relationship existing between those structures. It is also possible to display concomitantly in the same picture a three-dimensional display in perspective with several scans sectioning the same structure or the same organ. See FIG. 13. Using the duct as a datum line or a reference marker for the scanning procedure and using a scanning mode centered by and on the duct, the arrangement of ductolobular structures appear to be determined by the duct, and the shape of the lobules appears to be dictated by the superficial Cooper's ligaments. The present technique offers three modes of display: (a) a scan display parallel to the ductal axis in order to display the whole lobe from one side to the other (FIG. 7a); (b) a display generated by the parallel transductal scanning for the evaluation of a short segment of a lobe containing a lesion (FIG. 8a); and (c) axial ductal scanning in a sector of cylinder using the duct as a hub and the skin of the breast as the surface of revolution (FIG. 13). The scanning system has the ability to store in the computer memory several axial ductal scans performed at different scanning angles while keeping those scanned images always related to each other through their link with the duct. This enables the operator to select only a few scans stored in the memory by spooling on the screen or otherwise and to discard other scans determined to contain less information.

The claims appended hereto are meant to cover modifications and changes within the spirit and scope of the present invention.

What is claimed is:

1. A method of displaying, on a display monitor of an ultrasound imaging machine, a plurality of ultrasound images obtained from a plurality of ultrasound scans of a ductal system in a breast comprising the steps of:

obtaining and electronically storing a plurality of axial ductal ultrasound scan images of said breast, each image including an image of a longitudinal segment of a duct in said breast;

obtaining and electronically storing a plurality of transaxial ductal ultrasound scan images over said longitudinal duct segment;

electronically scaling said ductal images to a known, measured feature of said breast;

directionally orienting said ductal image to said known feature of said breast;

providing an electronic imaging template outlining predetermined features of a breast;

displaying the plurality of axial ductal images substantially concurrently with said imaging template representing said breast on said display monitor; and, concurrently displaying said axial ductal images and said transaxial ductal images on corresponding regions on said display monitor upon command.

2. A method of displaying as claimed in claim 1 including the step of obtaining and electronically storing a plurality of axial ductal ultrasound scan images of a plurality of ducts, each image including an image of a longitudinal segment of a respective duct of said plurality of ducts in said breast, the step of directionally orienting including the step of orienting each respective axial ductal image in a clockface, frontal representation of said breast with a nipple of said breast being electronically imaged at a central region of said clockface, and the step of providing an electronic imaging template including the step of providing an electronic clockface frontal imaging template of said breast, said predetermined feature being said nipple of said breast, and the step of displaying including the step of displaying said plurality of axial ductal images over said clockface imaging template on said display monitor.

3. A method of displaying as claimed in claim 2 wherein the step of directionally orienting includes the step of providing an orientation imaging template display with a plurality of wedge-shaped arcuate sections, and the step of electronically orienting utilizing respective axial ductal images within a corresponding arcuate imaging section.

4. A method of displaying as claimed in claim 3 including the steps of electronically selecting one of said plurality of axial ductal images, and the method includes the step of enlarging the selected ductal image on said display monitor.

5. A method of displaying as claimed in claim 4 including the step of electronically switching between said displayed plurality of axial ductal images over said clockface imaging template and said enlarged, selected ductal image.

6. A method of displaying as claimed in claim 1 wherein said step of providing an imaging template includes providing an electronic imaging template of a vertical, medially aligned cross-sectional outline of said breast, and the step of displaying displays said plurality of axial ductal images concurrently over said vertical, cross-sectional imaging template.

7. A method of displaying as claimed in claim 1 wherein the step of obtaining and electronically storing includes the step of obtaining and electronically storing a plurality of axial ductal ultrasound scan images of different, sequential longitudinal segments of the same duct in said breast, and the method includes the step of aligning, in a piece-wise manner, said plurality of axial ductal images of sequential longitudinal ductal segments.

8. A method of displaying as claimed in claim 7 including the step of sequentially obtaining said plurality of axial ductal ultrasound scan images of sequential longitudinal segments of the same duct during the step of obtaining and electronically storing, the step of alignment including the step of aligning similar respective image points on each ductal scan.

9. A method of displaying as claimed in claim 8 wherein the step of alignment utilizes image points from the group comprising a duct image point, a nipple image point from a scanned image of a nipple of said breast, and a skin surface image point from a scanned image of a skin surface above said ductal system.

10. A method of displaying as claimed in claim 8 including the step of obtaining and electronically storing a first plurality of axial ductal ultrasound scan images of said longitudinal segment of said duct at a first scanning plane angle and obtaining and electronically storing a second plurality of axial ductal ultrasound scan images of said longitudinal segment of said duct at a second scanning plane angle wherein said first and second scanning planes intersect substantially along a central axis of said longitudinal ductal segment, and the method including the step of aligning similar respective image points on said first scanning plane image and said second scanning plane image.

11. A method of displaying as claimed in claim 10 wherein the step of aligning first and second scanning plane images utilizes image points from respective duct image points in said first and second scan images.

12. A method of displaying as claimed in claim 11 wherein the step of providing an electronic imaging template provides an electronic imaging template for displaying a perspective, three dimensional outline view of said breast.

13. A method of displaying as claimed in claim 3 including the step of truncating said axial ductal scan image within a predetermined imaging region centered about said longitudinal duct segment.

14. A method of displaying as claimed in claim 12 including the step of obtaining and electronically storing a plurality of transaxial ductal ultrasound scan images over said longitudinal duct segment, and the step of concurrently displaying said axial ductal images and said transaxial ductal images on corresponding regions on said display monitor.

15. A method of displaying as claimed in claim 6 including the step of obtaining and electronically storing a plurality of transaxial ductal ultrasound scan images over said longitudinal duct segment, and the step of concurrently displaying said axial ductal images and said transaxial ductal images on corresponding regions on said display monitor.

16. A method of displaying as claimed in claim 15 including the step of truncating said axial ductal scan image a within predetermined imaging region centered about said longitudinal ductal segment.

17. A method of displaying as claimed in claim 9 including the step of truncating said axial ductal scan image a within predetermined imaging region centered about said longitudinal ductal segment.

18. A method of displaying, on a display monitor of an ultrasound imaging machine, a plurality of ultrasound images obtained from a plurality of ultrasound scans of a ductal system in a breast comprising the steps of:

obtaining and electronically storing a plurality of axial ductal ultrasound scan images of a plurality of ducts of said breast, each image including an image of a longitudinal segment of a respective duct in said breast;

truncating said axial ductal scan image a within predetermined imaging region centered about said longitudinal ductal segment;

electronically scaling said ductal images to a known, measured feature of said breast;

providing an electronic imaging template outlining at least one predetermined feature of said breast, including providing an electronic clockface frontal imaging template of said breast;

directionally orienting said ductal image to said known feature of said breast, including orienting each respective axial ductal image in a clockface, frontal representation of said breast;

providing an orientation imaging template display with a plurality of wedge-shaped arcuate sections, the step of electronically orienting utilizing respective axial ductal images within a corresponding arcuate imaging section;

displaying the plurality of axial ductal images substantially concurrently with said imaging template representing said breast on said display monitor, said plurality of axial ductal images being imaged over said clockface imaging template on said display monitor.

19. A method of displaying as claimed in claim 1 including the step of color coding the image of each longitudinal ductal segment image on said display monitor.

20. A method of displaying as claimed in claim 3 including the step of color coding the image of each longitudinal ductal segment image on said display monitor.

21. A method of displaying as claimed in claim 9 including the step of color coding the image of each longitudinal ductal segment image on said display monitor.

22. A method of displaying as claimed in claim 15 including the step of color coding the image of each longitudinal ductal segment image on said display monitor.

23. A method of displaying, on a display monitor of an ultrasound imaging machine, a plurality of ultrasound images obtained from a plurality of ultrasound scans of a ductal system in a breast comprising the steps of:

obtaining and electronically storing a first plurality of axial ductal ultrasound scan images of a longitudinal segment of a duct in said breast at a first scanning plane angle;

obtaining and electronically storing a second plurality of axial ductal ultrasound scan images of said longitudinal segment of said duct at a second scanning plane angle wherein said first and second scanning planes intersect substantially along a central axis of said longitudinal ductal segment;

obtaining and electronically storing a plurality of transaxial ductal ultrasound scan images over one of said first and said second longitudinal duct segments;

truncating said first and second axial ductal scan images a within predetermined imaging region centered about said longitudinal ductal segment;

aligning similar respective image points on said first scanning plane image and said second scanning plane image, the step of aligning first and second scanning plane images utilizing image points from respective duct image points in said first and second scan images;

directionally orienting said first and second ductal images to a known feature of said breast;

providing an electronic imaging template outlining predetermined features of said breast, including an electronic imaging template for displaying a perspective, three dimensional outline view of said breast;

displaying the first and second aligned axial ductal images substantially concurrently with said imaging template representing said breast on said display monitor;

concurrently displaying said aligned axial ductal images and said transaxial ductal images on corresponding regions on said display monitor upon command.

24. A method of displaying as claimed in claim 23 including the step of color coding the image of said aligned axial ductal segment images on said display monitor.

25. An ultrasound imaging system which obtains and electronically stores a plurality of axial ductal ultrasound scan images of a breast, each axial ductal image including an image of a longitudinal segment of a duct in said breast, said ultrasound imaging system including a display monitor for viewing said plurality of ultrasound images, said imaging system comprising:

means for electronically scaling said axial ductal images to a representation of a known, measured feature of said breast;

means for truncating said axial ductal scan images a within predetermined imaging region centered about said longitudinal ductal segment;

means for directionally orienting said ductal image with respect to said representation of said known feature of said breast;

an imaging template viewable on said display and outlining at least one predetermined feature of a breast, said imaging template being one of a clockface, frontal representation of said breast and a vertical, medially aligned cross-sectional outline of said breast;

means for displaying the plurality of axial ductal images substantially concurrently with said imaging template representing said breast on said display monitor, said means for displaying displays said plurality of axial ductal images concurrently over one of said clockface template and said vertical, cross-sectional imaging template upon command;

means for color coding the said axial ductal images on said display monitor.

26. An imaging system as claimed in claim 25 wherein said imaging system obtains and electronically stores a plurality of transaxial ductal ultrasound scan images over said longitudinal segment of said duct in said breast and the imaging system includes:

means for concurrently displaying said transaxial ductal images and said axial ductal images at corresponding regions on said display monitor.

27. An imaging system as claimed in claim 25 wherein said imaging system obtains and electronically stores a plurality of axial ductal ultrasound scan images over sequential longitudinal segments of said duct in said breast and the imaging system includes:

means for aligning, in a piece-wise manner, said plurality of axial ductal images of sequential longitudinal ductal segments;

said means for displaying aligned ductal images.

28. An imaging system as claimed in claim 25 wherein said means for aligning includes means for aligning similar respective image points on each ductal scan, said image points being image points from the group comprising a duct image point, a nipple image point from a scanned image of a nipple of said breast, and a skin surface image point from a scanned image of a skin surface above said ductal system.

29. An ultrasound imaging system which obtains and electronically stores first and second pluralities of axial ductal ultrasound scan images of a ductal system in a breast, said first and second images obtained at respective first and second scanning plane angles such that the intersection of said first and second scanning planes substantially coincides with a central axis of a longitudinal segment of the scanned duct, said ultrasound imaging system including a display monitor for viewing said plurality of ultrasound images, said imaging system comprising:

means for truncating said axial ductal scan images a within predetermined imaging region centered about said longitudinal ductal segment;

means for aligning similar respective image points on said first scanning plane ductal image and said second scanning plane ductal image, said means for aligning first and second scanning plane ductal images utilizes image points from respective duct image points in said first and second scan images;

means for directionally orienting said first and second ductal images to a representation of a known feature of said breast;

an electronic imaging template outlining predetermined features of said breast and displaying a perspective, three dimensional outline view of said breast upon command;

means for displaying the first and second aligned axial ductal images substantially concurrently with said imaging template representing said breast on said display monitor; and, means for color coding the said axial ductal images on said display monitor.

30. An imaging system as claimed in claim 29 wherein said imaging system obtains and electronically stores a plurality of transaxial ductal ultrasound scan images over said longitudinal segment of said duct in said breast and the imaging system includes:

means for concurrently displaying said transaxial ductal images and one of said first and second axial ductal images at corresponding regions on said display monitor.

31. An imaging system as claimed in claim 30 wherein said imaging system obtains and electronically stores scan images at said first and second scanning planes over sequential longitudinal segments of said duct and the imaging system includes:

means for aligning, in a piece-wise manner, said plurality of axial ductal images at each scanning plane for sequential longitudinal ductal segments;

said means for displaying aligned ductal images.

32. An imaging system as claimed in claim 31 wherein said means for aligning includes means for aligning similar respective image points on each ductal scan, said image points being image points from the group comprising a duct image point, a nipple image point from a scanned image of a nipple of said breast, and a skin surface image point from a scanned image of a skin surface above said ductal system.

* * * * *